United States Patent [19]
Saito et al.

[11] Patent Number: 5,665,872
[45] Date of Patent: Sep. 9, 1997

[54] LDL RECEPTOR ANALOG PROTEIN AND DNA CODING THEREFOR

[75] Inventors: Yasushi Saito, Chiba; Akio Iwasaki, Tsuchiura; Koichi Arai, Urawa; Hiroyuki Yamazaki, Higashimurayama, all of Japan

[73] Assignee: Kowa Co., Ltd., Nagoya, Japan

[21] Appl. No.: 727,034

[22] Filed: Oct. 8, 1996

[30] Foreign Application Priority Data

Oct. 9, 1995 [JP] Japan ................................. 7-261440
Apr. 24, 1996 [JP] Japan ................................. 8-102451

[51] Int. Cl.$^6$ .................. C07H 21/04; C12N 15/85; C12N 15/63; C07K 14/46
[52] U.S. Cl. .................. 536/23.5; 530/388.25; 530/350; 435/320.1; 435/325
[58] Field of Search .................. 536/23.5; 530/388.25, 530/350; 435/320.1, 325; 478/69.1; 475/252.3

[56] References Cited

U.S. PATENT DOCUMENTS 5,521,071  5/1996  Attie et al. .......................... 435/69.1

OTHER PUBLICATIONS

Strickland et al. FASEB J. 9,890. 1995.

*Primary Examiner*—John Ulm
*Assistant Examiner*—Mukul Ranjan
*Attorney, Agent, or Firm*—Oblon, Spivak, McClelland, Maier & Neustadt, P.C.

[57] ABSTRACT

The present invention is drawn to a DNA encoding a novel LDL receptor-analog. LDL receptors participate in lipoprotein metabolism, which is a critical factor in the onset of arteriosclerosis. The invention provides DNA having the nucleotide sequences shown by SEQ ID NOS: 1 and 5, which encode rabbit and human LDL receptor analog proteins having the sequences shown in SEQ ID NOS: 3 and 7 respectively.

7 Claims, No Drawings

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 6639 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:1:

```
ATGGCGACAC  GGAGCAGCAG  GAGGGAGTCG  CGACTCCCCT  TCCTATTCAC  CCTGGTCGCG      60

CTGCTGCCGC  CCGGGGCTCT  CTGCGAGGTG  TGGACGCGGA  CACTGCACGG  CGGCCGCGCG     120

CCCTTACCCC  AGGAGCGGGG  CTTCCGCGTG  GTGCAGGGCG  ACCCGCGCGA  GCTGCGGCTG     180

TGGGAGCGCG  GGGATGCCAG  GGGGGCGAGC  CGGGCGGACG  AGAAGCCGCT  CCGGAGGAGA     240

CGGAGCGCTG  CCCTGCAGCC  CGAGCCCATC  AAGGTGTACG  GACAGGTCAG  CCTCAATGAT     300

TCCCACAATC  AGATGGTGGT  GCACTGGGCC  GGAGAGAAAA  GCAACGTGAT  CGTGGCCTTG     360

GCCCGGGACA  GCCTGGCGTT  GGCCAGGCCC  AGGAGCAGTG  ATGTGTACGT  GTCTTATGAC     420

TATGGAAAAT  CATTCAATAA  GATTCAGAG  AAATTGAACT  TCGGCGCGGG  AAATAACACA     480
```

```
GAGGCTGTGG TGGCCCAGTT CTACCACAGC CCTGCGGACA ACAAACGGTA CATCTTCGCA      540
GATGCCTACG CCCAGTATCT CTGGATCACG TTTGACTTCT GCAACACCAT CCATGGCTTT      600
TCCATCCCGT TCCGGGCAGC TGATCTCCTA CTCCACAGTA AGGCCTCCAA CCTTCTCCTG      660
GGCTTCGACA GGTCTCACCC CAACAAGCAG CTGTGGAAGT CGGATGATTT TGGCCAGACC      720
TGGATCATGA TTCAAGAACA CGTGAAGTCC TTTTCTTGGG GAATTGATCC CTATGACAAA      780
CCAAACACCA TCTACATCGA ACGGCACGAA CCTTCTGGCT ACTCCACGGT TTTCCGAAGT      840
ACAGACTTCT TCCAGTCCCG GGAAAACCAG GAAGTGATCT TGGAGGAAGT GAGAGACTTT      900
CAGCTTCGGG ACAAGTACAT GTTGCTACA AAGGTGGTGC ATCTCTTGGG CAGTCCACTG      960
CAGTCTTCTG TCCAGCTCTG GGTCTCCTTT GGCCGGAAGC CATGCGGGC CGCCCAGTTT     1020
GTTACAAGAC ATCCTATCAA CGAATATTAC ATCGCGGATG CCTCGGAGGA CCAGGTGTTT     1080
GTGTGTGTCA GTCACAGCAA CAACCGCACC AACCTCTACA TCTCGGAGGC AGAGGGCTTG     1140
AAGTTCTCTC TGTCCCTGGA GAACGTGCTC TACTACACCC CGGGAGGGGC CGGCAGTGAC     1200
ACCTTGGTGA GGTACTTTGC AAATGAACCG TTTGCTGACT CCATCGTGT GGAAGGGTTG     1260
CAGGGAGTCT ACATTGCTAC TCTGATTAAT GGTTCTATGA ATGAGGAGAA CATGAGATCT     1320
GTCATCACCT TTGACAAAGG GGGCACCTGG GAATTTCTGC AGGCTCCAGC CTTCACGGGG     1380
TATGGAGAGA AAATCAACTG TGAGCTGTCC GAGGGCTGTT CCCTCCACCT GGCCCAGCGC     1440
CTCAGCCAGC TGCTCAACCT CCAGCTCCGG AGGATGCCCA TCCTGTCCAA GGAGTCGGCG     1500
CCTGGCCTCA TCATTGCCAC GGGCTCAGTG GGAAAGAACT TGGCTAGCAA GACAAACGTG     1560
TACATCTCTA GCAGTGCTGG AGCCAGGTGG CGAGAGGCAC TTCCTGGACC TCACTACTAT     1620
ACATGGGGAG ACCATGGCGG CATCATCATG GCCATTGCCC AAGGCATGGA AACCAACGAA     1680
CTGAAGTACA GTACCAACGA AGGGGAGACC TGGAAAGCCT TCACCTTCTC TGAGAAGCCC     1740
GTGTTTGTGT ATGGGCTCCT CACGGAACCC GGCGAGAAGA GCACGGTCTT CACCATCTTT     1800
GGCTCCAACA AGGAGAACGT GCACAGCTGG CTCATCCTCC AGGTCAATGC CACAGACGCC     1860
CTGGGGGTTC CTTGCACAGA GAACGACTAC AAGCTCTGGT CACCATCTGA TGAGCGGGGG     1920
AATGAGTGTT TGCTTGGACA CAAGACTGTT TTCAAACGGA GGACCCCGCA CGCCACATGC     1980
TTTAACGGAG AAGACTTTGA CAGGCCGGTG GTTGTGTCCA ACTGCTCCTG CACCCGGGAG     2040
GACTATGAGT GTGACTTTGG CTTCCGGATG AGTGAAGACT TGGCATTAGA GGTGTGTGTT     2100
CCAGATCCAG GATTTTCTGG AAAGTCCTCC CCTCCAGTGC CTTGTCCCGT GGGCTCTACG     2160
TACAGGCGAT CAAGAGGCTA CCGGAAGATT TCTGGGGACA CCTGTAGTGG AGGAGATGTT     2220
GAGGCACGGC TAGAAGGAGA GCTGGTCCCC TGTCCCCTGG CAGAAGAGAA CGAGTTCATC     2280
CTGTACGCCA CGCGCAAGTC CATCCACCGC TATGACCTGG CTTCCGGAAC CACGGAGCAG     2340
TTGCCCCTCA CTGGGTTGCG GGCAGCAGTG GCCCTGGACT TGACTATGA GCACAACTGC     2400
CTGTATTGGT CTGACCTGGC CTTGGACGTC ATCCAGCGCC TCTGTTTGAA CGGGAGTACA     2460
GGACAAGAGG TGATCATCAA CTCTGACCTG GAGACGGTAG AAGCTTTGGC TTTTGAACCC     2520
CTCAGCCAAT TACTTTACTG GGTGGACGCA GGCTTTAAAA AGATCGAGGT AGCCAATCCA     2580
GATGGTGACT TCCGACTCAC CGTCGTCAAT CCTCGGTGC TGGATCGGCC CCGGGCCCTG     2640
GTCCTTGTGC CCCAAGAAGG GATCATGTTC TGGACCGACT GGGGAGACCT GAAGCCTGGG     2700
ATTTATCGGA GCAACATGGA CGGATCTGCC GCCTATCGCC TCGTGTCGGA GGATGTGAAG     2760
TGGCCCAATG GCATTTCCGT GGACGATCAG TGGATCTACT GGACGGATGC CTACCTGGAC     2820
TGCATTGAGC GCATCACGTT CAGCGGCCAG CAGCGCTCCG TCATCCTGGA CAGACTCCCG     2880
```

```
CACCCCTATG CCATTGCTGT CTTTAAGAAT GAGATTTACT GGGATGACTG GTCACAGCTC    2940
AGCATATTCC GAGCTTCTAA GTACAGCGGG TCCCAGATGG AGATTCTGGC CAGCCAGCTC    3000
ACGGGGCTGA TGGACATGAA GATCTTCTAC AAGGGGAAGA ACACAGGAAG CAATGCGTGT    3060
GTACCCAGGC CGTGCAGCCT GCTGTGCCTG CCCAGAGCCA ACAACAGCAA AAGCTGCAGG    3120
TGTCCAGATG GCGTGGCCAG CAGTGTCCTC CCTTCGGGG  ACCTGATGTG TGACTGCCCT    3180
AAGGGCTACG AGCTGAAGAA CAACACGTGT GTCAAAGAAG AAGACACCTG TCTGCGCAAC    3240
CAGTACCGCT GCAGCAACGG GAACTGCATC AACAGCATCT GGTGGTGCGA TTTCGACAAC    3300
GACTGCGGAG ACATGAGCGA CGAGAAGAAC TGCCCTACCA CCATCTGCGA CCTGGACACC    3360
CAGTTCCGTT GCCAGGAGTC TGGGACGTGC ATCCCGCTCT CCTACAAATG TGACCTCGAG    3420
GATGACTGTG GGACAACAG  TGACGAAAGG CACTGTGAAA TGCACCAGTG CCGGAGCGAC    3480
GAATACAACT GCAGCTCGGG CATGTGCATC CGCTCCTCCT GGGTGTGCGA CGGGGACAAC    3540
GACTGCAGGG ACTGGTCCGA CGAGGCCAAC TGCACAGCCA TCTATCACAC CTGTGAGGCC    3600
TCCAACTTCC AGTGCCGCAA CGGGACTGC  ATCCCCAGC  GGTGGGCGTG TGACGGCGAC    3660
GCCGACTGCC AGGATGGCTC TGATGAGGAT CCAGCCAACT GTGAGAAGAA GTGCAACGGC    3720
TTCCGCTGCC CGAACGGCAC CTGCATTCCC TCCACCAAGC ACTGTGACGG CCTGCACGAT    3780
TGCTCGGACG GCTCCGACGA GCAGCACTGC GAGCCCCTGT GTACACGGTT CATGGACTTC    3840
GTGTGTAAGA ACCGCCAGCA GTGCCTCTTC CACTCCATGG TGTGCGATGG GATCATCCAG    3900
TGCCGTGACG GCTCCGACGA GGACCCAGCC TTTGCAGGAT GCTCCCGAGA CCCCGAGTTC    3960
CACAAGGTGT GCGATGAGTT CGGCTTCCAG TGTCAGAACG GCGTGTGCAT CAGCTTGATC    4020
TGGAAGTGCG ACGGGATGGA TGACTGCGGG GACTACTCCG ACGAGGCCAA CTGTGAAAAC    4080
CCCACAGAAG CCCCCAACTG CTCCCGCTAC TTCCAGTTCC GGTGTGACAA TGGCCACTGC    4140
ATCCCCAACA GGTGGAAGTG TGACAGGGAG AATGACTGTG GGACTGGTC  CGACGAGAAG    4200
GACTGTGGAG ATTCACATGT ACTTCCGTCT ACGACTCCTG CACCCTCCAC GTGTCTGCCC    4260
AATTACTACC GCTGCGGCGG GGGGCCTGC  GTGATAGACA CGTGGGTTTG TGACGGGTAC    4320
CGAGATTGCG CAGATGGATC CGACGAGGAA GCCTGCCCCT CGCTCCCAA  TGTCACTGCC    4380
ACCTCCTCCC CCTCCCAGCC TGGACGATGC GACCGATTTG AGTTTGAGTG CCACCAGCCA    4440
AAGAAGTGCA TCCCTAACTG GAGACGCTGT GACGGCCATC AGGATTGCCA GGATGGCCAG    4500
GACGAGGCCA ACTGCCCCAC TCACAGCACC TTGACCTGCA TGAGCTGGGA GTTCAAGTGT    4560
GAGGATGGCG AGGCCTGCAT CGTGCTGTCA GAACGCTGCG ACGGCTTCCT GGACTGCTCA    4620
GATGAGAGCG ACGAGAAGGC CTGCAGTGAT GAGTTAACTG TATACAAAGT ACAGAATCTT    4680
CAGTGGACAG CTGACTTCTC TGGGAATGTC ACTTTGACCT GGATGCGGCC CAAAAAAATG    4740
CCCTCTGCTG CTTGTGTATA CAACGTGTAC TATAGAGTTG TTGGAGAGAG CATATGGAAG    4800
ACTCTGGAGA CTCACAGCAA TAAGACAAAC ACTGTATTAA AAGTGTTGAA ACCAGATACC    4860
ACCTACCAGG TTAAAGTGCA GGTTCAGTGC CTGAGCAAGG TGCACAACAC CAATGACTTT    4920
GTGACCTTGA AACTCCAGA  GGGATTGCCA GACGCCCTC  AGAACCTCCA GCTGTCGCTC    4980
CACGGGGAAG AGGAAGGTGT GATTGTGGGC CACTGGAGCC CTCCCACCCA CACCCACGGC    5040
CTCATTCGCG AATACATTGT AGAGTATAGC AGGAGTGGTT CCAAGGTGTG GACTTCAGAA    5100
AGGGCTGCTA GTAACTTTAC AGAAATAAAG AACTTGTTGG TCAACACCCT GTACACCGTC    5160
AGAGTGGCTG CGGTGACGAG TCGTGGGATA GGAAACTGGA GCGATTCCAA ATCCATTACC    5220
ACCGTGAAAG GAAAAGCGAT CCCGCCACCA AATATCCACA TTGACAACTA CGATGAAAAT    5280
```

```
TCCCTGAGTT TTACCCTGAC CGTGGATGGG AACATCAAGG TGAATGGCTA TGTGGTGAAC      5340

CTTTTCTGGG CATTTGACAC CCACAAACAA GAGAAGAAAA CCATGAACTT CCAAGGGAGC      5400

TCAGTGTCCC ACAAAGTTGG CAATCTGACA GCACAGACGG CCTATGAGAT TTCCGCCTGG      5460

GCCAAGACTG ACTTGGGCGA TAGTCCTCTG TCATTTGAGC ATGTCACGAC CAGAGGGGTT      5520

CGCCCACCTG CTCCTAGCCT CAAGGCCAGG GCTATCAATC AGACTGCAGT GGAATGCACC      5580

TGGACAGGCC CCAGGAATGT GGTGTATGGC ATTTTCTATG CCACATCCTT CCTGGACCTC      5640

TACCGCAACC CAAGCAGCCT GACCACGCCG CTGCACAACG CAACCGTGCT CGTCGGTAAG      5700

GATGAGCAGT ATCTGTTTCT GGTCCGGGTG GTGATGCCCT ACCAAGGGCC GTCCTCGGAC      5760

TACGTGGTCG TGAAGATGAT CCCGGACAGC AGGCTTCCTC CCCGGCACCT GCATGCCGTT      5820

CACACCGGCA AGACCTCGGC CGTCATCAAG TGGGAGTCGC CCTACGACTC TCCTGACCAG      5880

GACCTGTTCT ATGCGATCGC AGTTAAAGAT CTGATACGAA AGACGGACCG GAGCTACAAA      5940

GTCAAGTCCC GCAACAGCAC CGTGGAGTAC ACCCTGAGCA AGCTGGAGCC CGGAGGGAAA      6000

TACCACGTCA TTGTGCAGCT GGGGAACATG AGCAAAGATG CCAGTGTGAA GATCACCACC      6060

GTTTCGTTAT CGGCACCCGA TGCCTTAAAA ATCATAACAG AAAATGACCA CGTCCTTCTC      6120

TTCTGGAAAA GTCTAGCTCT AAAGGAAAAG TATTTTAACG AAAGCAGGGG CTACGAGATA      6180

CACATGTTTG ATAGCGCCAT GAATATCACC GCATACCTTG GAATACTAC TGACAATTTC       6240

TTTAAAATTT CCAACCTGAA GATGGGTCAC AATTACACAT TCACGGTCCA GGCACGATGC      6300

CTTTGGGCA GCCAGATCTG CGGGGAGCCT GCCGTGCTAC TGTATGATGA GCTGGGGTCT       6360

GGTGGCGATG CGTCGGCGAT GCAGGCTGCC AGGTCTACTG ATGTCGCCGC CGTGGTGGTG      6420

CCCATCCTGT TTCTGATACT GCTGAGCCTG GGGGTCGGGT TTGCCATCCT GTACACGAAG      6480

CATCGGAGGC TGCAGAGCAG CTTCACCGCC TTCGCCAACA GCCACTACAG CTCCAGACTC      6540

GGCTCCGCCA TCTTCTCCTC TGGGGATGAC TTGGGGGAGG ATGATGAAGA TGCTCCTATG      6600

ATCACTGGAT TTCGGACGA CGTCCCCATG GTGATAGCC                              6639
```

( 2 ) INFORMATION FOR SEQ ID NO:2:

( i ) SEQUENCE CHARACTERISTICS:
        ( A ) LENGTH: 6961 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:
        ( A ) NAME/KEY: CDS
        ( B ) LOCATION: 178..6819
        ( D ) OTHER INFORMATION: /note="Identification Method: S"

( i x ) FEATURE:
        ( A ) NAME/KEY: sig_peptide
        ( B ) LOCATION: 178..261
        ( D ) OTHER INFORMATION: /note="Identification Method: S"

( i x ) FEATURE:
        ( A ) NAME/KEY: misc_feature
        ( B ) LOCATION: 262..6816
        ( D ) OTHER INFORMATION: /function="Nucleotides 262-6816
            encode the mature peptide"
        / note="Identification Method: S"

( x i ) SEQUENCE DESCRIPTION: SEQ ID NO:2:

```
CCGCGAGCCG CACACGTGAC GGCGCCGCGC CGCGCCGCGC CGCGCCGAGC GGGACCCAGC        60

GGCTGCCCGG AGCCCCGGGA GCGGCGCGCG CGCGGCCCCG GCCCCGCCGC TCGGCCGGCG       120
```

| | | | | | | | | | | |
|---|---|---|---|---|---|---|---|---|---|---|
| GCGCGCTGCA | CATTCTCTCC | TGGCGGCGGC | GCCACCTGCA | GCCGCGTTCG | CCCGAAC | | | | | 177 |
| ATG | GCG | ACA | CGG | AGC | AGC | AGG | AGG | GAG | TCG | CGA | CTC | CCC | TTC | CTA | TTC | 225 |
| Met | Ala | Thr | Arg | Ser | Ser | Arg | Arg | Glu | Ser | Arg | Leu | Pro | Phe | Leu | Phe | |
| 1 | | | | 5 | | | | | 10 | | | | | 15 | | |
| ACC | CTG | GTC | GCG | CTG | CTG | CCG | CCC | GGG | GCT | CTC | TGC | GAG | GTG | TGG | ACG | 273 |
| Thr | Leu | Val | Ala | Leu | Leu | Pro | Pro | Gly | Ala | Leu | Cys | Glu | Val | Trp | Thr | |
| | | | 20 | | | | | 25 | | | | | 30 | | | |
| CGG | ACA | CTG | CAC | GGC | GGC | CGC | GCG | CCC | TTA | CCC | CAG | GAG | CGG | GGC | TTC | 321 |
| Arg | Thr | Leu | His | Gly | Gly | Arg | Ala | Pro | Leu | Pro | Gln | Glu | Arg | Gly | Phe | |
| | | | 35 | | | | | 40 | | | | | 45 | | | |
| CGC | GTG | GTG | CAG | GGC | GAC | CCG | CGC | GAG | CTG | CGG | CTG | TGG | GAG | CGC | GGG | 369 |
| Arg | Val | Val | Gln | Gly | Asp | Pro | Arg | Glu | Leu | Arg | Leu | Trp | Glu | Arg | Gly | |
| | 50 | | | | | 55 | | | | | 60 | | | | | |
| GAT | GCC | AGG | GGG | GCG | AGC | CGG | GCG | GAC | GAG | AAG | CCG | CTC | CGG | AGG | AGA | 417 |
| Asp | Ala | Arg | Gly | Ala | Ser | Arg | Ala | Asp | Glu | Lys | Pro | Leu | Arg | Arg | Arg | |
| 65 | | | | | 70 | | | | | 75 | | | | | 80 | |
| CGG | AGC | GCT | GCC | CTG | CAG | CCC | GAG | CCC | ATC | AAG | GTG | TAC | GGA | CAG | GTC | 465 |
| Arg | Ser | Ala | Ala | Leu | Gln | Pro | Glu | Pro | Ile | Lys | Val | Tyr | Gly | Gln | Val | |
| | | | | 85 | | | | | 90 | | | | | 95 | | |
| AGC | CTC | AAT | GAT | TCC | CAC | AAT | CAG | ATG | GTG | GTG | CAC | TGG | GCC | GGA | GAG | 513 |
| Ser | Leu | Asn | Asp | Ser | His | Asn | Gln | Met | Val | Val | His | Trp | Ala | Gly | Glu | |
| | | | 100 | | | | | 105 | | | | | 110 | | | |
| AAA | AGC | AAC | GTG | ATC | GTG | GCC | TTG | GCC | CGG | GAC | AGC | CTG | GCG | TTG | GCC | 561 |
| Lys | Ser | Asn | Val | Ile | Val | Ala | Leu | Ala | Arg | Asp | Ser | Leu | Ala | Leu | Ala | |
| | | 115 | | | | | 120 | | | | | 125 | | | | |
| AGG | CCC | AGG | AGC | AGT | GAT | GTG | TAC | GTG | TCT | TAT | GAC | TAT | GGA | AAA | TCA | 609 |
| Arg | Pro | Arg | Ser | Ser | Asp | Val | Tyr | Val | Ser | Tyr | Asp | Tyr | Gly | Lys | Ser | |
| | 130 | | | | | 135 | | | | | 140 | | | | | |
| TTC | AAT | AAG | ATT | TCA | GAG | AAA | TTG | AAC | TTC | GGC | GCG | GGA | AAT | AAC | ACA | 657 |
| Phe | Asn | Lys | Ile | Ser | Glu | Lys | Leu | Asn | Phe | Gly | Ala | Gly | Asn | Asn | Thr | |
| 145 | | | | | 150 | | | | | 155 | | | | | 160 | |
| GAG | GCT | GTG | GTG | GCC | CAG | TTC | TAC | CAC | AGC | CCT | GCG | GAC | AAC | AAA | CGG | 705 |
| Glu | Ala | Val | Val | Ala | Gln | Phe | Tyr | His | Ser | Pro | Ala | Asp | Asn | Lys | Arg | |
| | | | | 165 | | | | | 170 | | | | | 175 | | |
| TAC | ATC | TTC | GCA | GAT | GCC | TAC | GCC | CAG | TAT | CTC | TGG | ATC | ACG | TTT | GAC | 753 |
| Tyr | Ile | Phe | Ala | Asp | Ala | Tyr | Ala | Gln | Tyr | Leu | Trp | Ile | Thr | Phe | Asp | |
| | | | 180 | | | | | 185 | | | | | 190 | | | |
| TTC | TGC | AAC | ACC | ATC | CAT | GGC | TTT | TCC | ATC | CCG | TTC | CGG | GCA | GCT | GAT | 801 |
| Phe | Cys | Asn | Thr | Ile | His | Gly | Phe | Ser | Ile | Pro | Phe | Arg | Ala | Ala | Asp | |
| | | 195 | | | | | 200 | | | | | 205 | | | | |
| CTC | CTA | CTC | CAC | AGT | AAG | GCC | TCC | AAC | CTT | CTC | CTG | GGC | TTC | GAC | AGG | 849 |
| Leu | Leu | Leu | His | Ser | Lys | Ala | Ser | Asn | Leu | Leu | Leu | Gly | Phe | Asp | Arg | |
| | 210 | | | | | 215 | | | | | 220 | | | | | |
| TCT | CAC | CCC | AAC | AAG | CAG | CTG | TGG | AAG | TCG | GAT | GAT | TTT | GGC | CAG | ACC | 897 |
| Ser | His | Pro | Asn | Lys | Gln | Leu | Trp | Lys | Ser | Asp | Asp | Phe | Gly | Gln | Thr | |
| 225 | | | | | 230 | | | | | 235 | | | | | 240 | |
| TGG | ATC | ATG | ATT | CAA | GAA | CAC | GTG | AAG | TCC | TTT | TCT | TGG | GGA | ATT | GAT | 945 |
| Trp | Ile | Met | Ile | Gln | Glu | His | Val | Lys | Ser | Phe | Ser | Trp | Gly | Ile | Asp | |
| | | | | 245 | | | | | 250 | | | | | 255 | | |
| CCC | TAT | GAC | AAA | CCA | AAC | ACC | ATC | TAC | ATC | GAA | CGG | CAC | GAA | CCT | TCT | 993 |
| Pro | Tyr | Asp | Lys | Pro | Asn | Thr | Ile | Tyr | Ile | Glu | Arg | His | Glu | Pro | Ser | |
| | | | 260 | | | | | 265 | | | | | 270 | | | |
| GGC | TAC | TCC | ACG | GTT | TTC | CGA | AGT | ACA | GAC | TTC | TTC | CAG | TCC | CGG | GAA | 1041 |
| Gly | Tyr | Ser | Thr | Val | Phe | Arg | Ser | Thr | Asp | Phe | Phe | Gln | Ser | Arg | Glu | |
| | | 275 | | | | | 280 | | | | | 285 | | | | |
| AAC | CAG | GAA | GTG | ATC | TTG | GAG | GAA | GTG | AGA | GAC | TTT | CAG | CTT | CGG | GAC | 1089 |
| Asn | Gln | Glu | Val | Ile | Leu | Glu | Glu | Val | Arg | Asp | Phe | Gln | Leu | Arg | Asp | |
| | 290 | | | | | 295 | | | | | 300 | | | | | |
| AAG | TAC | ATG | TTT | GCT | ACA | AAG | GTG | GTG | CAT | CTC | TTG | GGC | AGT | CCA | CTG | 1137 |

| | | | | | | | | | | | | | | | |
|---|---|---|---|---|---|---|---|---|---|---|---|---|---|---|---|
| Lys | Tyr | Met | Phe | Ala | Thr | Lys | Val | Val | His | Leu | Leu | Gly | Ser | Pro | Leu |
| 305 | | | | | 310 | | | | | 315 | | | | | 320 |

| | | | | | | | | | | | | | | | | |
|---|---|---|---|---|---|---|---|---|---|---|---|---|---|---|---|---|
| CAG | TCT | TCT | GTC | CAG | CTC | TGG | GTC | TCC | TTT | GGC | CGG | AAG | CCC | ATG | CGG | 1185 |
| Gln | Ser | Ser | Val | Gln | Leu | Trp | Val | Ser | Phe | Gly | Arg | Lys | Pro | Met | Arg | |
| | | | | 325 | | | | | 330 | | | | | 335 | | |

| | | | | | | | | | | | | | | | | |
|---|---|---|---|---|---|---|---|---|---|---|---|---|---|---|---|---|
| GCC | GCC | CAG | TTT | GTT | ACA | AGA | CAT | CCT | ATC | AAC | GAA | TAT | TAC | ATC | GCG | 1233 |
| Ala | Ala | Gln | Phe | Val | Thr | Arg | His | Pro | Ile | Asn | Glu | Tyr | Tyr | Ile | Ala | |
| | | | 340 | | | | | 345 | | | | | 350 | | | |

| | | | | | | | | | | | | | | | | |
|---|---|---|---|---|---|---|---|---|---|---|---|---|---|---|---|---|
| GAT | GCC | TCG | GAG | GAC | CAG | GTG | TTT | GTG | TGT | GTC | AGT | CAC | AGC | AAC | AAC | 1281 |
| Asp | Ala | Ser | Glu | Asp | Gln | Val | Phe | Val | Cys | Val | Ser | His | Ser | Asn | Asn | |
| | | 355 | | | | | 360 | | | | | 365 | | | | |

| | | | | | | | | | | | | | | | | |
|---|---|---|---|---|---|---|---|---|---|---|---|---|---|---|---|---|
| CGC | ACC | AAC | CTC | TAC | ATC | TCG | GAG | GCA | GAG | GGC | TTG | AAG | TTC | TCT | CTG | 1329 |
| Arg | Thr | Asn | Leu | Tyr | Ile | Ser | Glu | Ala | Glu | Gly | Leu | Lys | Phe | Ser | Leu | |
| | 370 | | | | | 375 | | | | | 380 | | | | | |

| | | | | | | | | | | | | | | | | |
|---|---|---|---|---|---|---|---|---|---|---|---|---|---|---|---|---|
| TCC | CTG | GAG | AAC | GTG | CTC | TAC | TAC | ACC | CCG | GGA | GGG | GCC | GGC | AGT | GAC | 1377 |
| Ser | Leu | Glu | Asn | Val | Leu | Tyr | Tyr | Thr | Pro | Gly | Gly | Ala | Gly | Ser | Asp | |
| 385 | | | | | 390 | | | | | 395 | | | | | 400 | |

| | | | | | | | | | | | | | | | | |
|---|---|---|---|---|---|---|---|---|---|---|---|---|---|---|---|---|
| ACC | TTG | GTG | AGG | TAC | TTT | GCA | AAT | GAA | CCG | TTT | GCT | GAC | TTC | CAT | CGT | 1425 |
| Thr | Leu | Val | Arg | Tyr | Phe | Ala | Asn | Glu | Pro | Phe | Ala | Asp | Phe | His | Arg | |
| | | | | 405 | | | | | 410 | | | | | 415 | | |

| | | | | | | | | | | | | | | | | |
|---|---|---|---|---|---|---|---|---|---|---|---|---|---|---|---|---|
| GTG | GAA | GGG | TTG | CAG | GGA | GTC | TAC | ATT | GCT | ACT | CTG | ATT | AAT | GGT | TCT | 1473 |
| Val | Glu | Gly | Leu | Gln | Gly | Val | Tyr | Ile | Ala | Thr | Leu | Ile | Asn | Gly | Ser | |
| | | | 420 | | | | | 425 | | | | | 430 | | | |

| | | | | | | | | | | | | | | | | |
|---|---|---|---|---|---|---|---|---|---|---|---|---|---|---|---|---|
| ATG | AAT | GAG | GAG | AAC | ATG | AGA | TCT | GTC | ATC | ACC | TTT | GAC | AAA | GGG | GGC | 1521 |
| Met | Asn | Glu | Glu | Asn | Met | Arg | Ser | Val | Ile | Thr | Phe | Asp | Lys | Gly | Gly | |
| | | 435 | | | | | 440 | | | | | 445 | | | | |

| | | | | | | | | | | | | | | | | |
|---|---|---|---|---|---|---|---|---|---|---|---|---|---|---|---|---|
| ACC | TGG | GAA | TTT | CTG | CAG | GCT | CCA | GCC | TTC | ACG | GGG | TAT | GGA | GAG | AAA | 1569 |
| Thr | Trp | Glu | Phe | Leu | Gln | Ala | Pro | Ala | Phe | Thr | Gly | Tyr | Gly | Glu | Lys | |
| | 450 | | | | | 455 | | | | | 460 | | | | | |

| | | | | | | | | | | | | | | | | |
|---|---|---|---|---|---|---|---|---|---|---|---|---|---|---|---|---|
| ATC | AAC | TGT | GAG | CTG | TCC | GAG | GGC | TGT | TCC | CTC | CAC | CTG | GCC | CAG | CGC | 1617 |
| Ile | Asn | Cys | Glu | Leu | Ser | Glu | Gly | Cys | Ser | Leu | His | Leu | Ala | Gln | Arg | |
| 465 | | | | | 470 | | | | | 475 | | | | | 480 | |

| | | | | | | | | | | | | | | | | |
|---|---|---|---|---|---|---|---|---|---|---|---|---|---|---|---|---|
| CTC | AGC | CAG | CTG | CTC | AAC | CTC | CAG | CTC | CGG | AGG | ATG | CCC | ATC | CTG | TCC | 1665 |
| Leu | Ser | Gln | Leu | Leu | Asn | Leu | Gln | Leu | Arg | Arg | Met | Pro | Ile | Leu | Ser | |
| | | | | 485 | | | | | 490 | | | | | 495 | | |

| | | | | | | | | | | | | | | | | |
|---|---|---|---|---|---|---|---|---|---|---|---|---|---|---|---|---|
| AAG | GAG | TCG | GCG | CCT | GGC | CTC | ATC | ATT | GCC | ACG | GGC | TCA | GTG | GGA | AAG | 1713 |
| Lys | Glu | Ser | Ala | Pro | Gly | Leu | Ile | Ile | Ala | Thr | Gly | Ser | Val | Gly | Lys | |
| | | | | 500 | | | | | 505 | | | | | 510 | | |

| | | | | | | | | | | | | | | | | |
|---|---|---|---|---|---|---|---|---|---|---|---|---|---|---|---|---|
| AAC | TTG | GCT | AGC | AAG | ACA | AAC | GTG | TAC | ATC | TCT | AGC | AGT | GCT | GGA | GCC | 1761 |
| Asn | Leu | Ala | Ser | Lys | Thr | Asn | Val | Tyr | Ile | Ser | Ser | Ser | Ala | Gly | Ala | |
| | | | 515 | | | | | 520 | | | | | 525 | | | |

| | | | | | | | | | | | | | | | | |
|---|---|---|---|---|---|---|---|---|---|---|---|---|---|---|---|---|
| AGG | TGG | CGA | GAG | GCA | CTT | CCT | GGA | CCT | CAC | TAC | TAT | ACA | TGG | GGA | GAC | 1809 |
| Arg | Trp | Arg | Glu | Ala | Leu | Pro | Gly | Pro | His | Tyr | Tyr | Thr | Trp | Gly | Asp | |
| | 530 | | | | | 535 | | | | | 540 | | | | | |

| | | | | | | | | | | | | | | | | |
|---|---|---|---|---|---|---|---|---|---|---|---|---|---|---|---|---|
| CAT | GGC | GGC | ATC | ATC | ATG | GCC | ATT | GCC | CAA | GGC | ATG | GAA | ACC | AAC | GAA | 1857 |
| His | Gly | Gly | Ile | Ile | Met | Ala | Ile | Ala | Gln | Gly | Met | Glu | Thr | Asn | Glu | |
| 545 | | | | | 550 | | | | | 555 | | | | | 560 | |

| | | | | | | | | | | | | | | | | |
|---|---|---|---|---|---|---|---|---|---|---|---|---|---|---|---|---|
| CTG | AAG | TAC | AGT | ACC | AAC | GAA | GGG | GAG | ACC | TGG | AAA | GCC | TTC | ACC | TTC | 1905 |
| Leu | Lys | Tyr | Ser | Thr | Asn | Glu | Gly | Glu | Thr | Trp | Lys | Ala | Phe | Thr | Phe | |
| | | | | 565 | | | | | 570 | | | | | 575 | | |

| | | | | | | | | | | | | | | | | |
|---|---|---|---|---|---|---|---|---|---|---|---|---|---|---|---|---|
| TCT | GAG | AAG | CCC | GTG | TTT | GTG | TAT | GGG | CTC | CTC | ACG | GAA | CCC | GGC | GAG | 1953 |
| Ser | Glu | Lys | Pro | Val | Phe | Val | Tyr | Gly | Leu | Leu | Thr | Glu | Pro | Gly | Glu | |
| | | | 580 | | | | | 585 | | | | | 590 | | | |

| | | | | | | | | | | | | | | | | |
|---|---|---|---|---|---|---|---|---|---|---|---|---|---|---|---|---|
| AAG | AGC | ACG | GTC | TTC | ACC | ATC | TTT | GGC | TCC | AAC | AAG | GAG | AAC | GTG | CAC | 2001 |
| Lys | Ser | Thr | Val | Phe | Thr | Ile | Phe | Gly | Ser | Asn | Lys | Glu | Asn | Val | His | |
| | | 595 | | | | | 600 | | | | | 605 | | | | |

| | | | | | | | | | | | | | | | | |
|---|---|---|---|---|---|---|---|---|---|---|---|---|---|---|---|---|
| AGC | TGG | CTC | ATC | CTC | CAG | GTC | AAT | GCC | ACA | GAC | GCC | CTG | GGG | GTT | CCT | 2049 |
| Ser | Trp | Leu | Ile | Leu | Gln | Val | Asn | Ala | Thr | Asp | Ala | Leu | Gly | Val | Pro | |
| | 610 | | | | | 615 | | | | | 620 | | | | | |

| | | | | | | | | | | | | | | | | |
|---|---|---|---|---|---|---|---|---|---|---|---|---|---|---|---|---|
| TGC | ACA | GAG | AAC | GAC | TAC | AAG | CTC | TGG | TCA | CCA | TCT | GAT | GAG | CGG | GGG | 2097 |

| | | | | | | | | | | | | | | | |
|---|---|---|---|---|---|---|---|---|---|---|---|---|---|---|---|
| Cys | Thr | Glu | Asn | Asp | Tyr | Lys | Leu | Trp | Ser | Pro | Ser | Asp | Glu | Arg | Gly |
| 625 | | | | | 630 | | | | | 635 | | | | | 640 |

| AAT | GAG | TGT | TTG | CTT | GGA | CAC | AAG | ACT | GTT | TTC | AAA | CGG | AGG | ACC | CCG | 2145 |
|---|---|---|---|---|---|---|---|---|---|---|---|---|---|---|---|---|
| Asn | Glu | Cys | Leu | Leu | Gly | His | Lys | Thr | Val | Phe | Lys | Arg | Arg | Thr | Pro | |
| | | | | 645 | | | | | 650 | | | | | 655 | | |

| CAC | GCC | ACA | TGC | TTT | AAC | GGA | GAA | GAC | TTT | GAC | AGG | CCG | GTG | GTT | GTG | 2193 |
|---|---|---|---|---|---|---|---|---|---|---|---|---|---|---|---|---|
| His | Ala | Thr | Cys | Phe | Asn | Gly | Glu | Asp | Phe | Asp | Arg | Pro | Val | Val | Val | |
| | | | 660 | | | | | 665 | | | | | 670 | | | |

| TCC | AAC | TGC | TCC | TGC | ACC | CGG | GAG | GAC | TAT | GAG | TGT | GAC | TTT | GGC | TTC | 2241 |
|---|---|---|---|---|---|---|---|---|---|---|---|---|---|---|---|---|
| Ser | Asn | Cys | Ser | Cys | Thr | Arg | Glu | Asp | Tyr | Glu | Cys | Asp | Phe | Gly | Phe | |
| | | 675 | | | | | 680 | | | | | 685 | | | | |

| CGG | ATG | AGT | GAA | GAC | TTG | GCA | TTA | GAG | GTG | TGT | GTT | CCA | GAT | CCA | GGA | 2289 |
|---|---|---|---|---|---|---|---|---|---|---|---|---|---|---|---|---|
| Arg | Met | Ser | Glu | Asp | Leu | Ala | Leu | Glu | Val | Cys | Val | Pro | Asp | Pro | Gly | |
| | 690 | | | | | 695 | | | | | 700 | | | | | |

| TTT | TCT | GGA | AAG | TCC | TCC | CCT | CCA | GTG | CCT | TGT | CCC | GTG | GGC | TCT | ACG | 2337 |
|---|---|---|---|---|---|---|---|---|---|---|---|---|---|---|---|---|
| Phe | Ser | Gly | Lys | Ser | Ser | Pro | Pro | Val | Pro | Cys | Pro | Val | Gly | Ser | Thr | |
| 705 | | | | | 710 | | | | | 715 | | | | | 720 | |

| TAC | AGG | CGA | TCA | AGA | GGC | TAC | CGG | AAG | ATT | TCT | GGG | GAC | ACC | TGT | AGT | 2385 |
|---|---|---|---|---|---|---|---|---|---|---|---|---|---|---|---|---|
| Tyr | Arg | Arg | Ser | Arg | Gly | Tyr | Arg | Lys | Ile | Ser | Gly | Asp | Thr | Cys | Ser | |
| | | | | 725 | | | | | 730 | | | | | 735 | | |

| GGA | GGA | GAT | GTT | GAG | GCA | CGG | CTA | GAA | GGA | GAG | CTG | GTC | CCC | TGT | CCC | 2433 |
|---|---|---|---|---|---|---|---|---|---|---|---|---|---|---|---|---|
| Gly | Gly | Asp | Val | Glu | Ala | Arg | Leu | Glu | Gly | Glu | Leu | Val | Pro | Cys | Pro | |
| | | | 740 | | | | | 745 | | | | | 750 | | | |

| CTG | GCA | GAA | GAG | AAC | GAG | TTC | ATC | CTG | TAC | GCC | ACG | CGC | AAG | TCC | ATC | 2481 |
|---|---|---|---|---|---|---|---|---|---|---|---|---|---|---|---|---|
| Leu | Ala | Glu | Glu | Asn | Glu | Phe | Ile | Leu | Tyr | Ala | Thr | Arg | Lys | Ser | Ile | |
| | | | 755 | | | | | 760 | | | | | 765 | | | |

| CAC | CGC | TAT | GAC | CTG | GCT | TCC | GGA | ACC | ACG | GAG | CAG | TTG | CCC | CTC | ACT | 2529 |
|---|---|---|---|---|---|---|---|---|---|---|---|---|---|---|---|---|
| His | Arg | Tyr | Asp | Leu | Ala | Ser | Gly | Thr | Thr | Glu | Gln | Leu | Pro | Leu | Thr | |
| | 770 | | | | | 775 | | | | | 780 | | | | | |

| GGG | TTG | CGG | GCA | GCA | GTG | GCC | CTG | GAC | TTT | GAC | TAT | GAG | CAC | AAC | TGC | 2577 |
|---|---|---|---|---|---|---|---|---|---|---|---|---|---|---|---|---|
| Gly | Leu | Arg | Ala | Ala | Val | Ala | Leu | Asp | Phe | Asp | Tyr | Glu | His | Asn | Cys | |
| 785 | | | | | 790 | | | | | 795 | | | | | 800 | |

| CTG | TAT | TGG | TCT | GAC | CTG | GCC | TTG | GAC | GTC | ATC | CAG | CGC | CTC | TGT | TTG | 2625 |
|---|---|---|---|---|---|---|---|---|---|---|---|---|---|---|---|---|
| Leu | Tyr | Trp | Ser | Asp | Leu | Ala | Leu | Asp | Val | Ile | Gln | Arg | Leu | Cys | Leu | |
| | | | | 805 | | | | | 810 | | | | | 815 | | |

| AAC | GGG | AGT | ACA | GGA | CAA | GAG | GTG | ATC | ATC | AAC | TCT | GAC | CTG | GAG | ACG | 2673 |
|---|---|---|---|---|---|---|---|---|---|---|---|---|---|---|---|---|
| Asn | Gly | Ser | Thr | Gly | Gln | Glu | Val | Ile | Ile | Asn | Ser | Asp | Leu | Glu | Thr | |
| | | | 820 | | | | | 825 | | | | | 830 | | | |

| GTA | GAA | GCT | TTG | GCT | TTT | GAA | CCC | CTC | AGC | CAA | TTA | CTT | TAC | TGG | GTG | 2721 |
|---|---|---|---|---|---|---|---|---|---|---|---|---|---|---|---|---|
| Val | Glu | Ala | Leu | Ala | Phe | Glu | Pro | Leu | Ser | Gln | Leu | Leu | Tyr | Trp | Val | |
| | | | 835 | | | | | 840 | | | | | 845 | | | |

| GAC | GCA | GGC | TTT | AAA | AAG | ATC | GAG | GTA | GCC | AAT | CCA | GAT | GGT | GAC | TTC | 2769 |
|---|---|---|---|---|---|---|---|---|---|---|---|---|---|---|---|---|
| Asp | Ala | Gly | Phe | Lys | Lys | Ile | Glu | Val | Ala | Asn | Pro | Asp | Gly | Asp | Phe | |
| | 850 | | | | | 855 | | | | | 860 | | | | | |

| CGA | CTC | ACC | GTC | GTC | AAT | TCC | TCG | GTG | CTG | GAT | CGG | CCC | CGG | GCC | CTG | 2817 |
|---|---|---|---|---|---|---|---|---|---|---|---|---|---|---|---|---|
| Arg | Leu | Thr | Val | Val | Asn | Ser | Ser | Val | Leu | Asp | Arg | Pro | Arg | Ala | Leu | |
| 865 | | | | | 870 | | | | | 875 | | | | | 880 | |

| GTC | CTT | GTG | CCC | CAA | GAA | GGG | ATC | ATG | TTC | TGG | ACC | GAC | TGG | GGA | GAC | 2865 |
|---|---|---|---|---|---|---|---|---|---|---|---|---|---|---|---|---|
| Val | Leu | Val | Pro | Gln | Glu | Gly | Ile | Met | Phe | Trp | Thr | Asp | Trp | Gly | Asp | |
| | | | | 885 | | | | | 890 | | | | | 895 | | |

| CTG | AAG | CCT | GGG | ATT | TAT | CGG | AGC | AAC | ATG | GAC | GGA | TCT | GCC | GCC | TAT | 2913 |
|---|---|---|---|---|---|---|---|---|---|---|---|---|---|---|---|---|
| Leu | Lys | Pro | Gly | Ile | Tyr | Arg | Ser | Asn | Met | Asp | Gly | Ser | Ala | Ala | Tyr | |
| | | | 900 | | | | | 905 | | | | | 910 | | | |

| CGC | CTC | GTG | TCG | GAG | GAT | GTG | AAG | TGG | CCC | AAT | GGC | ATT | TCC | GTG | GAC | 2961 |
|---|---|---|---|---|---|---|---|---|---|---|---|---|---|---|---|---|
| Arg | Leu | Val | Ser | Glu | Asp | Val | Lys | Trp | Pro | Asn | Gly | Ile | Ser | Val | Asp | |
| | | 915 | | | | | 920 | | | | | 925 | | | | |

| GAT | CAG | TGG | ATC | TAC | TGG | ACG | GAT | GCC | TAC | CTG | GAC | TGC | ATT | GAG | CGC | 3009 |
|---|---|---|---|---|---|---|---|---|---|---|---|---|---|---|---|---|
| Asp | Gln | Trp | Ile | Tyr | Trp | Thr | Asp | Ala | Tyr | Leu | Asp | Cys | Ile | Glu | Arg | |
| | 930 | | | | | 935 | | | | | 940 | | | | | |

| ATC | ACG | TTC | AGC | GGC | CAG | CAG | CGC | TCC | GTC | ATC | CTG | GAC | AGA | CTC | CCG | 3057 |

| | | | | | | | | | | | | | | | | |
|---|---|---|---|---|---|---|---|---|---|---|---|---|---|---|---|---|
| Ile | Thr | Phe | Ser | Gly | Gln | Gln | Arg | Ser | Val | Ile | Leu | Asp | Arg | Leu | Pro | |
| 945 | | | | | 950 | | | | | 955 | | | | | 960 | |

| CAC | CCC | TAT | GCC | ATT | GCT | GTC | TTT | AAG | AAT | GAG | ATT | TAC | TGG | GAT | GAC | 3105 |
|---|---|---|---|---|---|---|---|---|---|---|---|---|---|---|---|---|
| His | Pro | Tyr | Ala | Ile | Ala | Val | Phe | Lys | Asn | Glu | Ile | Tyr | Trp | Asp | Asp | |
| | | | | 965 | | | | | 970 | | | | | 975 | | |

| TGG | TCA | CAG | CTC | AGC | ATA | TTC | CGA | GCT | TCT | AAG | TAC | AGC | GGG | TCC | CAG | 3153 |
|---|---|---|---|---|---|---|---|---|---|---|---|---|---|---|---|---|
| Trp | Ser | Gln | Leu | Ser | Ile | Phe | Arg | Ala | Ser | Lys | Tyr | Ser | Gly | Ser | Gln | |
| | | | | 980 | | | | | 985 | | | | | 990 | | |

| ATG | GAG | ATT | CTG | GCC | AGC | CAG | CTC | ACG | GGG | CTG | ATG | GAC | ATG | AAG | ATC | 3201 |
|---|---|---|---|---|---|---|---|---|---|---|---|---|---|---|---|---|
| Met | Glu | Ile | Leu | Ala | Ser | Gln | Leu | Thr | Gly | Leu | Met | Asp | Met | Lys | Ile | |
| | | | 995 | | | | | 1000 | | | | | 1005 | | | |

| TTC | TAC | AAG | GGG | AAG | AAC | ACA | GGA | AGC | AAT | GCG | TGT | GTA | CCC | AGG | CCG | 3249 |
|---|---|---|---|---|---|---|---|---|---|---|---|---|---|---|---|---|
| Phe | Tyr | Lys | Gly | Lys | Asn | Thr | Gly | Ser | Asn | Ala | Cys | Val | Pro | Arg | Pro | |
| 1010 | | | | | 1015 | | | | | 1020 | | | | | | |

| TGC | AGC | CTG | CTG | TGC | CTG | CCC | AGA | GCC | AAC | AAC | AGC | AAA | AGC | TGC | AGG | 3297 |
|---|---|---|---|---|---|---|---|---|---|---|---|---|---|---|---|---|
| Cys | Ser | Leu | Leu | Cys | Leu | Pro | Arg | Ala | Asn | Asn | Ser | Lys | Ser | Cys | Arg | |
| 1025 | | | | | 1030 | | | | | 1035 | | | | | 1040 | |

| TGT | CCA | GAT | GGC | GTG | GCC | AGC | AGT | GTC | CTC | CCT | TCC | GGG | GAC | CTG | ATG | 3345 |
|---|---|---|---|---|---|---|---|---|---|---|---|---|---|---|---|---|
| Cys | Pro | Asp | Gly | Val | Ala | Ser | Ser | Val | Leu | Pro | Ser | Gly | Asp | Leu | Met | |
| | | | | 1045 | | | | | 1050 | | | | | 1055 | | |

| TGT | GAC | TGC | CCT | AAG | GGC | TAC | GAG | CTG | AAG | AAC | AAC | ACG | TGT | GTC | AAA | 3393 |
|---|---|---|---|---|---|---|---|---|---|---|---|---|---|---|---|---|
| Cys | Asp | Cys | Pro | Lys | Gly | Tyr | Glu | Leu | Lys | Asn | Asn | Thr | Cys | Val | Lys | |
| | | | 1060 | | | | | 1065 | | | | | 1070 | | | |

| GAA | GAA | GAC | ACC | TGT | CTG | CGC | AAC | CAG | TAC | CGC | TGC | AGC | AAC | GGG | AAC | 3441 |
|---|---|---|---|---|---|---|---|---|---|---|---|---|---|---|---|---|
| Glu | Glu | Asp | Thr | Cys | Leu | Arg | Asn | Gln | Tyr | Arg | Cys | Ser | Asn | Gly | Asn | |
| | | 1075 | | | | | 1080 | | | | | 1085 | | | | |

| TGC | ATC | AAC | AGC | ATC | TGG | TGG | TGC | GAT | TTC | GAC | AAC | GAC | TGC | GGA | GAC | 3489 |
|---|---|---|---|---|---|---|---|---|---|---|---|---|---|---|---|---|
| Cys | Ile | Asn | Ser | Ile | Trp | Trp | Cys | Asp | Phe | Asp | Asn | Asp | Cys | Gly | Asp | |
| | | 1090 | | | | | 1095 | | | | | 1100 | | | | |

| ATG | AGC | GAC | GAG | AAG | AAC | TGC | CCT | ACC | ACC | ATC | TGC | GAC | CTG | GAC | ACC | 3537 |
|---|---|---|---|---|---|---|---|---|---|---|---|---|---|---|---|---|
| Met | Ser | Asp | Glu | Lys | Asn | Cys | Pro | Thr | Thr | Ile | Cys | Asp | Leu | Asp | Thr | |
| 1105 | | | | | 1110 | | | | | 1115 | | | | | 1120 | |

| CAG | TTC | CGT | TGC | CAG | GAG | TCT | GGG | ACG | TGC | ATC | CCG | CTC | TCC | TAC | AAA | 3585 |
|---|---|---|---|---|---|---|---|---|---|---|---|---|---|---|---|---|
| Gln | Phe | Arg | Cys | Gln | Glu | Ser | Gly | Thr | Cys | Ile | Pro | Leu | Ser | Tyr | Lys | |
| | | | | 1125 | | | | | 1130 | | | | | 1135 | | |

| TGT | GAC | CTC | GAG | GAT | GAC | TGT | GGG | GAC | AAC | AGT | GAC | GAA | AGG | CAC | TGT | 3633 |
|---|---|---|---|---|---|---|---|---|---|---|---|---|---|---|---|---|
| Cys | Asp | Leu | Glu | Asp | Asp | Cys | Gly | Asp | Asn | Ser | Asp | Glu | Arg | His | Cys | |
| | | | | 1140 | | | | | 1145 | | | | | 1150 | | |

| GAA | ATG | CAC | CAG | TGC | CGG | AGC | GAC | GAA | TAC | AAC | TGC | AGC | TCG | GGC | ATG | 3681 |
|---|---|---|---|---|---|---|---|---|---|---|---|---|---|---|---|---|
| Glu | Met | His | Gln | Cys | Arg | Ser | Asp | Glu | Tyr | Asn | Cys | Ser | Ser | Gly | Met | |
| | | | 1155 | | | | | 1160 | | | | | 1165 | | | |

| TGC | ATC | CGC | TCC | TCC | TGG | GTG | TGC | GAC | GGG | GAC | AAC | GAC | TGC | AGG | GAC | 3729 |
|---|---|---|---|---|---|---|---|---|---|---|---|---|---|---|---|---|
| Cys | Ile | Arg | Ser | Ser | Trp | Val | Cys | Asp | Gly | Asp | Asn | Asp | Cys | Arg | Asp | |
| | | 1170 | | | | | 1175 | | | | | 1180 | | | | |

| TGG | TCC | GAC | GAG | GCC | AAC | TGC | ACA | GCC | ATC | TAT | CAC | ACC | TGT | GAG | GCC | 3777 |
|---|---|---|---|---|---|---|---|---|---|---|---|---|---|---|---|---|
| Trp | Ser | Asp | Glu | Ala | Asn | Cys | Thr | Ala | Ile | Tyr | His | Thr | Cys | Glu | Ala | |
| 1185 | | | | | 1190 | | | | | 1195 | | | | | 1200 | |

| TCC | AAC | TTC | CAG | TGC | CGC | AAC | GGG | CAC | TGC | ATC | CCC | CAG | CGG | TGG | GCG | 3825 |
|---|---|---|---|---|---|---|---|---|---|---|---|---|---|---|---|---|
| Ser | Asn | Phe | Gln | Cys | Arg | Asn | Gly | His | Cys | Ile | Pro | Gln | Arg | Trp | Ala | |
| | | | | 1205 | | | | | 1210 | | | | | 1215 | | |

| TGT | GAC | GGC | GAC | GCC | GAC | TGC | CAG | GAT | GGC | TCT | GAT | GAG | GAT | CCA | GCC | 3873 |
|---|---|---|---|---|---|---|---|---|---|---|---|---|---|---|---|---|
| Cys | Asp | Gly | Asp | Ala | Asp | Cys | Gln | Asp | Gly | Ser | Asp | Glu | Asp | Pro | Ala | |
| | | | | 1220 | | | | | 1225 | | | | | 1230 | | |

| AAC | TGT | GAG | AAG | AAG | TGC | AAC | GGC | TTC | CGC | TGC | CCG | AAC | GGC | ACC | TGC | 3921 |
|---|---|---|---|---|---|---|---|---|---|---|---|---|---|---|---|---|
| Asn | Cys | Glu | Lys | Lys | Cys | Asn | Gly | Phe | Arg | Cys | Pro | Asn | Gly | Thr | Cys | |
| | | | 1235 | | | | | 1240 | | | | | 1245 | | | |

| ATT | CCC | TCC | ACC | AAG | CAC | TGT | GAC | GGC | CTG | CAC | GAT | TGC | TCG | GAC | GGC | 3969 |
|---|---|---|---|---|---|---|---|---|---|---|---|---|---|---|---|---|
| Ile | Pro | Ser | Thr | Lys | His | Cys | Asp | Gly | Leu | His | Asp | Cys | Ser | Asp | Gly | |
| | | | | 1250 | | | | | 1255 | | | | | 1260 | | |

| TCC | GAC | GAG | CAG | CAC | TGC | GAG | CCC | CTG | TGT | ACA | CGG | TTC | ATG | GAC | TTC | 4017 |

| | | | | | | | | | | | | | | | |
|---|---|---|---|---|---|---|---|---|---|---|---|---|---|---|---|
| Ser | Asp | Glu | Gln | His | Cys | Glu | Pro | Leu | Cys | Thr | Arg | Phe | Met | Asp | Phe |
| 1265 | | | | 1270 | | | | 1275 | | | | | | 1280 | |

```
GTG TGT AAG AAC CGC CAG CAG TGC CTC TTC CAC TCC ATG GTG TGC GAT          4065
Val Cys Lys Asn Arg Gln Gln Cys Leu Phe His Ser Met Val Cys Asp
            1285                1290                1295

GGG ATC ATC CAG TGC CGT GAC GGC TCC GAC GAG GAC CCA GCC TTT GCA          4113
Gly Ile Ile Gln Cys Arg Asp Gly Ser Asp Glu Asp Pro Ala Phe Ala
        1300                1305                1310

GGA TGC TCC CGA GAC CCC GAG TTC CAC AAG GTG TGC GAT GAG TTC GGC          4161
Gly Cys Ser Arg Asp Pro Glu Phe His Lys Val Cys Asp Glu Phe Gly
        1315                1320                1325

TTC CAG TGT CAG AAC GGC GTG TGC ATC AGC TTG ATC TGG AAG TGC GAC          4209
Phe Gln Cys Gln Asn Gly Val Cys Ile Ser Leu Ile Trp Lys Cys Asp
        1330                1335                1340

GGG ATG GAT GAC TGC GGG GAC TAC TCC GAC GAG GCC AAC TGT GAA AAC          4257
Gly Met Asp Asp Cys Gly Asp Tyr Ser Asp Glu Ala Asn Cys Glu Asn
1345                1350                1355                1360

CCC ACA GAA GCC CCC AAC TGC TCC CGC TAC TTC CAG TTC CGG TGT GAC          4305
Pro Thr Glu Ala Pro Asn Cys Ser Arg Tyr Phe Gln Phe Arg Cys Asp
                1365                1370                1375

AAT GGC CAC TGC ATC CCC AAC AGG TGG AAG TGT GAC AGG GAG AAT GAC          4353
Asn Gly His Cys Ile Pro Asn Arg Trp Lys Cys Asp Arg Glu Asn Asp
            1380                1385                1390

TGT GGG GAC TGG TCC GAC GAG AAG GAC TGT GGA GAT TCA CAT GTA CTT          4401
Cys Gly Asp Trp Ser Asp Glu Lys Asp Cys Gly Asp Ser His Val Leu
        1395                1400                1405

CCG TCT ACG ACT CCT GCA CCC TCC ACG TGT CTG CCC AAT TAC TAC CGC          4449
Pro Ser Thr Thr Pro Ala Pro Ser Thr Cys Leu Pro Asn Tyr Tyr Arg
        1410                1415                1420

TGC GGC GGG GGG GCC TGC GTG ATA GAC ACG TGG GTT TGT GAC GGG TAC          4497
Cys Gly Gly Gly Ala Cys Val Ile Asp Thr Trp Val Cys Asp Gly Tyr
1425                1430                1435                1440

CGA GAT TGC GCA GAT GGA TCC GAC GAG GAA GCC TGC CCC TCG CTC CCC          4545
Arg Asp Cys Ala Asp Gly Ser Asp Glu Glu Ala Cys Pro Ser Leu Pro
        1445                1450                1455

AAT GTC ACT GCC ACC TCC TCC CCC TCC CAG CCT GGA CGA TGC GAC CGA          4593
Asn Val Thr Ala Thr Ser Ser Pro Ser Gln Pro Gly Arg Cys Asp Arg
        1460                1465                1470

TTT GAG TTT GAG TGC CAC CAG CCA AAG AAG TGC ATC CCT AAC TGG AGA          4641
Phe Glu Phe Glu Cys His Gln Pro Lys Lys Cys Ile Pro Asn Trp Arg
        1475                1480                1485

CGC TGT GAC GGC CAT CAG GAT TGC CAG GAT GGC CAG GAC GAG GCC AAC          4689
Arg Cys Asp Gly His Gln Asp Cys Gln Asp Gly Gln Asp Glu Ala Asn
        1490                1495                1500

TGC CCC ACT CAC AGC ACC TTG ACC TGC ATG AGC TGG GAG TTC AAG TGT          4737
Cys Pro Thr His Ser Thr Leu Thr Cys Met Ser Trp Glu Phe Lys Cys
1505                1510                1515                1520

GAG GAT GGC GAG GCC TGC ATC GTG CTG TCA GAA CGC TGC GAC GGC TTC          4785
Glu Asp Gly Glu Ala Cys Ile Val Leu Ser Glu Arg Cys Asp Gly Phe
                1525                1530                1535

CTG GAC TGC TCA GAT GAG AGC GAC GAG AAG GCC TGC AGT GAT GAG TTA          4833
Leu Asp Cys Ser Asp Glu Ser Asp Glu Lys Ala Cys Ser Asp Glu Leu
            1540                1545                1550

ACT GTA TAC AAA GTA CAG AAT CTT CAG TGG ACA GCT GAC TTC TCT GGG          4881
Thr Val Tyr Lys Val Gln Asn Leu Gln Trp Thr Ala Asp Phe Ser Gly
        1555                1560                1565

AAT GTC ACT TTG ACC TGG ATG CGG CCC AAA AAA ATG CCC TCT GCT GCT          4929
Asn Val Thr Leu Thr Trp Met Arg Pro Lys Lys Met Pro Ser Ala Ala
        1570                1575                1580

TGT GTA TAC AAC GTG TAC TAT AGA GTT GTT GGA GAG AGC ATA TGG AAG          4977
```

|     |     |     |     |     |     |     |     |     |     |     |     |     |     |     |      |
|-----|-----|-----|-----|-----|-----|-----|-----|-----|-----|-----|-----|-----|-----|-----|------|
| Cys | Val | Tyr | Asn | Val | Tyr | Tyr | Arg | Val | Val | Gly | Glu | Ser | Ile | Trp | Lys  |
| 1585|     |     |     | 1590|     |     |     |     |     | 1595|     |     |     |     | 1600 |

| ACT | CTG | GAG | ACT | CAC | AGC | AAT | AAG | ACA | AAC | ACT | GTA | TTA | AAA | GTG | TTG | 5025 |
|-----|-----|-----|-----|-----|-----|-----|-----|-----|-----|-----|-----|-----|-----|-----|-----|------|
| Thr | Leu | Glu | Thr | His | Ser | Asn | Lys | Thr | Asn | Thr | Val | Leu | Lys | Val | Leu |      |
|     |     |     |     | 1605|     |     |     |     | 1610|     |     |     |     | 1615|     |      |

| AAA | CCA | GAT | ACC | ACC | TAC | CAG | GTT | AAA | GTG | CAG | GTT | CAG | TGC | CTG | AGC | 5073 |
|-----|-----|-----|-----|-----|-----|-----|-----|-----|-----|-----|-----|-----|-----|-----|-----|------|
| Lys | Pro | Asp | Thr | Thr | Tyr | Gln | Val | Lys | Val | Gln | Val | Gln | Cys | Leu | Ser |      |
|     |     |     | 1620|     |     |     |     |     | 1625|     |     |     |     | 1630|     |      |

| AAG | GTG | CAC | AAC | ACC | AAT | GAC | TTT | GTG | ACC | TTG | AGA | ACT | CCA | GAG | GGA | 5121 |
|-----|-----|-----|-----|-----|-----|-----|-----|-----|-----|-----|-----|-----|-----|-----|-----|------|
| Lys | Val | His | Asn | Thr | Asn | Asp | Phe | Val | Thr | Leu | Arg | Thr | Pro | Glu | Gly |      |
|     |     |     | 1635|     |     |     |     | 1640|     |     |     |     | 1645|     |     |      |

| TTG | CCA | GAC | GCC | CCT | CAG | AAC | CTC | CAG | CTG | TCG | CTC | CAC | GGG | GAA | GAG | 5169 |
|-----|-----|-----|-----|-----|-----|-----|-----|-----|-----|-----|-----|-----|-----|-----|-----|------|
| Leu | Pro | Asp | Ala | Pro | Gln | Asn | Leu | Gln | Leu | Ser | Leu | His | Gly | Glu | Glu |      |
|     |     |     | 1650|     |     |     |     | 1655|     |     |     |     | 1660|     |     |      |

| GAA | GGT | GTG | ATT | GTG | GGC | CAC | TGG | AGC | CCT | CCC | ACC | CAC | ACC | CAC | GGC | 5217 |
|-----|-----|-----|-----|-----|-----|-----|-----|-----|-----|-----|-----|-----|-----|-----|-----|------|
| Glu | Gly | Val | Ile | Val | Gly | His | Trp | Ser | Pro | Pro | Thr | His | Thr | His | Gly |      |
| 1665|     |     |     | 1670|     |     |     |     |     | 1675|     |     |     |     | 1680|      |

| CTC | ATT | CGC | GAA | TAC | ATT | GTA | GAG | TAT | AGC | AGG | AGT | GGT | TCC | AAG | GTG | 5265 |
|-----|-----|-----|-----|-----|-----|-----|-----|-----|-----|-----|-----|-----|-----|-----|-----|------|
| Leu | Ile | Arg | Glu | Tyr | Ile | Val | Glu | Tyr | Ser | Arg | Ser | Gly | Ser | Lys | Val |      |
|     |     |     |     | 1685|     |     |     |     | 1690|     |     |     |     | 1695|     |      |

| TGG | ACT | TCA | GAA | AGG | GCT | GCT | AGT | AAC | TTT | ACA | GAA | ATA | AAG | AAC | TTG | 5313 |
|-----|-----|-----|-----|-----|-----|-----|-----|-----|-----|-----|-----|-----|-----|-----|-----|------|
| Trp | Thr | Ser | Glu | Arg | Ala | Ala | Ser | Asn | Phe | Thr | Glu | Ile | Lys | Asn | Leu |      |
|     |     |     | 1700|     |     |     |     | 1705|     |     |     |     | 1710|     |     |      |

| TTG | GTC | AAC | ACC | CTG | TAC | ACC | GTC | AGA | GTG | GCT | GCG | GTG | ACG | AGT | CGT | 5361 |
|-----|-----|-----|-----|-----|-----|-----|-----|-----|-----|-----|-----|-----|-----|-----|-----|------|
| Leu | Val | Asn | Thr | Leu | Tyr | Thr | Val | Arg | Val | Ala | Ala | Val | Thr | Ser | Arg |      |
|     |     |     | 1715|     |     |     |     | 1720|     |     |     |     | 1725|     |     |      |

| GGG | ATA | GGA | AAC | TGG | AGC | GAT | TCC | AAA | TCC | ATT | ACC | ACC | GTG | AAA | GGA | 5409 |
|-----|-----|-----|-----|-----|-----|-----|-----|-----|-----|-----|-----|-----|-----|-----|-----|------|
| Gly | Ile | Gly | Asn | Trp | Ser | Asp | Ser | Lys | Ser | Ile | Thr | Thr | Val | Lys | Gly |      |
|     |     |     | 1730|     |     |     |     | 1735|     |     |     |     | 1740|     |     |      |

| AAA | GCG | ATC | CCG | CCA | CCA | AAT | ATC | CAC | ATT | GAC | AAC | TAC | GAT | GAA | AAT | 5457 |
|-----|-----|-----|-----|-----|-----|-----|-----|-----|-----|-----|-----|-----|-----|-----|-----|------|
| Lys | Ala | Ile | Pro | Pro | Pro | Asn | Ile | His | Ile | Asp | Asn | Tyr | Asp | Glu | Asn |      |
| 1745|     |     |     |     | 1750|     |     |     |     | 1755|     |     |     |     | 1760|      |

| TCC | CTG | AGT | TTT | ACC | CTG | ACC | GTG | GAT | GGG | AAC | ATC | AAG | GTG | AAT | GGC | 5505 |
|-----|-----|-----|-----|-----|-----|-----|-----|-----|-----|-----|-----|-----|-----|-----|-----|------|
| Ser | Leu | Ser | Phe | Thr | Leu | Thr | Val | Asp | Gly | Asn | Ile | Lys | Val | Asn | Gly |      |
|     |     |     |     | 1765|     |     |     |     | 1770|     |     |     |     | 1775|     |      |

| TAT | GTG | GTG | AAC | CTT | TTC | TGG | GCA | TTT | GAC | ACC | CAC | AAA | CAA | GAG | AAG | 5553 |
|-----|-----|-----|-----|-----|-----|-----|-----|-----|-----|-----|-----|-----|-----|-----|-----|------|
| Tyr | Val | Val | Asn | Leu | Phe | Trp | Ala | Phe | Asp | Thr | His | Lys | Gln | Glu | Lys |      |
|     |     |     |     | 1780|     |     |     |     | 1785|     |     |     |     | 1790|     |      |

| AAA | ACC | ATG | AAC | TTC | CAA | GGG | AGC | TCA | GTG | TCC | CAC | AAA | GTT | GGC | AAT | 5601 |
|-----|-----|-----|-----|-----|-----|-----|-----|-----|-----|-----|-----|-----|-----|-----|-----|------|
| Lys | Thr | Met | Asn | Phe | Gln | Gly | Ser | Ser | Val | Ser | His | Lys | Val | Gly | Asn |      |
|     |     |     | 1795|     |     |     |     | 1800|     |     |     |     | 1805|     |     |      |

| CTG | ACA | GCA | CAG | ACG | GCC | TAT | GAG | ATT | TCC | GCC | TGG | GCC | AAG | ACT | GAC | 5649 |
|-----|-----|-----|-----|-----|-----|-----|-----|-----|-----|-----|-----|-----|-----|-----|-----|------|
| Leu | Thr | Ala | Gln | Thr | Ala | Tyr | Glu | Ile | Ser | Ala | Trp | Ala | Lys | Thr | Asp |      |
|     |     | 1810|     |     |     |     | 1815|     |     |     |     | 1820|     |     |     |      |

| TTG | GGC | GAT | AGT | CCT | CTG | TCA | TTT | GAG | CAT | GTC | ACG | ACC | AGA | GGG | GTT | 5697 |
|-----|-----|-----|-----|-----|-----|-----|-----|-----|-----|-----|-----|-----|-----|-----|-----|------|
| Leu | Gly | Asp | Ser | Pro | Leu | Ser | Phe | Glu | His | Val | Thr | Thr | Arg | Gly | Val |      |
| 1825|     |     |     |     | 1830|     |     |     |     | 1835|     |     |     |     | 1840|      |

| CGC | CCA | CCT | GCT | CCT | AGC | CTC | AAG | GCC | AGG | GCT | ATC | AAT | CAG | ACT | GCA | 5745 |
|-----|-----|-----|-----|-----|-----|-----|-----|-----|-----|-----|-----|-----|-----|-----|-----|------|
| Arg | Pro | Pro | Ala | Pro | Ser | Leu | Lys | Ala | Arg | Ala | Ile | Asn | Gln | Thr | Ala |      |
|     |     |     |     | 1845|     |     |     |     | 1850|     |     |     |     | 1855|     |      |

| GTG | GAA | TGC | ACC | TGG | ACA | GGC | CCC | AGG | AAT | GTG | GTG | TAT | GGC | ATT | TTC | 5793 |
|-----|-----|-----|-----|-----|-----|-----|-----|-----|-----|-----|-----|-----|-----|-----|-----|------|
| Val | Glu | Cys | Thr | Trp | Thr | Gly | Pro | Arg | Asn | Val | Val | Tyr | Gly | Ile | Phe |      |
|     |     |     | 1860|     |     |     |     | 1865|     |     |     |     | 1870|     |     |      |

| TAT | GCC | ACA | TCC | TTC | CTG | GAC | CTC | TAC | CGC | AAC | CCA | AGC | AGC | CTG | ACC | 5841 |
|-----|-----|-----|-----|-----|-----|-----|-----|-----|-----|-----|-----|-----|-----|-----|-----|------|
| Tyr | Ala | Thr | Ser | Phe | Leu | Asp | Leu | Tyr | Arg | Asn | Pro | Ser | Ser | Leu | Thr |      |
|     |     |     | 1875|     |     |     |     | 1880|     |     |     |     | 1885|     |     |      |

| ACG | CCG | CTG | CAC | AAC | GCA | ACC | GTG | CTC | GTC | GGT | AAG | GAT | GAG | CAG | TAT | 5889 |
|-----|-----|-----|-----|-----|-----|-----|-----|-----|-----|-----|-----|-----|-----|-----|-----|------|
| Thr | Pro | Leu | His | Asn | Ala | Thr | Val | Leu | Val | Gly | Lys | Asp | Glu | Gln | Tyr |      |
|     |     | 1890|     |     |     |     | 1895|     |     |     |     | 1900|     |     |     |      |

| CTG | TTT | CTG | GTC | CGG | GTG | GTG | ATG | CCC | TAC | CAA | GGG | CCG | TCC | TCG | GAC | 5937 |

```
Leu Phe Leu Val Arg Val Val Met Pro Tyr Gln Gly Pro Ser Ser Asp
1905                1910                1915                1920

TAC GTG GTC GTG AAG ATG ATC CCG GAC AGC AGG CTT CCT CCC CGG CAC         5985
Tyr Val Val Val Lys Met Ile Pro Asp Ser Arg Leu Pro Pro Arg His
            1925                1930                1935

CTG CAT GCC GTT CAC ACC GGC AAG ACC TCG GCC GTC ATC AAG TGG GAG         6033
Leu His Ala Val His Thr Gly Lys Thr Ser Ala Val Ile Lys Trp Glu
        1940                1945                1950

TCG CCC TAC GAC TCT CCT GAC CAG GAC CTG TTC TAT GCG ATC GCA GTT         6081
Ser Pro Tyr Asp Ser Pro Asp Gln Asp Leu Phe Tyr Ala Ile Ala Val
            1955                1960                1965

AAA GAT CTG ATA CGA AAG ACG GAC CGG AGC TAC AAA GTC AAG TCC CGC         6129
Lys Asp Leu Ile Arg Lys Thr Asp Arg Ser Tyr Lys Val Lys Ser Arg
        1970                1975                1980

AAC AGC ACC GTG GAG TAC ACC CTG AGC AAG CTG GAG CCC GGA GGG AAA         6177
Asn Ser Thr Val Glu Tyr Thr Leu Ser Lys Leu Glu Pro Gly Gly Lys
1985                1990                1995                2000

TAC CAC GTC ATT GTG CAG CTG GGG AAC ATG AGC AAA GAT GCC AGT GTG         6225
Tyr His Val Ile Val Gln Leu Gly Asn Met Ser Lys Asp Ala Ser Val
            2005                2010                2015

AAG ATC ACC ACC GTT TCG TTA TCG GCA CCC GAT GCC TTA AAA ATC ATA         6273
Lys Ile Thr Thr Val Ser Leu Ser Ala Pro Asp Ala Leu Lys Ile Ile
        2020                2025                2030

ACA GAA AAT GAC CAC GTC CTT CTC TTC TGG AAA AGT CTA GCT CTA AAG         6321
Thr Glu Asn Asp His Val Leu Leu Phe Trp Lys Ser Leu Ala Leu Lys
        2035                2040                2045

GAA AAG TAT TTT AAC GAA AGC AGG GGC TAC GAG ATA CAC ATG TTT GAT         6369
Glu Lys Tyr Phe Asn Glu Ser Arg Gly Tyr Glu Ile His Met Phe Asp
        2050                2055                2060

AGC GCC ATG AAT ATC ACC GCA TAC CTT GGG AAT ACT ACT GAC AAT TTC         6417
Ser Ala Met Asn Ile Thr Ala Tyr Leu Gly Asn Thr Thr Asp Asn Phe
2065                2070                2075                2080

TTT AAA ATT TCC AAC CTG AAG ATG GGT CAC AAT TAC ACA TTC ACG TCC         6465
Phe Lys Ile Ser Asn Leu Lys Met Gly His Asn Tyr Thr Phe Thr Val
            2085                2090                2095

CAG GCA CGA TGC CTT TTG GGC AGC CAG ATC TGC GGG GAG CCT GCC GTG         6513
Gln Ala Arg Cys Leu Leu Gly Ser Gln Ile Cys Gly Glu Pro Ala Val
        2100                2105                2110

CTA CTG TAT GAT GAG CTG GGG TCT GGT GGC GAT GCG TCG GCG ATG CAG         6561
Leu Leu Tyr Asp Glu Leu Gly Ser Gly Gly Asp Ala Ser Ala Met Gln
        2115                2120                2125

GCT GCC AGG TCT ACT GAT GTC GCC GCC GTG GTG GTG CCC ATC CTG TTT         6609
Ala Ala Arg Ser Thr Asp Val Ala Ala Val Val Val Pro Ile Leu Phe
        2130                2135                2140

CTG ATA CTG CTG AGC CTG GGG GTC GGG TTT GCC ATC CTG TAC ACG AAG         6657
Leu Ile Leu Leu Ser Leu Gly Val Gly Phe Ala Ile Leu Tyr Thr Lys
2145                2150                2155                2160

CAT CGG AGG CTG CAG AGC AGC TTC ACC GCC TTC GCC AAC AGC CAC TAC         6705
His Arg Arg Leu Gln Ser Ser Phe Thr Ala Phe Ala Asn Ser His Tyr
            2165                2170                2175

AGC TCC AGA CTC GGC TCC GCC ATC TTC TCC TCT GGG GAT GAC TTG GGG         6753
Ser Ser Arg Leu Gly Ser Ala Ile Phe Ser Ser Gly Asp Asp Leu Gly
        2180                2185                2190

GAG GAT GAT GAA GAT GCT CCT ATG ATC ACT GGA TTT TCG GAC GAC GTC         6801
Glu Asp Asp Glu Asp Ala Pro Met Ile Thr Gly Phe Ser Asp Asp Val
        2195                2200                2205

CCC ATG GTG ATA GCC TGA AAGAGCTTTC CTCACTAGAA ACCAAATGGT                6849
Pro Met Val Ile Ala *
    2210

GTAAATATTT TATTTGATAA AGATAGTTGA TGGTTTATTT TAAAAGATGC ACTTTGAGTT       6909
```

GCAATATGTT ATTTTTATAT GGGCCAAAAA CAAAAGCAAA AAAAAAAAAA AA         6961

( 2 ) INFORMATION FOR SEQ ID NO:3:

( i ) SEQUENCE CHARACTERISTICS:
    ( A ) LENGTH: 2213 amino acids
    ( B ) TYPE: amino acid
    ( D ) TOPOLOGY: linear ( i i ) MOLECULE TYPE: protein ( x i ) SEQUENCE DESCRIPTION: SEQ ID NO:3:

| Met | Ala | Thr | Arg | Ser | Ser | Arg | Arg | Glu | Ser | Arg | Leu | Pro | Phe | Leu | Phe |
|---|---|---|---|---|---|---|---|---|---|---|---|---|---|---|---|
| 1 | | | | 5 | | | | | 10 | | | | | 15 | |
| Thr | Leu | Val | Ala | Leu | Leu | Pro | Pro | Gly | Ala | Leu | Cys | Glu | Val | Trp | Thr |
| | | | 20 | | | | 25 | | | | | 30 | | | |
| Arg | Thr | Leu | His | Gly | Gly | Arg | Ala | Pro | Leu | Pro | Gln | Glu | Arg | Gly | Phe |
| | | 35 | | | | | 40 | | | | | 45 | | | |
| Arg | Val | Val | Gln | Gly | Asp | Pro | Arg | Glu | Leu | Arg | Leu | Trp | Glu | Arg | Gly |
| | 50 | | | | | 55 | | | | | 60 | | | | |
| Asp | Ala | Arg | Gly | Ala | Ser | Arg | Ala | Asp | Glu | Lys | Pro | Leu | Arg | Arg | Arg |
| 65 | | | | | 70 | | | | 75 | | | | | | 80 |
| Arg | Ser | Ala | Ala | Leu | Gln | Pro | Glu | Pro | Ile | Lys | Val | Tyr | Gly | Gln | Val |
| | | | | 85 | | | | | 90 | | | | | 95 | |
| Ser | Leu | Asn | Asp | Ser | His | Asn | Gln | Met | Val | Val | His | Trp | Ala | Gly | Glu |
| | | | 100 | | | | | 105 | | | | | 110 | | |
| Lys | Ser | Asn | Val | Ile | Val | Ala | Leu | Ala | Arg | Asp | Ser | Leu | Ala | Leu | Ala |
| | | 115 | | | | | 120 | | | | | 125 | | | |
| Arg | Pro | Arg | Ser | Ser | Asp | Val | Tyr | Val | Ser | Tyr | Asp | Tyr | Gly | Lys | Ser |
| | 130 | | | | | 135 | | | | | 140 | | | | |
| Phe | Asn | Lys | Ile | Ser | Glu | Lys | Leu | Asn | Phe | Gly | Ala | Gly | Asn | Asn | Thr |
| 145 | | | | | 150 | | | | | 155 | | | | | 160 |
| Glu | Ala | Val | Val | Ala | Gln | Phe | Tyr | His | Ser | Pro | Ala | Asp | Asn | Lys | Arg |
| | | | | 165 | | | | | 170 | | | | | 175 | |
| Tyr | Ile | Phe | Ala | Asp | Ala | Tyr | Ala | Gln | Tyr | Leu | Trp | Ile | Thr | Phe | Asp |
| | | | 180 | | | | | 185 | | | | | 190 | | |
| Phe | Cys | Asn | Thr | Ile | His | Gly | Phe | Ser | Ile | Pro | Phe | Arg | Ala | Ala | Asp |
| | | 195 | | | | | 200 | | | | | 205 | | | |
| Leu | Leu | Leu | His | Ser | Lys | Ala | Ser | Asn | Leu | Leu | Leu | Gly | Phe | Asp | Arg |
| | 210 | | | | | 215 | | | | | 220 | | | | |
| Ser | His | Pro | Asn | Lys | Gln | Leu | Trp | Lys | Ser | Asp | Asp | Phe | Gly | Gln | Thr |
| 225 | | | | | 230 | | | | | 235 | | | | | 240 |
| Trp | Ile | Met | Ile | Gln | Glu | His | Val | Lys | Ser | Phe | Ser | Trp | Gly | Ile | Asp |
| | | | | 245 | | | | | 250 | | | | | 255 | |
| Pro | Tyr | Asp | Lys | Pro | Asn | Thr | Ile | Tyr | Ile | Glu | Arg | His | Glu | Pro | Ser |
| | | | 260 | | | | | 265 | | | | | 270 | | |
| Gly | Tyr | Ser | Thr | Val | Phe | Arg | Ser | Thr | Asp | Phe | Phe | Gln | Ser | Arg | Glu |
| | | 275 | | | | | 280 | | | | | 285 | | | |
| Asn | Gln | Glu | Val | Ile | Leu | Glu | Glu | Val | Arg | Asp | Phe | Gln | Leu | Arg | Asp |
| | 290 | | | | | 295 | | | | | 300 | | | | |
| Lys | Tyr | Met | Phe | Ala | Thr | Lys | Val | Val | His | Leu | Leu | Gly | Ser | Pro | Leu |
| 305 | | | | | 310 | | | | | 315 | | | | | 320 |
| Gln | Ser | Ser | Val | Gln | Leu | Trp | Val | Ser | Phe | Gly | Arg | Lys | Pro | Met | Arg |
| | | | | 325 | | | | | 330 | | | | | 335 | |
| Ala | Ala | Gln | Phe | Val | Thr | Arg | His | Pro | Ile | Asn | Glu | Tyr | Tyr | Ile | Ala |
| | | | 340 | | | | | 345 | | | | | 350 | | |

| | | | | | | | | | | | | | | |
|---|---|---|---|---|---|---|---|---|---|---|---|---|---|---|
| Asp | Ala | Ser 355 | Glu | Asp | Gln | Val | Phe 360 | Val | Cys | Val | Ser | His 365 | Ser | Asn | Asn |
| Arg | Thr 370 | Asn | Leu | Tyr | Ile | Ser 375 | Glu | Ala | Glu | Gly | Leu 380 | Lys | Phe | Ser | Leu |
| Ser 385 | Leu | Glu | Asn | Val | Leu 390 | Tyr | Tyr | Thr | Pro | Gly 395 | Gly | Ala | Gly | Ser | Asp 400 |
| Thr | Leu | Val | Arg | Tyr 405 | Phe | Ala | Asn | Glu | Pro 410 | Phe | Ala | Asp | Phe | His 415 | Arg |
| Val | Glu | Gly | Leu 420 | Gln | Gly | Val | Tyr | Ile 425 | Ala | Thr | Leu | Ile | Asn 430 | Gly | Ser |
| Met | Asn | Glu 435 | Glu | Asn | Met | Arg | Ser 440 | Val | Ile | Thr | Phe | Asp 445 | Lys | Gly | Gly |
| Thr | Trp 450 | Glu | Phe | Leu | Gln | Ala 455 | Pro | Ala | Phe | Thr | Gly 460 | Tyr | Gly | Glu | Lys |
| Ile 465 | Asn | Cys | Glu | Leu | Ser 470 | Glu | Gly | Cys | Ser | Leu 475 | His | Leu | Ala | Gln | Arg 480 |
| Leu | Ser | Gln | Leu | Leu 485 | Asn | Leu | Gln | Leu | Arg 490 | Arg | Met | Pro | Ile | Leu 495 | Ser |
| Lys | Glu | Ser | Ala 500 | Pro | Gly | Leu | Ile | Ile 505 | Ala | Thr | Gly | Ser | Val 510 | Gly | Lys |
| Asn | Leu | Ala 515 | Ser | Lys | Thr | Asn | Val 520 | Tyr | Ile | Ser | Ser | Ala 525 | Gly | Ala |
| Arg | Trp 530 | Arg | Glu | Ala | Leu | Pro 535 | Gly | Pro | His | Tyr | Tyr 540 | Thr | Trp | Gly | Asp |
| His 545 | Gly | Gly | Ile | Ile | Met 550 | Ala | Ile | Ala | Gln | Gly 555 | Met | Glu | Thr | Asn | Glu 560 |
| Leu | Lys | Tyr | Ser | Thr 565 | Asn | Glu | Gly | Glu | Thr 570 | Trp | Lys | Ala | Phe | Thr 575 | Phe |
| Ser | Glu | Lys | Pro 580 | Val | Phe | Val | Tyr | Gly 585 | Leu | Leu | Thr | Glu | Pro 590 | Gly | Glu |
| Lys | Ser | Thr 595 | Val | Phe | Thr | Ile | Phe 600 | Gly | Ser | Asn | Lys | Glu 605 | Asn | Val | His |
| Ser | Trp 610 | Leu | Ile | Leu | Gln | Val 615 | Asn | Ala | Thr | Asp | Ala 620 | Leu | Gly | Val | Pro |
| Cys 625 | Thr | Glu | Asn | Asp | Tyr 630 | Lys | Leu | Trp | Ser | Pro 635 | Ser | Asp | Glu | Arg | Gly 640 |
| Asn | Glu | Cys | Leu | Leu 645 | Gly | His | Lys | Thr | Val 650 | Phe | Lys | Arg | Arg 655 | Thr | Pro |
| His | Ala | Thr | Cys 660 | Phe | Asn | Gly | Glu | Asp 665 | Phe | Asp | Arg | Pro | Val 670 | Val |
| Ser | Asn | Cys 675 | Ser | Cys | Thr | Arg | Glu 680 | Asp | Tyr | Glu | Cys | Asp 685 | Phe | Gly | Phe |
| Arg | Met 690 | Ser | Glu | Asp | Leu | Ala 695 | Leu | Glu | Val | Cys | Val 700 | Pro | Asp | Pro | Gly |
| Phe 705 | Ser | Gly | Lys | Ser | Ser 710 | Pro | Pro | Val | Pro | Cys 715 | Pro | Val | Gly | Ser | Thr 720 |
| Tyr | Arg | Arg | Ser | Arg 725 | Gly | Tyr | Arg | Lys | Ile 730 | Ser | Gly | Asp | Thr | Cys 735 | Ser |
| Gly | Gly | Asp | Val 740 | Glu | Ala | Arg | Leu | Glu 745 | Gly | Glu | Leu | Val 750 | Pro | Cys | Pro |
| Leu | Ala | Glu 755 | Glu | Asn | Glu | Phe | Ile 760 | Leu | Tyr | Ala | Thr | Arg 765 | Lys | Ser | Ile |
| His | Arg | Tyr | Asp | Leu | Ala | Ser | Gly | Thr | Thr | Glu | Gln | Leu | Pro | Leu | Thr |

|     |     |     |     |     |     |     |     |     |     |     |     |     |     |     |
| --- | --- | --- | --- | --- | --- | --- | --- | --- | --- | --- | --- | --- | --- | --- |
|     |     | 770 |     |     |     | 775 |     |     |     |     |     | 780 |     |     |
| Gly | Leu | Arg | Ala | Ala | Val | Ala | Leu | Asp | Phe | Asp | Tyr | Glu | His | Asn | Cys |
| 785 |     |     |     | 790 |     |     |     |     | 795 |     |     |     |     | 800 |
| Leu | Tyr | Trp | Ser | Asp | Leu | Ala | Leu | Asp | Val | Ile | Gln | Arg | Leu | Cys | Leu |
|     |     |     |     | 805 |     |     |     | 810 |     |     |     |     | 815 |     |
| Asn | Gly | Ser | Thr | Gly | Gln | Glu | Val | Ile | Ile | Asn | Ser | Asp | Leu | Glu | Thr |
|     |     |     | 820 |     |     |     |     | 825 |     |     |     |     | 830 |     |
| Val | Glu | Ala | Leu | Ala | Phe | Glu | Pro | Leu | Ser | Gln | Leu | Leu | Tyr | Trp | Val |
|     |     | 835 |     |     |     |     | 840 |     |     |     |     | 845 |     |     |
| Asp | Ala | Gly | Phe | Lys | Lys | Ile | Glu | Val | Ala | Asn | Pro | Asp | Gly | Asp | Phe |
|     | 850 |     |     |     |     | 855 |     |     |     |     | 860 |     |     |     |
| Arg | Leu | Thr | Val | Val | Asn | Ser | Ser | Val | Leu | Asp | Arg | Pro | Arg | Ala | Leu |
| 865 |     |     |     |     | 870 |     |     |     |     | 875 |     |     |     |     | 880 |
| Val | Leu | Val | Pro | Gln | Glu | Gly | Ile | Met | Phe | Trp | Thr | Asp | Trp | Gly | Asp |
|     |     |     |     | 885 |     |     |     |     | 890 |     |     |     |     | 895 |     |
| Leu | Lys | Pro | Gly | Ile | Tyr | Arg | Ser | Asn | Met | Asp | Gly | Ser | Ala | Ala | Tyr |
|     |     |     | 900 |     |     |     |     | 905 |     |     |     |     | 910 |     |
| Arg | Leu | Val | Ser | Glu | Asp | Val | Lys | Trp | Pro | Asn | Gly | Ile | Ser | Val | Asp |
|     |     | 915 |     |     |     |     | 920 |     |     |     |     | 925 |     |     |
| Asp | Gln | Trp | Ile | Tyr | Trp | Thr | Asp | Ala | Tyr | Leu | Asp | Cys | Ile | Glu | Arg |
|     | 930 |     |     |     |     | 935 |     |     |     |     | 940 |     |     |     |
| Ile | Thr | Phe | Ser | Gly | Gln | Gln | Arg | Ser | Val | Ile | Leu | Asp | Arg | Leu | Pro |
| 945 |     |     |     |     | 950 |     |     |     |     | 955 |     |     |     |     | 960 |
| His | Pro | Tyr | Ala | Ile | Ala | Val | Phe | Lys | Asn | Glu | Ile | Tyr | Trp | Asp | Asp |
|     |     |     |     | 965 |     |     |     |     | 970 |     |     |     |     | 975 |     |
| Trp | Ser | Gln | Leu | Ser | Ile | Phe | Arg | Ala | Ser | Lys | Tyr | Ser | Gly | Ser | Gln |
|     |     |     | 980 |     |     |     |     | 985 |     |     |     |     | 990 |     |
| Met | Glu | Ile | Leu | Ala | Ser | Gln | Leu | Thr | Gly | Leu | Met | Asp | Met | Lys | Ile |
|     |     |     | 995 |     |     |     |     | 1000 |    |     |     |     | 1005 |    |
| Phe | Tyr | Lys | Gly | Lys | Asn | Thr | Gly | Ser | Asn | Ala | Cys | Val | Pro | Arg | Pro |
|     |     |     | 1010 |    |     |     |     | 1015 |    |     |     |     | 1020 |    |     |
| Cys | Ser | Leu | Leu | Cys | Leu | Pro | Arg | Ala | Asn | Asn | Ser | Lys | Ser | Cys | Arg |
| 1025 |    |     |     |     | 1030 |    |     |     |     | 1035 |    |     |     |     | 1040 |
| Cys | Pro | Asp | Gly | Val | Ala | Ser | Ser | Val | Leu | Pro | Ser | Gly | Asp | Leu | Met |
|     |     |     |     | 1045 |    |     |     |     | 1050 |    |     |     |     | 1055 |    |
| Cys | Asp | Cys | Pro | Lys | Gly | Tyr | Glu | Leu | Lys | Asn | Asn | Thr | Cys | Val | Lys |
|     |     |     | 1060 |    |     |     |     | 1065 |    |     |     |     | 1070 |    |     |
| Glu | Glu | Asp | Thr | Cys | Leu | Arg | Asn | Gln | Tyr | Arg | Cys | Ser | Asn | Gly | Asn |
|     |     |     | 1075 |    |     |     |     | 1080 |    |     |     |     | 1085 |    |     |
| Cys | Ile | Asn | Ser | Ile | Trp | Trp | Cys | Asp | Phe | Asp | Asn | Asp | Cys | Gly | Asp |
|     |     |     | 1090 |    |     |     |     | 1095 |    |     |     |     | 1100 |    |     |
| Met | Ser | Asp | Glu | Lys | Asn | Cys | Pro | Thr | Thr | Ile | Cys | Asp | Leu | Asp | Thr |
| 1105 |    |     |     |     | 1110 |    |     |     |     | 1115 |    |     |     |     | 1120 |
| Gln | Phe | Arg | Cys | Gln | Glu | Ser | Gly | Thr | Cys | Ile | Pro | Leu | Ser | Tyr | Lys |
|     |     |     |     | 1125 |    |     |     |     | 1130 |    |     |     |     | 1135 |    |
| Cys | Asp | Leu | Glu | Asp | Asp | Cys | Gly | Asp | Asn | Ser | Asp | Glu | Arg | His | Cys |
|     |     |     |     | 1140 |    |     |     |     | 1145 |    |     |     |     | 1150 |    |
| Glu | Met | His | Gln | Cys | Arg | Ser | Asp | Glu | Tyr | Asn | Cys | Ser | Ser | Gly | Met |
|     |     |     | 1155 |    |     |     |     | 1160 |    |     |     |     | 1165 |    |     |
| Cys | Ile | Arg | Ser | Ser | Trp | Val | Cys | Asp | Gly | Asp | Asn | Asp | Cys | Arg | Asp |
|     |     |     | 1170 |    |     |     |     | 1175 |    |     |     |     | 1180 |    |     |
| Trp | Ser | Asp | Glu | Ala | Asn | Cys | Thr | Ala | Ile | Tyr | His | Thr | Cys | Glu | Ala |
| 1185 |    |     |     |     | 1190 |    |     |     |     | 1195 |    |     |     |     | 1200 |

-continued

| Ser | Asn | Phe | Gln | Cys | Arg | Asn | Gly | His | Cys | Ile | Pro | Gln | Arg | Trp | Ala |
|     |     |     |     | 1205 |     |     |     | 1210 |     |     |     |     | 1215 |     |     |

Cys Asp Gly Asp Ala Asp Cys Gln Asp Gly Ser Asp Glu Asp Pro Ala
            1220             1225                 1230

Asn Cys Glu Lys Lys Cys Asn Gly Phe Arg Cys Pro Asn Gly Thr Cys
        1235             1240                 1245

Ile Pro Ser Thr Lys His Cys Asp Gly Leu His Asp Cys Ser Asp Gly
        1250             1255                 1260

Ser Asp Glu Gln His Cys Glu Pro Leu Cys Thr Arg Phe Met Asp Phe
1265             1270             1275                 1280

Val Cys Lys Asn Arg Gln Gln Cys Leu Phe His Ser Met Val Cys Asp
            1285             1290                 1295

Gly Ile Ile Gln Cys Arg Asp Gly Ser Asp Glu Asp Pro Ala Phe Ala
            1300             1305                 1310

Gly Cys Ser Arg Asp Pro Glu Phe His Lys Val Cys Asp Glu Phe Gly
            1315             1320                 1325

Phe Gln Cys Gln Asn Gly Val Cys Ile Ser Leu Ile Trp Lys Cys Asp
            1330             1335                 1340

Gly Met Asp Asp Cys Gly Asp Tyr Ser Asp Glu Ala Asn Cys Glu Asn
1345             1350             1355                 1360

Pro Thr Glu Ala Pro Asn Cys Ser Arg Tyr Phe Gln Phe Arg Cys Asp
            1365             1370                 1375

Asn Gly His Cys Ile Pro Asn Arg Trp Lys Cys Asp Arg Glu Asn Asp
            1380             1385                 1390

Cys Gly Asp Trp Ser Asp Glu Lys Asp Cys Gly Asp Ser His Val Leu
            1395             1400                 1405

Pro Ser Thr Thr Pro Ala Pro Ser Thr Cys Leu Pro Asn Tyr Tyr Arg
            1410             1415                 1420

Cys Gly Gly Gly Ala Cys Val Ile Asp Thr Trp Val Cys Asp Gly Tyr
1425             1430             1435                 1440

Arg Asp Cys Ala Asp Gly Ser Asp Glu Glu Ala Cys Pro Ser Leu Pro
            1445             1450                 1455

Asn Val Thr Ala Thr Ser Ser Pro Ser Gln Pro Gly Arg Cys Asp Arg
            1460             1465                 1470

Phe Glu Phe Glu Cys His Gln Pro Lys Lys Cys Ile Pro Asn Trp Arg
            1475             1480                 1485

Arg Cys Asp Gly His Gln Asp Cys Gln Asp Gly Gln Asp Glu Ala Asn
            1490             1495                 1500

Cys Pro Thr His Ser Thr Leu Thr Cys Met Ser Trp Glu Phe Lys Cys
1505             1510             1515                 1520

Glu Asp Gly Glu Ala Cys Ile Val Leu Ser Glu Arg Cys Asp Gly Phe
            1525             1530                 1535

Leu Asp Cys Ser Asp Glu Ser Asp Glu Lys Ala Cys Ser Asp Glu Leu
            1540             1545                 1550

Thr Val Tyr Lys Val Gln Asn Leu Gln Trp Thr Ala Asp Phe Ser Gly
            1555             1560                 1565

Asn Val Thr Leu Thr Trp Met Arg Pro Lys Lys Met Pro Ser Ala Ala
            1570             1575                 1580

Cys Val Tyr Asn Val Tyr Arg Val Val Gly Glu Ser Ile Trp Lys
1585             1590             1595                 1600

Thr Leu Glu Thr His Ser Asn Lys Thr Asn Thr Val Leu Lys Val Leu
            1605             1610                 1615

Lys Pro Asp Thr Thr Tyr Gln Val Lys Val Gln Val Gln Cys Leu Ser
            1620             1625                 1630

```
Lys Val His Asn Thr Asn Asp Phe Val Thr Leu Arg Thr Pro Glu Gly
         1635                1640                1645
Leu Pro Asp Ala Pro Gln Asn Leu Gln Leu Ser Leu His Gly Glu Glu
1650                1655                1660
Glu Gly Val Ile Val Gly His Trp Ser Pro Thr His Thr His Gly
1665                1670                1675                1680
Leu Ile Arg Glu Tyr Ile Val Glu Tyr Ser Arg Ser Gly Ser Lys Val
                    1685                1690                1695
Trp Thr Ser Glu Arg Ala Ala Ser Asn Phe Thr Glu Ile Lys Asn Leu
             1700                1705                1710
Leu Val Asn Thr Leu Tyr Thr Val Arg Val Ala Ala Val Thr Ser Arg
         1715                1720                1725
Gly Ile Gly Asn Trp Ser Asp Ser Lys Ser Ile Thr Thr Val Lys Gly
     1730                1735                1740
Lys Ala Ile Pro Pro Pro Asn Ile His Ile Asp Asn Tyr Asp Glu Asn
1745                1750                1755                1760
Ser Leu Ser Phe Thr Leu Thr Val Asp Gly Asn Ile Lys Val Asn Gly
                 1765                1770                1775
Tyr Val Val Asn Leu Phe Trp Ala Phe Asp Thr His Lys Gln Glu Lys
             1780                1785                1790
Lys Thr Met Asn Phe Gln Gly Ser Ser Val Ser His Lys Val Gly Asn
         1795                1800                1805
Leu Thr Ala Gln Thr Ala Tyr Glu Ile Ser Ala Trp Ala Lys Thr Asp
     1810                1815                1820
Leu Gly Asp Ser Pro Leu Ser Phe Glu His Val Thr Thr Arg Gly Val
1825                1830                1835                1840
Arg Pro Pro Ala Pro Ser Leu Lys Ala Arg Ala Ile Asn Gln Thr Ala
                 1845                1850                1855
Val Glu Cys Thr Trp Thr Gly Pro Arg Asn Val Val Tyr Gly Ile Phe
             1860                1865                1870
Tyr Ala Thr Ser Phe Leu Asp Leu Tyr Arg Asn Pro Ser Ser Leu Thr
         1875                1880                1885
Thr Pro Leu His Asn Ala Thr Val Leu Val Gly Lys Asp Glu Gln Tyr
     1890                1895                1900
Leu Phe Leu Val Arg Val Val Met Pro Tyr Gln Gly Pro Ser Ser Asp
1905                1910                1915                1920
Tyr Val Val Val Lys Met Ile Pro Asp Ser Arg Leu Pro Pro Arg His
                 1925                1930                1935
Leu His Ala Val His Thr Gly Lys Thr Ser Ala Val Ile Lys Trp Glu
             1940                1945                1950
Ser Pro Tyr Asp Ser Pro Asp Gln Asp Leu Phe Tyr Ala Ile Ala Val
         1955                1960                1965
Lys Asp Leu Ile Arg Lys Thr Asp Arg Ser Tyr Lys Val Lys Ser Arg
     1970                1975                1980
Asn Ser Thr Val Glu Tyr Thr Leu Ser Lys Leu Glu Pro Gly Gly Lys
1985                1990                1995                2000
Tyr His Val Ile Val Gln Leu Gly Asn Met Ser Lys Asp Ala Ser Val
                 2005                2010                2015
Lys Ile Thr Thr Val Ser Leu Ser Ala Pro Asp Ala Leu Lys Ile Ile
             2020                2025                2030
Thr Glu Asn Asp His Val Leu Leu Phe Trp Lys Ser Leu Ala Leu Lys
         2035                2040                2045
Glu Lys Tyr Phe Asn Glu Ser Arg Gly Tyr Glu Ile His Met Phe Asp
```

```
                2050                    2055                      2060
Ser Ala Met Asn Ile Thr Ala Tyr Leu Gly Asn Thr Thr Asp Asn Phe
2065                2070                2075                2080

Phe Lys Ile Ser Asn Leu Lys Met Gly His Asn Tyr Thr Phe Thr Val
                2085                2090                2095

Gln Ala Arg Cys Leu Leu Gly Ser Gln Ile Cys Gly Glu Pro Ala Val
                2100                2105                2110

Leu Leu Tyr Asp Glu Leu Gly Ser Gly Gly Asp Ala Ser Ala Met Gln
            2115                2120                2125

Ala Ala Arg Ser Thr Asp Val Ala Ala Val Val Pro Ile Leu Phe
2130                2135                2140

Leu Ile Leu Leu Ser Leu Gly Val Gly Phe Ala Ile Leu Tyr Thr Lys
2145                2150                2155                2160

His Arg Arg Leu Gln Ser Ser Phe Thr Ala Phe Ala Asn Ser His Tyr
                    2165                2170                2175

Ser Ser Arg Leu Gly Ser Ala Ile Phe Ser Ser Gly Asp Asp Leu Gly
                2180                2185                2190

Glu Asp Asp Glu Asp Ala Pro Met Ile Thr Gly Phe Ser Asp Asp Val
            2195                2200                2205

Pro Met Val Ile Ala
        2210
```

( 2 ) INFORMATION FOR SEQ ID NO:4:

( i ) SEQUENCE CHARACTERISTICS:
        ( A ) LENGTH: 300 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:4:

```
ATATCCACAT TGACAGCTAT GGTGAAAATT ATCTAAGCTT CACCCTGACC ATGGAGAGTG    60
ATATCAAGGT GAATGGCTAT GTGGTGAACC TTTTCTGGGC ATTTGACACC CACAAGCAAG   120
AGAGGAGAAC TTTGAACTTC CGAGGAAGCA TATTGTCACA CAAAGTTGGC AATCTGACAG   180
CTCATACATC CTATGAGATT TCTGCCTGGG CCAAGACTGA CTTGGGGGAT AGCCCTCTGG   240
CATTTGAGCA TGTTATGACC AGAGGGGTTC GCCCACCTGC ACCTAGCCTC AAGGCCAAAG   300
```

( 2 ) INFORMATION FOR SEQ ID NO:5:

( i ) SEQUENCE CHARACTERISTICS:
        ( A ) LENGTH: 6642 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:5:

```
ATGGCGACAC GGAGCAGCAG GAGGGAGTCG CGACTCCCGT TCCTATTCAC CCTGGTCGCA    60
CTGCTGCCGC CGGAGCTCT  CTGCGAAGTC TGGACGCAGA GGCTGCACGG CGGCAGCGCG   120
CCCTTGCCCC AGGACCGGGG CTTCCTCGTG GTGCAGGGCG ACCCGCGCGA GCTGCGGCTG   180
TGGGCGCGCG GGATGCCAG  GGGGCGAGC  CGCGCGGACG AGAAGCCGCT CCGGAGGAAA   240
CGGAGCGCTG CCCTGCAGCC CGAGCCCATC AAGGTGTACG ACAGGTTAG  TCTGAATGAT   300
TCCCACAATC AGATGGTGGT GCACTGGGCT GGAGAGAAAA GCAACGTGAT CGTGGCCTTG   360
```

```
GCCCGAGATA GCCTGGCATT GGCGAGGCCC AAGAGCAGTG ATGTGTACGT GTCTTACGAC    420
TATGGAAAAT CATTCAAGAA AATTTCAGAC AAGTTAAACT TTGGCTTGGG AAATAGGAGT    480
GAAGCTGTTA TCGCCCAGTT CTACCACAGC CCTGCGGACA ACAAGCGGTA CATCTTTGCA    540
GACGCTTATG CCCAGTACCT CTGGATCACG TTTGACTTCT GCAACACTCT TCAAGGCTTT    600
TCCATCCCAT TTCGGGCAGC TGATCTCCTC CTACACAGTA AGGCCTCCAA CCTTCTCTTG    660
GGCTTTGACA GGTCCACCCC CAACAAGCAG CTGTGGAAGT CAGATGACTT TGGCCAGACC    720
TGGATCATGA TTCAGGAACA TGTCAAGTCC TTTTCTTGGG GAATTGATCC CTATGACAAA    780
CCAAATACCA TCTACATTGA ACGACACGAA CCCTCTGGCT ACTCCACTGT CTTCCAAGT    840
ACAGATTTCT TCCAGTCCCG GGAAAACCAG GAAGTGATCC TTGAGGAAGT GAGAGATTTT    900
CAGCTTCGGG ACAAGTACAT GTTTGCTACA AAGGTGGTGC ATCTCTTGGG CAGTGAACAG    960
CAGTCTTCTG TCCAGCTCTG GGTCTCCTTT GGCCGGAAGC CCATGAGAGC AGCCCAGTTT   1020
GTCACAAGAC ATCCTATTAA TGAATATTAC ATCGCAGATG CCTCCGAGGA CCAGGTGTTT   1080
GTGTGTGTCA GCCACAGTAA CAACCGCACC AATTTATACA TCTCAGAGGC AGAGGGGCTG   1140
AAGTTCTCCC TGTCCTTGGA GAACGTGCTC TATTACAGCC AGGAGGGGC CGGCAGTGAC    1200
ACCTTGGTGA GGTATTTTGC AAATGAACCA TTTGCTGACT TCCACCGAGT GGAAGGATTG   1260
CAAGGAGTCT ACATTGCTAC TCTGATTAAT GGTTCTATGA ATGAGGAGAA CATGAGATCG   1320
GTCATCACCT TTGACAAAGG GGGAACCTGG GAGTTTCTTC AGGCTCCAGC CTTCACGGGA   1380
TATGGAGAGA AAATCAATTG TGAGCTTTCC CAGGGCTGTT CCCTTCATCT GGCTCAGCGC   1440
CTCAGTCAGC TCCTCAACCT CCAGCTCCGG AGAATGCCCA TCCTGTCCAA GGAGTCGGCT   1500
CCAGGCCTCA TCATCGCCAC TGGCTCAGTG GAAAGAACT TGGCTAGCAA GACAAACGTG    1560
TACATCTCTA GCAGTGCTGG AGCCAGGTGG CGAGAGGCAC TTCCTGGACC TCACTACTAC   1620
ACATGGGGAG ACCACGGCGG AATCATCACG GCCATTGCCC AGGGCATGGA AACCAACGAG   1680
CTAAAATACA GTACCAATGA AGGGGAGACC TGGAAAACAT TCATCTTCTC TGAGAAGCCA   1740
GTGTTTGTGT ATGGCCTCCT CACAGAACCT GGGGAGAAGA GCACTGTCTT CACCATCTTT   1800
GGCTCGAACA AAGAGAATGT CCACAGCTGG CTGATCCTCC AGGTCAATGC CACGGATGCC   1860
TTGGGAGTTC CCTGCACAGA GAATGACTAC AAGCTGTGGT CACCATCTGA TGAGCGGGGG   1920
AATGAGTGTT TGCTGGGACA CAAGACTGTT TTCAAACGGC GGACCCCCCA TGCCACATGC   1980
TTCAATGGAG AGGACTTTGA CAGGCCGGTG GTCGTGTCCA ACTGCTCCTG CACCCGGGAG   2040
GACTATGAGT GTGACTTCGG TTTCAAGATG AGTGAAGATT TGTCATTAGA GGTTTGTGTT   2100
CCAGATCCGG AATTTTCTGG AAAGTCATAC TCCCCTCCTG TGCCTTGCCC TGTGGGTTCT   2160
ACTTACAGGA GAACGAGAGG CTACCGGAAG ATTTCTGGGG ACACTTGTAG CGGAGGAGAT   2220
GTTGAAGCGC GACTGGAAGG AGAGCTGGTC CCCTGTCCCC TGGCAGAAGA GAACGAGTTC   2280
ATTCTGTATG CTGTGAGGAA ATCCATCTAC CGCTATGACC TGGCCTCGGG AGCCACCGAG   2340
CAGTTGCCTC TCACCGGGCT ACGGGCAGCA GTGGCCCTGG ACTTTGACTA TGAGCACAAC   2400
TGTTTGTATT GGTCCGACCT GGCCTTGGAC GTCATCCAGC GCCTCTGTTT GAATGAAGC    2460
ACAGGGCAAG AGGTGATCAT CAATTCTGGC CTGGAGACAG TAGAAGCTTT GGCTTTTGAA   2520
CCCCTCAGCC AGCTGCTTTA CTGGGTAGAT GCAGGCTTCA AAAAGATTGA GGTAGCTAAT   2580
CCAGATGGCG ACTTCCGACT CACAATCGTC AATTCCTCTG TGCTTGATCG TCCCAGGGCT   2640
CTGGTCCTCG TGCCCCAAGA GGGGGTGATG TTCTGGACAG ACTGGGGAGA CCTGAAGCCT   2700
GGGATTTATC GGAGCAATAT GGATGGTTCT GCTGCCTATC ACCTGGTGTC TGAGGATGTG   2760
```

| | | | | | | |
|---|---|---|---|---|---|---|
| AAGTGGCCCA | ATGGCATCTC | TGTGGACGAC | CAGTGGATTT | ACTGGACGGA | TGCCTACCTG | 2820 |
| GAGTGCATAG | AGCGGATCAC | GTTCAGTGGC | CAGCAGCGCT | CTGTCATTCT | GGACAACCTC | 2880 |
| CCGCACCCCT | ATGCCATTGC | TGTCTTTAAG | AATGAAATCT | ACTGGGATGA | CTGGTCACAG | 2940 |
| CTCAGCATAT | TCCGAGCTTC | CAAATACAGT | GGGTCCCAGA | TGGAGATTCT | GGCAAACCAG | 3000 |
| CTCACGGGGC | TCATGGACAT | GAAGATTTTC | TACAAGGGGA | AGAACACTGG | AAGCAATGCC | 3060 |
| TGTGTGCCCA | GGCCATGCAG | CCTGCTGTGC | CTGCCCAAGG | CCAACAACAG | TAGAAGCTGC | 3120 |
| AGGTGTCCAG | AGGATGTGTC | CAGCAGTGTG | CTTCCATCAG | GGGACCTGAT | GTGTGACTGC | 3180 |
| CCTCAGGGCT | ATCAGCTCAA | GAACAATACC | TGTGTCAAAG | AAGAGAACAC | CTGTCTTCGC | 3240 |
| AACCAGTATC | GCTGCAGCAA | CGGGAACTGT | ATCAACAGCA | TTTGGTGGTG | TGACTTTGAC | 3300 |
| AACGACTGTG | AGACATGAG | CGATGAGAGA | AACTGCCCTA | CCACCATCTG | TGACCTGGAC | 3360 |
| ACCCAGTTTC | GTTGCCAGGA | GTCTGGGACT | TGTATCCCAC | TGTCCTATAA | ATGTGACCTT | 3420 |
| GAGGATGACT | GTGGAGACAA | CAGTGATGAA | AGTCATTGTG | AAATGCACCA | GTGCCGGAGT | 3480 |
| GACGAGTACA | ACTGCAGTTC | CGGCATGTGC | ATCCGCTCCT | CCTGGGTATG | TGACGGGGAC | 3540 |
| AACGACTGCA | GGGACTGGTC | TGATGAAGCC | AACTGTACCG | CCATCTATCA | CACCTGTGAG | 3600 |
| GCCTCCAACT | TCCAGTGCCG | AAACGGGCAC | TGCATCCCCC | AGCGGTGGGC | GTGTGACGGG | 3660 |
| GATACGGACT | GCCAGGATGG | TTCCGATGAG | GATCCAGTCA | ACTGTGAGAA | GAAGTGCAAT | 3720 |
| GGATTCCGCT | GCCCAAACGG | CACTTGCATC | CCATCCAGCA | ACATTGTGA | TGGTCTGCGT | 3780 |
| GATTGCTCTG | ATGGCTCCGA | TGAACAGCAC | TGCGAGCCCC | TCTGTACGCA | CTTCATGGAC | 3840 |
| TTTGTGTGTA | AGAACCGCCA | GCAGTGCCTG | TTCCACTCCA | TGGTCTGTGA | CGGAATCATC | 3900 |
| CAGTGCCGCG | ACGGGTCCGA | TGAGGATGCG | GCGTTTGCAG | GATGCTCCCA | AGATCCTGAG | 3960 |
| TTCCACAAGG | TATGTGATGA | GTTCGGTTTC | CAGTGTCAGA | ATGGAGTGTG | CATCAGTTTG | 4020 |
| ATTTGGAAGT | GCGACGGGAT | GGATGATTGC | GGCGATTATT | CTGATGAAGC | CAACTGCGAA | 4080 |
| AACCCCACAG | AAGCCCCAAA | CTGCTCCCGC | TACTTCCAGT | TCGGTGTGA | GAATGGCCAC | 4140 |
| TGCATCCCCA | ACAGATGGAA | ATGTGACAGG | GAGAACGACT | GTGGGGACTG | GTCTGATGAG | 4200 |
| AAGGATTGTG | GAGATTCACA | TATTCTTCCC | TTCTCGACTC | CTGGGCCCTC | CACGTGTCTG | 4260 |
| CCCAATTACT | ACCGCTGCAG | CAGTGGGACC | TGCGTGATGG | ACACCTGGGT | GTGCGACGGG | 4320 |
| TACCGAGATT | GTGCAGATGG | CTCTGACGAG | GAAGCCTGCC | CCTTGCTTGC | AAACGTCACT | 4380 |
| GCTGCCTCCA | CTCCCACCCA | ACTTGGGCGA | TGTGACCGAT | TTGAGTTCGA | ATGCCACCAA | 4440 |
| CCGAAGACGT | GTATTCCCAA | CTGGAAGCGC | TGTGACGGCC | ACCAAGATTG | CCAGGATGGC | 4500 |
| CGGGACGAGG | CCAATTGCCC | CACACACAGC | ACCTTGACTT | GCATGAGCAG | GGAGTTCCAG | 4560 |
| TGCGAGGACG | GGGAGGCCTG | CATTGTGCTC | TCGGAGCGCT | GCGACGGCTT | CCTGGACTGC | 4620 |
| TCGGACGAGA | GCGATGAAAA | GGCCTGCAGT | GATGAGTTGA | CTGTGTACAA | AGTACAGAAT | 4680 |
| CTTCAGTGGA | CAGCTGACTT | CTCTGGGGAT | GTGACTTTGA | CCTGGATGAG | GCCCAAAAAA | 4740 |
| ATGCCCTCTG | CATCTTGTGT | ATATAATGTC | TACTACAGGG | TGGTTGGAGA | GAGCATATGG | 4800 |
| AAGACTCTGG | AGACCCACAG | CAATAAGACA | AACACTGTAT | TAAAAGTCTT | GAAACCAGAT | 4860 |
| ACCACGTATC | AGGTTAAAGT | ACAGGTTCAG | TGTCTCAGCA | AGGCACACAA | CACCAATGAC | 4920 |
| TTTGTGACCC | TGAGGACCCC | AGAGGGATTG | CCAGATGCCC | CTCGAAATCT | CCAGCTGTCA | 4980 |
| CTCCCCAGGG | AAGCAGAAGG | TGTGATTGTA | GGCCACTGGG | CTCCTCCCAT | CCACACCCAT | 5040 |
| GGCCTCATCC | GTGAGTACAT | TGTAGAATAC | AGCAGGAGTG | GTTCCAAGAT | GTGGGCCTCC | 5100 |
| CAGAGGGCTG | CTAGTAACTT | TACAGAAATC | AAGAACTTAT | TGGTCAACAC | TCTATACACC | 5160 |

-continued

```
GTCAGAGTGG CTGCGGTGAC TAGTCGTGGA ATAGGAAACT GGAGCGATTC TAAATCCATT    5220
ACCACCATAA AAGGAAAAGT GATCCCACCA CCAGATATCC ACATTGACAG CTATGGTGAA    5280
AATTATCTAA GCTTCACCCT GACCATGGAG AGTGATATCA AGGTGAATGG CTATGTGGTG    5340
AACCTTTTCT GGGCATTTGA CACCCACAAG CAAGAGAGGA GAACTTTGAA CTTCCGAGGA    5400
AGCATATTGT CACACAAAGT TGGCAATCTG ACAGCTCATA CATCCTATGA GATTTCTGCC    5460
TGGGCCAAGA CTGACTTGGG GGATAGCCCT CTGGCATTTG AGCATGTTAT GACCAGAGGG    5520
GTTCGCCCAC CTGCACCTAG CCTCAAGGCC AAAGCCATCA ACCAGACTGC AGTGGAATGT    5580
ACCTGGACCG GCCCCCGGAA TGTGGTTTAT GGTATTTTCT ATGCCACGTC CTTTCTTGAC    5640
CTCTATCGCA ACCCGAAGAG CTTGACTACT TCACTCCACA ACAAGACGGT CATTGTCAGT    5700
AAGGATGAGC AGTATTTGTT TCTGGTCCGT GTAGTGGTAC CCTACCAGGG GCCATCCTCT    5760
GACTACGTTG TAGTGAAGAT GATCCCGGAC AGCAGGCTTC CACCCCGTCA CCTGCATGTG    5820
GTTCATACGG GCAAAACCTC CGTGGTCATC AAGTGGGAAT CACCGTATGA CTCTCCTGAC    5880
CAGGACTTGT TGTATGCAAT TGCAGTCAAA GATCTCATAA GAAAGACTGA CAGGAGCTAC    5940
AAAGTAAAAT CCCGTAACAG CACTGTGGAA TACACCCTTA ACAAGTTGGA GCCTGGCGGG    6000
AAATACCACA TCATTGTCCA ACTGGGGAAC ATGAGCAAAG ATTCCAGCAT AAAAATTACC    6060
ACAGTTTCAT TATCAGCACC TGATGCCTTA AAAATCATAA CAGAAAATGA TCATGTTCTT    6120
CTGTTTTGGA AAAGCCTGGC TTTAAAGGAA AAGCATTTTA ATGAAAGCAG GGGCTATGAG    6180
ATACACATGT TGATAGTGC CATGAATATC ACAGCTTACC TTGGGAATAC TACTGACAAT    6240
TTCTTTAAAA TTCCAACCT GAAGATGGGT CATAATTACA CGTTCACCGT CCAAGCAAGA    6300
TGCCTTTTTG GCAACCAGAT CTGTGGGGAG CCTGCCATCC TGCTGTACGA TGAGCTGGGG    6360
TCTGGTGCAG ATGCATCTGC AACGCAGGCT GCCAGATCTA CGGATGTTGC TGCTGTGGTG    6420
GTGCCCATCT TATTCCTGAT ACTGCTGAGC CTGGGGGTGG GGTTTGCCAT CCTGTACACG    6480
AAGCACCGGA GGCTGCAGAG CAGCTTCACC GCCTTCGCCA ACAGCCACTA CAGCTCCAGG    6540
CTGGGGTCCG CAATCTTCTC CTCTGGGGAT GACCTGGGGG AAGATGATGA AGATGCCCCT    6600
ATGATAACTG GATTTTCAGA TGACGTCCCC ATGGTGATAG CC                       6642
```

( 2 ) INFORMATION FOR SEQ ID NO:6:

( i ) SEQUENCE CHARACTERISTICS:
        ( A ) LENGTH: 6843 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:
        ( A ) NAME/KEY: CDS
        ( B ) LOCATION: 81..6725
        ( D ) OTHER INFORMATION: /note="Identification Method: S"

( i x ) FEATURE:
        ( A ) NAME/KEY: sig_peptide
        ( B ) LOCATION: 81..164
        ( D ) OTHER INFORMATION: /note="Identification Method: S"

( i x ) FEATURE:
        ( A ) NAME/KEY: misc_feature
        ( B ) LOCATION: 165..6722
        ( D ) OTHER INFORMATION: /function="Nucleotides 165-6722
            encode the mature peptide"
        / note="Identification Method: S"

( x i ) SEQUENCE DESCRIPTION: SEQ ID NO:6:

-continued

| | | | | | | |
|---|---|---|---|---|---|---|
| CCGGCCCAGC | GGCTCTCCTG | GCCTCGCGCT | GCACATTCTC | TCCTGGCGGC | GGCGCCACCT | 60 |

| GCAGTAGCGT | TCGCCCGAAC | ATG GCG | ACA CGG | AGC AGC | AGG AGG | GAG TCG | 110 |
|---|---|---|---|---|---|---|---|
| | | Met Ala<br>1 | Thr Arg | Ser Ser<br>5 | Arg Arg | Glu Ser<br>10 | |

| CGA | CTC | CCG | TTC | CTA | TTC | ACC | CTG | GTC | GCA | CTG | CTG | CCG | CCC | GGA | GCT | 158 |
|---|---|---|---|---|---|---|---|---|---|---|---|---|---|---|---|---|
| Arg | Leu | Pro | Phe | Leu<br>15 | Phe | Thr | Leu | Val | Ala<br>20 | Leu | Leu | Pro | Pro | Gly<br>25 | Ala | |

| CTC | TGC | GAA | GTC | TGG | ACG | CAG | AGG | CTG | CAC | GGC | GGC | AGC | GCG | CCC | TTG | 206 |
|---|---|---|---|---|---|---|---|---|---|---|---|---|---|---|---|---|
| Leu | Cys | Glu | Val<br>30 | Trp | Thr | Gln | Arg | Leu<br>35 | His | Gly | Gly | Ser | Ala<br>40 | Pro | Leu | |

| CCC | CAG | GAC | CGG | GGC | TTC | CTC | GTG | GTG | CAG | GGC | GAC | CCG | CGC | GAG | CTG | 254 |
|---|---|---|---|---|---|---|---|---|---|---|---|---|---|---|---|---|
| Pro | Gln | Asp | Arg | Gly<br>45 | Phe | Leu | Val | Val | Gln<br>50 | Gly | Asp | Pro | Arg | Glu<br>55 | Leu | |

| CGG | CTG | TGG | GCG | CGC | GGG | GAT | GCC | AGG | GGG | GCG | AGC | CGC | GCG | GAC | GAG | 302 |
|---|---|---|---|---|---|---|---|---|---|---|---|---|---|---|---|---|
| Arg | Leu<br>60 | Trp | Ala | Arg | Gly | Asp<br>65 | Ala | Arg | Gly | Ala | Ser<br>70 | Arg | Ala | Asp | Glu | |

| AAG | CCG | CTC | CGG | AGG | AAA | CGG | AGC | GCT | GCC | CTG | CAG | CCC | GAG | CCC | ATC | 350 |
|---|---|---|---|---|---|---|---|---|---|---|---|---|---|---|---|---|
| Lys<br>75 | Pro | Leu | Arg | Arg | Lys<br>80 | Arg | Ser | Ala | Ala | Leu<br>85 | Gln | Pro | Glu | Pro | Ile<br>90 | |

| AAG | GTG | TAC | GGA | CAG | GTT | AGT | CTG | AAT | GAT | TCC | CAC | AAT | CAG | ATG | GTG | 398 |
|---|---|---|---|---|---|---|---|---|---|---|---|---|---|---|---|---|
| Lys | Val | Tyr | Gly | Gln<br>95 | Val | Ser | Leu | Asn | Asp<br>100 | Ser | His | Asn | Gln | Met<br>105 | Val | |

| GTG | CAC | TGG | GCT | GGA | GAG | AAA | AGC | AAC | GTG | ATC | GTG | GCC | TTG | GCC | CGA | 446 |
|---|---|---|---|---|---|---|---|---|---|---|---|---|---|---|---|---|
| Val | His | Trp | Ala<br>110 | Gly | Glu | Lys | Ser | Asn<br>115 | Val | Ile | Val | Ala | Leu<br>120 | Ala | Arg | |

| GAT | AGC | CTG | GCA | TTG | GCG | AGG | CCC | AAG | AGC | AGT | GAT | GTG | TAC | GTG | TCT | 494 |
|---|---|---|---|---|---|---|---|---|---|---|---|---|---|---|---|---|
| Asp | Ser | Leu | Ala<br>125 | Leu | Ala | Arg | Pro | Lys<br>130 | Ser | Ser | Asp | Val | Tyr<br>135 | Val | Ser | |

| TAC | GAC | TAT | GGA | AAA | TCA | TTC | AAG | AAA | ATT | TCA | GAC | AAG | TTA | AAC | TTT | 542 |
|---|---|---|---|---|---|---|---|---|---|---|---|---|---|---|---|---|
| Tyr | Asp | Tyr<br>140 | Gly | Lys | Ser | Phe | Lys<br>145 | Lys | Ile | Ser | Asp | Lys<br>150 | Leu | Asn | Phe | |

| GGC | TTG | GGA | AAT | AGG | AGT | GAA | GCT | GTT | ATC | GCC | CAG | TTC | TAC | CAC | AGC | 590 |
|---|---|---|---|---|---|---|---|---|---|---|---|---|---|---|---|---|
| Gly | Leu<br>155 | Gly | Asn | Arg | Ser | Glu<br>160 | Ala | Val | Ile | Ala | Gln<br>165 | Phe | Tyr | His | Ser<br>170 | |

| CCT | GCG | GAC | AAC | AAG | CGG | TAC | ATC | TTT | GCA | GAC | GCT | TAT | GCC | CAG | TAC | 638 |
|---|---|---|---|---|---|---|---|---|---|---|---|---|---|---|---|---|
| Pro | Ala | Asp | Asn | Lys<br>175 | Arg | Tyr | Ile | Phe | Ala<br>180 | Asp | Ala | Tyr | Ala | Gln<br>185 | Tyr | |

| CTC | TGG | ATC | ACG | TTT | GAC | TTC | TGC | AAC | ACT | CTT | CAA | GGC | TTT | TCC | ATC | 686 |
|---|---|---|---|---|---|---|---|---|---|---|---|---|---|---|---|---|
| Leu | Trp | Ile | Thr<br>190 | Phe | Asp | Phe | Cys | Asn<br>195 | Thr | Leu | Gln | Gly | Phe<br>200 | Ser | Ile | |

| CCA | TTT | CGG | GCA | GCT | GAT | CTC | CTC | CTA | CAC | AGT | AAG | GCC | TCC | AAC | CTT | 734 |
|---|---|---|---|---|---|---|---|---|---|---|---|---|---|---|---|---|
| Pro | Phe | Arg<br>205 | Ala | Ala | Asp | Leu | Leu<br>210 | Leu | His | Ser | Lys | Ala<br>215 | Ser | Asn | Leu | |

| CTC | TTG | GGC | TTT | GAC | AGG | TCC | CAC | CCC | AAC | AAG | CAG | CTG | TGG | AAG | TCA | 782 |
|---|---|---|---|---|---|---|---|---|---|---|---|---|---|---|---|---|
| Leu | Leu<br>220 | Gly | Phe | Asp | Arg | Ser<br>225 | His | Pro | Asn | Lys | Gln<br>230 | Leu | Trp | Lys | Ser | |

| GAT | GAC | TTT | GGC | CAG | ACC | TGG | ATC | ATG | ATT | CAG | GAA | CAT | GTC | AAG | TCC | 830 |
|---|---|---|---|---|---|---|---|---|---|---|---|---|---|---|---|---|
| Asp<br>235 | Asp | Phe | Gly | Gln | Thr<br>240 | Trp | Ile | Met | Ile | Gln<br>245 | Glu | His | Val | Lys | Ser<br>250 | |

| TTT | TCT | TGG | GGA | ATT | GAT | CCC | TAT | GAC | AAA | CCA | AAT | ACC | ATC | TAC | ATT | 878 |
|---|---|---|---|---|---|---|---|---|---|---|---|---|---|---|---|---|
| Phe | Ser | Trp | Gly | Ile<br>255 | Asp | Pro | Tyr | Asp | Lys<br>260 | Pro | Asn | Thr | Ile | Tyr<br>265 | Ile | |

| GAA | CGA | CAC | GAA | CCC | TCT | GGC | TAC | TCC | ACT | GTC | TTC | CGA | AGT | ACA | GAT | 926 |
|---|---|---|---|---|---|---|---|---|---|---|---|---|---|---|---|---|
| Glu | Arg | His | Glu<br>270 | Pro | Ser | Gly | Tyr | Ser<br>275 | Thr | Val | Phe | Arg | Ser<br>280 | Thr | Asp | |

| TTC | TTC | CAG | TCC | CGG | GAA | AAC | CAG | GAA | GTG | ATC | CTT | GAG | GAA | GTG | AGA | 974 |
|---|---|---|---|---|---|---|---|---|---|---|---|---|---|---|---|---|
| Phe | Phe | Gln<br>285 | Ser | Arg | Glu | Asn | Gln<br>290 | Glu | Val | Ile | Leu | Glu<br>295 | Glu | Val | Arg | |

| GAT | TTT | CAG | CTT | CGG | GAC | AAG | TAC | ATG | TTT | GCT | ACA | AAG | GTG | GTG | CAT | 1022 |
|---|---|---|---|---|---|---|---|---|---|---|---|---|---|---|---|---|
| Asp | Phe | Gln | Leu | Arg | Asp | Lys | Tyr | Met | Phe | Ala | Thr | Lys | Val | Val | His | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 300 |     |     |     |     | 305 |     |     |     |     |     | 310 |     |     |      |
| CTC | TTG | GGC | AGT | GAA | CAG | CAG | TCT | TCT | GTC | CAG | CTC | TGG | GTC | TCC | TTT | 1070 |
| Leu | Leu | Gly | Ser | Glu | Gln | Gln | Ser | Ser | Val | Gln | Leu | Trp | Val | Ser | Phe |      |
| 315 |     |     |     |     | 320 |     |     |     |     | 325 |     |     |     |     | 330 |      |
| GGC | CGG | AAG | CCC | ATG | AGA | GCA | GCC | CAG | TTT | GTC | ACA | AGA | CAT | CCT | ATT | 1118 |
| Gly | Arg | Lys | Pro | Met | Arg | Ala | Ala | Gln | Phe | Val | Thr | Arg | His | Pro | Ile |      |
|     |     |     |     | 335 |     |     |     |     | 340 |     |     |     |     | 345 |     |      |
| AAT | GAA | TAT | TAC | ATC | GCA | GAT | GCC | TCC | GAG | GAC | CAG | GTG | TTT | GTG | TGT | 1166 |
| Asn | Glu | Tyr | Tyr | Ile | Ala | Asp | Ala | Ser | Glu | Asp | Gln | Val | Phe | Val | Cys |      |
|     |     |     | 350 |     |     |     |     | 355 |     |     |     |     | 360 |     |     |      |
| GTC | AGC | CAC | AGT | AAC | AAC | CGC | ACC | AAT | TTA | TAC | ATC | TCA | GAG | GCA | GAG | 1214 |
| Val | Ser | His | Ser | Asn | Asn | Arg | Thr | Asn | Leu | Tyr | Ile | Ser | Glu | Ala | Glu |      |
|     |     | 365 |     |     |     |     | 370 |     |     |     |     | 375 |     |     |     |      |
| GGG | CTG | AAG | TTC | TCC | CTG | TCC | TTG | GAG | AAC | GTG | CTC | TAT | TAC | AGC | CCA | 1262 |
| Gly | Leu | Lys | Phe | Ser | Leu | Ser | Leu | Glu | Asn | Val | Leu | Tyr | Tyr | Ser | Pro |      |
|     | 380 |     |     |     |     | 385 |     |     |     |     | 390 |     |     |     |     |      |
| GGA | GGG | GCC | GGC | AGT | GAC | ACC | TTG | GTG | AGG | TAT | TTT | GCA | AAT | GAA | CCA | 1310 |
| Gly | Gly | Ala | Gly | Ser | Asp | Thr | Leu | Val | Arg | Tyr | Phe | Ala | Asn | Glu | Pro |      |
| 395 |     |     |     |     | 400 |     |     |     |     | 405 |     |     |     |     | 410 |      |
| TTT | GCT | GAC | TTC | CAC | CGA | GTG | GAA | GGA | TTG | CAA | GGA | GTC | TAC | ATT | GCT | 1358 |
| Phe | Ala | Asp | Phe | His | Arg | Val | Glu | Gly | Leu | Gln | Gly | Val | Tyr | Ile | Ala |      |
|     |     |     |     | 415 |     |     |     |     | 420 |     |     |     |     | 425 |     |      |
| ACT | CTG | ATT | AAT | GGT | TCT | ATG | AAT | GAG | GAG | AAC | ATG | AGA | TCG | GTC | ATC | 1406 |
| Thr | Leu | Ile | Asn | Gly | Ser | Met | Asn | Glu | Glu | Asn | Met | Arg | Ser | Val | Ile |      |
|     |     |     | 430 |     |     |     |     | 435 |     |     |     |     | 440 |     |     |      |
| ACC | TTT | GAC | AAA | GGG | GGA | ACC | TGG | GAG | TTT | CTT | CAG | GCT | CCA | GCC | TTC | 1454 |
| Thr | Phe | Asp | Lys | Gly | Gly | Thr | Trp | Glu | Phe | Leu | Gln | Ala | Pro | Ala | Phe |      |
|     |     | 445 |     |     |     |     | 450 |     |     |     |     | 455 |     |     |     |      |
| ACG | GGA | TAT | GGA | GAG | AAA | ATC | AAT | TGT | GAG | CTT | TCC | CAG | GGC | TGT | TCC | 1502 |
| Thr | Gly | Tyr | Gly | Glu | Lys | Ile | Asn | Cys | Glu | Leu | Ser | Gln | Gly | Cys | Ser |      |
|     | 460 |     |     |     |     | 465 |     |     |     |     | 470 |     |     |     |     |      |
| CTT | CAT | CTG | GCT | CAG | CGC | CTC | AGT | CAG | CTC | CTC | AAC | CTC | CAG | CTC | CGG | 1550 |
| Leu | His | Leu | Ala | Gln | Arg | Leu | Ser | Gln | Leu | Leu | Asn | Leu | Gln | Leu | Arg |      |
| 475 |     |     |     |     | 480 |     |     |     |     | 485 |     |     |     |     | 490 |      |
| AGA | ATG | CCC | ATC | CTG | TCC | AAG | GAG | TCG | GCT | CCA | GGC | CTC | ATC | ATC | GCC | 1598 |
| Arg | Met | Pro | Ile | Leu | Ser | Lys | Glu | Ser | Ala | Pro | Gly | Leu | Ile | Ile | Ala |      |
|     |     |     |     | 495 |     |     |     |     | 500 |     |     |     |     | 505 |     |      |
| ACT | GGC | TCA | GTG | GGA | AAG | AAC | TTG | GCT | AGC | AAG | ACA | AAC | GTG | TAC | ATC | 1646 |
| Thr | Gly | Ser | Val | Gly | Lys | Asn | Leu | Ala | Ser | Lys | Thr | Asn | Val | Tyr | Ile |      |
|     |     |     | 510 |     |     |     |     | 515 |     |     |     |     | 520 |     |     |      |
| TCT | AGC | AGT | GCT | GGA | GCC | AGG | TGG | CGA | GAG | GCA | CTT | CCT | GGA | CCT | CAC | 1694 |
| Ser | Ser | Ser | Ala | Gly | Ala | Arg | Trp | Arg | Glu | Ala | Leu | Pro | Gly | Pro | His |      |
|     |     | 525 |     |     |     |     | 530 |     |     |     |     | 535 |     |     |     |      |
| TAC | TAC | ACA | TGG | GGA | GAC | CAC | GGC | GGA | ATC | ATC | ACG | GCC | ATT | GCC | CAG | 1742 |
| Tyr | Tyr | Thr | Trp | Gly | Asp | His | Gly | Gly | Ile | Ile | Thr | Ala | Ile | Ala | Gln |      |
|     | 540 |     |     |     |     | 545 |     |     |     |     | 550 |     |     |     |     |      |
| GGC | ATG | GAA | ACC | AAC | GAG | CTA | AAA | TAC | AGT | ACC | AAT | GAA | GGG | GAG | ACC | 1790 |
| Gly | Met | Glu | Thr | Asn | Glu | Leu | Lys | Tyr | Ser | Thr | Asn | Glu | Gly | Glu | Thr |      |
| 555 |     |     |     |     | 560 |     |     |     |     | 565 |     |     |     |     | 570 |      |
| TGG | AAA | ACA | TTC | ATC | TTC | TCT | GAG | AAG | CCA | GTG | TTT | GTG | TAT | GGC | CTC | 1838 |
| Trp | Lys | Thr | Phe | Ile | Phe | Ser | Glu | Lys | Pro | Val | Phe | Val | Tyr | Gly | Leu |      |
|     |     |     |     | 575 |     |     |     |     | 580 |     |     |     |     | 585 |     |      |
| CTC | ACA | GAA | CCT | GGG | GAG | AAG | AGC | ACT | GTC | TTC | ACC | ATC | TTT | GGC | TCG | 1886 |
| Leu | Thr | Glu | Pro | Gly | Glu | Lys | Ser | Thr | Val | Phe | Thr | Ile | Phe | Gly | Ser |      |
|     |     |     | 590 |     |     |     |     | 595 |     |     |     |     | 600 |     |     |      |
| AAC | AAA | GAG | AAT | GTC | CAC | AGC | TGG | CTG | ATC | CTC | CAG | GTC | AAT | GCC | ACG | 1934 |
| Asn | Lys | Glu | Asn | Val | His | Ser | Trp | Leu | Ile | Leu | Gln | Val | Asn | Ala | Thr |      |
|     | 605 |     |     |     |     | 610 |     |     |     |     | 615 |     |     |     |     |      |
| GAT | GCC | TTG | GGA | GTT | CCC | TGC | ACA | GAG | AAT | GAC | TAC | AAG | CTG | TGG | TCA | 1982 |
| Asp | Ala | Leu | Gly | Val | Pro | Cys | Thr | Glu | Asn | Asp | Tyr | Lys | Leu | Trp | Ser |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | 620 |     |     |     | 625 |     |     |     |     | 630 |     |     |     |     |     |      |
| CCA | TCT | GAT | GAG | CGG | GGG | AAT | GAG | TGT | TTG | CTG | GGA | CAC | AAG | ACT | GTT | 2030 |
| Pro | Ser | Asp | Glu | Arg | Gly | Asn | Glu | Cys | Leu | Leu | Gly | His | Lys | Thr | Val |      |
| 635 |     |     |     | 640 |     |     |     |     | 645 |     |     |     |     |     | 650 |      |
| TTC | AAA | CGG | CGG | ACC | CCC | CAT | GCC | ACA | TGC | TTC | AAT | GGA | GAG | GAC | TTT | 2078 |
| Phe | Lys | Arg | Arg | Thr | Pro | His | Ala | Thr | Cys | Phe | Asn | Gly | Glu | Asp | Phe |      |
|     |     |     |     | 655 |     |     |     |     | 660 |     |     |     |     | 665 |     |      |
| GAC | AGG | CCG | GTG | GTC | GTG | TCC | AAC | TGC | TCC | TGC | ACC | CGG | GAG | GAC | TAT | 2126 |
| Asp | Arg | Pro | Val | Val | Val | Ser | Asn | Cys | Ser | Cys | Thr | Arg | Glu | Asp | Tyr |      |
|     |     |     | 670 |     |     |     |     | 675 |     |     |     |     | 680 |     |     |      |
| GAG | TGT | GAC | TTC | GGT | TTC | AAG | ATG | AGT | GAA | GAT | TTG | TCA | TTA | GAG | GTT | 2174 |
| Glu | Cys | Asp | Phe | Gly | Phe | Lys | Met | Ser | Glu | Asp | Leu | Ser | Leu | Glu | Val |      |
|     |     | 685 |     |     |     | 690 |     |     |     |     |     |     | 690 |     |     |      |
| TGT | GTT | CCA | GAT | CCG | GAA | TTT | TCT | GGA | AAG | TCA | TAC | TCC | CCT | CCT | GTG | 2222 |
| Cys | Val | Pro | Asp | Pro | Glu | Phe | Ser | Gly | Lys | Ser | Tyr | Ser | Pro | Pro | Val |      |
|     | 700 |     |     |     |     | 705 |     |     |     |     | 710 |     |     |     |     |      |
| CCT | TGC | CCT | GTG | GGT | TCT | ACT | TAC | AGG | AGA | ACG | AGA | GGC | TAC | CGG | AAG | 2270 |
| Pro | Cys | Pro | Val | Gly | Ser | Thr | Tyr | Arg | Arg | Thr | Arg | Gly | Tyr | Arg | Lys |      |
| 715 |     |     |     |     | 720 |     |     |     |     | 725 |     |     |     |     | 730 |      |
| ATT | TCT | GGG | GAC | ACT | TGT | AGC | GGA | GGA | GAT | GTT | GAA | GCG | CGA | CTG | GAA | 2318 |
| Ile | Ser | Gly | Asp | Thr | Cys | Ser | Gly | Gly | Asp | Val | Glu | Ala | Arg | Leu | Glu |      |
|     |     |     |     | 735 |     |     |     |     | 740 |     |     |     |     | 745 |     |      |
| GGA | GAG | CTG | GTC | CCC | TGT | CCC | CTG | GCA | GAA | GAG | AAC | GAG | TTC | ATT | CTG | 2366 |
| Gly | Glu | Leu | Val | Pro | Cys | Pro | Leu | Ala | Glu | Glu | Asn | Glu | Phe | Ile | Leu |      |
|     |     |     | 750 |     |     |     |     | 755 |     |     |     |     | 760 |     |     |      |
| TAT | GCT | GTG | AGG | AAA | TCC | ATC | TAC | CGC | TAT | GAC | CTG | GCC | TCG | GGA | GCC | 2414 |
| Tyr | Ala | Val | Arg | Lys | Ser | Ile | Tyr | Arg | Tyr | Asp | Leu | Ala | Ser | Gly | Ala |      |
|     |     | 765 |     |     |     | 770 |     |     |     |     | 775 |     |     |     |     |      |
| ACC | GAG | CAG | TTG | CCT | CTC | ACC | GGG | CTA | CGG | GCA | GCA | GTG | GCC | CTG | GAC | 2462 |
| Thr | Glu | Gln | Leu | Pro | Leu | Thr | Gly | Leu | Arg | Ala | Ala | Val | Ala | Leu | Asp |      |
| 780 |     |     |     |     | 785 |     |     |     |     | 790 |     |     |     |     |     |      |
| TTT | GAC | TAT | GAG | CAC | AAC | TGT | TTG | TAT | TGG | TCC | GAC | CTG | GCC | TTG | GAC | 2510 |
| Phe | Asp | Tyr | Glu | His | Asn | Cys | Leu | Tyr | Trp | Ser | Asp | Leu | Ala | Leu | Asp |      |
| 795 |     |     |     |     | 800 |     |     |     |     | 805 |     |     |     |     | 810 |      |
| GTC | ATC | CAG | CGC | CTC | TGT | TTG | AAT | GGA | AGC | ACA | GGG | CAA | GAG | GTG | ATC | 2558 |
| Val | Ile | Gln | Arg | Leu | Cys | Leu | Asn | Gly | Ser | Thr | Gly | Gln | Glu | Val | Ile |      |
|     |     |     |     | 815 |     |     |     |     | 820 |     |     |     |     | 825 |     |      |
| ATC | AAT | TCT | GGC | CTG | GAG | ACA | GTA | GAA | GCT | TTG | GCT | TTT | GAA | CCC | CTC | 2606 |
| Ile | Asn | Ser | Gly | Leu | Glu | Thr | Val | Glu | Ala | Leu | Ala | Phe | Glu | Pro | Leu |      |
|     |     |     | 830 |     |     |     |     | 835 |     |     |     |     | 840 |     |     |      |
| AGC | CAG | CTG | CTT | TAC | TGG | GTA | GAT | GCA | GGC | TTC | AAA | AAG | ATT | GAG | GTA | 2654 |
| Ser | Gln | Leu | Leu | Tyr | Trp | Val | Asp | Ala | Gly | Phe | Lys | Lys | Ile | Glu | Val |      |
|     |     | 845 |     |     |     | 850 |     |     |     |     | 855 |     |     |     |     |      |
| GCT | AAT | CCA | GAT | GGC | GAC | TTC | CGA | CTC | ACA | ATC | GTC | AAT | TCC | TCT | GTG | 2702 |
| Ala | Asn | Pro | Asp | Gly | Asp | Phe | Arg | Leu | Thr | Ile | Val | Asn | Ser | Ser | Val |      |
| 860 |     |     |     |     | 865 |     |     |     |     | 870 |     |     |     |     |     |      |
| CTT | GAT | CGT | CCC | AGG | GCT | CTG | GTC | CTC | GTG | CCC | CAA | GAG | GGG | GTG | ATG | 2750 |
| Leu | Asp | Arg | Pro | Arg | Ala | Leu | Val | Leu | Val | Pro | Gln | Glu | Gly | Val | Met |      |
| 875 |     |     |     |     | 880 |     |     |     |     | 885 |     |     |     |     | 890 |      |
| TTC | TGG | ACA | GAC | TGG | GGA | GAC | CTG | AAG | CCT | GGG | ATT | TAT | CGG | AGC | AAT | 2798 |
| Phe | Trp | Thr | Asp | Trp | Gly | Asp | Leu | Lys | Pro | Gly | Ile | Tyr | Arg | Ser | Asn |      |
|     |     |     |     | 895 |     |     |     |     | 900 |     |     |     |     | 905 |     |      |
| ATG | GAT | GGT | TCT | GCT | GCC | TAT | CAC | CTG | GTG | TCT | GAG | GAT | GTG | AAG | TGG | 2846 |
| Met | Asp | Gly | Ser | Ala | Ala | Tyr | His | Leu | Val | Ser | Glu | Asp | Val | Lys | Trp |      |
|     |     |     | 910 |     |     |     |     | 915 |     |     |     |     | 920 |     |     |      |
| CCC | AAT | GGC | ATC | TCT | GTG | GAC | GAC | CAG | TGG | ATT | TAC | TGG | ACG | GAT | GCC | 2894 |
| Pro | Asn | Gly | Ile | Ser | Val | Asp | Asp | Gln | Trp | Ile | Tyr | Trp | Thr | Asp | Ala |      |
|     |     | 925 |     |     |     | 930 |     |     |     |     | 935 |     |     |     |     |      |
| TAC | CTG | GAG | TGC | ATA | GAG | CGG | ATC | ACG | TTC | AGT | GGC | CAG | CAG | CGC | TCT | 2942 |
| Tyr | Leu | Glu | Cys | Ile | Glu | Arg | Ile | Thr | Phe | Ser | Gly | Gln | Gln | Arg | Ser |      |

-continued

| | | | | | | | | | | | | | | | |
|---|---|---|---|---|---|---|---|---|---|---|---|---|---|---|---|
| GTC | ATT | CTG | GAC | AAC | CTC | CCG | CAC | CCC | TAT | GCC | ATT | GCT | GTC | TTT | AAG | 2990
| Val | Ile | Leu | Asp | Asn | Leu | Pro | His | Pro | Tyr | Ala | Ile | Ala | Val | Phe | Lys |
| 955 | | | | | 960 | | | | | 965 | | | | | 970 |

| AAT | GAA | ATC | TAC | TGG | GAT | GAC | TGG | TCA | CAG | CTC | AGC | ATA | TTC | CGA | GCT | 3038
|---|---|---|---|---|---|---|---|---|---|---|---|---|---|---|---|
| Asn | Glu | Ile | Tyr | Trp | Asp | Asp | Trp | Ser | Gln | Leu | Ser | Ile | Phe | Arg | Ala |
| | | | | 975 | | | | | 980 | | | | | 985 | |

| TCC | AAA | TAC | AGT | GGG | TCC | CAG | ATG | GAG | ATT | CTG | GCA | AAC | CAG | CTC | ACG | 3086
|---|---|---|---|---|---|---|---|---|---|---|---|---|---|---|---|
| Ser | Lys | Tyr | Ser | Gly | Ser | Gln | Met | Glu | Ile | Leu | Ala | Asn | Gln | Leu | Thr |
| | | | | 990 | | | | | 995 | | | | | 1000 | |

| GGG | CTC | ATG | GAC | ATG | AAG | ATT | TTC | TAC | AAG | GGG | AAG | AAC | ACT | GGA | AGC | 3134
|---|---|---|---|---|---|---|---|---|---|---|---|---|---|---|---|
| Gly | Leu | Met | Asp | Met | Lys | Ile | Phe | Tyr | Lys | Gly | Lys | Asn | Thr | Gly | Ser |
| | | | 1005 | | | | | 1010 | | | | | 1015 | | |

| AAT | GCC | TGT | GTG | CCC | AGG | CCA | TGC | AGC | CTG | CTG | TGC | CTG | CCC | AAG | GCC | 3182
|---|---|---|---|---|---|---|---|---|---|---|---|---|---|---|---|
| Asn | Ala | Cys | Val | Pro | Arg | Pro | Cys | Ser | Leu | Leu | Cys | Leu | Pro | Lys | Ala |
| | | 1020 | | | | | 1025 | | | | | 1030 | | | |

| AAC | AAC | AGT | AGA | AGC | TGC | AGG | TGT | CCA | GAG | GAT | GTG | TCC | AGC | AGT | GTG | 3230
|---|---|---|---|---|---|---|---|---|---|---|---|---|---|---|---|
| Asn | Asn | Ser | Arg | Ser | Cys | Arg | Cys | Pro | Glu | Asp | Val | Ser | Ser | Ser | Val |
| 1035 | | | | | 1040 | | | | | 1045 | | | | | 1050 |

| CTT | CCA | TCA | GGG | GAC | CTG | ATG | TGT | GAC | TGC | CCT | CAG | GGC | TAT | CAG | CTC | 3278
|---|---|---|---|---|---|---|---|---|---|---|---|---|---|---|---|
| Leu | Pro | Ser | Gly | Asp | Leu | Met | Cys | Asp | Cys | Pro | Gln | Gly | Tyr | Gln | Leu |
| | | | | 1055 | | | | | 1060 | | | | | 1065 | |

| AAG | AAC | AAT | ACC | TGT | GTC | AAA | GAA | GAG | AAC | ACC | TGT | CTT | CGC | AAC | CAG | 3326
|---|---|---|---|---|---|---|---|---|---|---|---|---|---|---|---|
| Lys | Asn | Asn | Thr | Cys | Val | Lys | Glu | Glu | Asn | Thr | Cys | Leu | Arg | Asn | Gln |
| | | | 1070 | | | | | 1075 | | | | | 1080 | | |

| TAT | CGC | TGC | AGC | AAC | GGG | AAC | TGT | ATC | AAC | AGC | ATT | TGG | TGG | TGT | GAC | 3374
|---|---|---|---|---|---|---|---|---|---|---|---|---|---|---|---|
| Tyr | Arg | Cys | Ser | Asn | Gly | Asn | Cys | Ile | Asn | Ser | Ile | Trp | Trp | Cys | Asp |
| | | | 1085 | | | | | 1090 | | | | | 1095 | | |

| TTT | GAC | AAC | GAC | TGT | GGA | GAC | ATG | AGC | GAT | GAG | AGA | AAC | TGC | CCT | ACC | 3422
|---|---|---|---|---|---|---|---|---|---|---|---|---|---|---|---|
| Phe | Asp | Asn | Asp | Cys | Gly | Asp | Met | Ser | Asp | Glu | Arg | Asn | Cys | Pro | Thr |
| | 1100 | | | | | 1105 | | | | | 1110 | | | | |

| ACC | ATC | TGT | GAC | CTG | GAC | ACC | CAG | TTT | CGT | TGC | CAG | GAG | TCT | GGG | ACT | 3470
|---|---|---|---|---|---|---|---|---|---|---|---|---|---|---|---|
| Thr | Ile | Cys | Asp | Leu | Asp | Thr | Gln | Phe | Arg | Cys | Gln | Glu | Ser | Gly | Thr |
| 1115 | | | | | 1120 | | | | | 1125 | | | | | 1130 |

| TGT | ATC | CCA | CTG | TCC | TAT | AAA | TGT | GAC | CTT | GAG | GAT | GAC | TGT | GGA | GAC | 3518
|---|---|---|---|---|---|---|---|---|---|---|---|---|---|---|---|
| Cys | Ile | Pro | Leu | Ser | Tyr | Lys | Cys | Asp | Leu | Glu | Asp | Asp | Cys | Gly | Asp |
| | | | | 1135 | | | | | 1140 | | | | | 1145 | |

| AAC | AGT | GAT | GAA | AGT | CAT | TGT | GAA | ATG | CAC | CAG | TGC | CGG | AGT | GAC | GAG | 3566
|---|---|---|---|---|---|---|---|---|---|---|---|---|---|---|---|
| Asn | Ser | Asp | Glu | Ser | His | Cys | Glu | Met | His | Gln | Cys | Arg | Ser | Asp | Glu |
| | | | | 1150 | | | | | 1155 | | | | | 1160 | |

| TAC | AAC | TGC | AGT | TCC | GGC | ATG | TGC | ATC | CGC | TCC | TCC | TGG | GTA | TGT | GAC | 3614
|---|---|---|---|---|---|---|---|---|---|---|---|---|---|---|---|
| Tyr | Asn | Cys | Ser | Ser | Gly | Met | Cys | Ile | Arg | Ser | Ser | Trp | Val | Cys | Asp |
| | | | 1165 | | | | | 1170 | | | | | 1175 | | |

| GGG | GAC | AAC | GAC | TGC | AGG | GAC | TGG | TCT | GAT | GAA | GCC | AAC | TGT | ACC | GCC | 3662
|---|---|---|---|---|---|---|---|---|---|---|---|---|---|---|---|
| Gly | Asp | Asn | Asp | Cys | Arg | Asp | Trp | Ser | Asp | Glu | Ala | Asn | Cys | Thr | Ala |
| | | 1180 | | | | | 1185 | | | | | 1190 | | | |

| ATC | TAT | CAC | ACC | TGT | GAG | GCC | TCC | AAC | TTC | CAG | TGC | CGA | AAC | GGG | CAC | 3710
|---|---|---|---|---|---|---|---|---|---|---|---|---|---|---|---|
| Ile | Tyr | His | Thr | Cys | Glu | Ala | Ser | Asn | Phe | Gln | Cys | Arg | Asn | Gly | His |
| 1195 | | | | | 1200 | | | | | 1205 | | | | | 1210 |

| TGC | ATC | CCC | CAG | CGG | TGG | GCG | TGT | GAC | GGG | GAT | ACG | GAC | TGC | CAG | GAT | 3758
|---|---|---|---|---|---|---|---|---|---|---|---|---|---|---|---|
| Cys | Ile | Pro | Gln | Arg | Trp | Ala | Cys | Asp | Gly | Asp | Thr | Asp | Cys | Gln | Asp |
| | | | | 1215 | | | | | 1220 | | | | | 1225 | |

| GGT | TCC | GAT | GAG | GAT | CCA | GTC | AAC | TGT | GAG | AAG | AAG | TGC | AAT | GGA | TTC | 3806
|---|---|---|---|---|---|---|---|---|---|---|---|---|---|---|---|
| Gly | Ser | Asp | Glu | Asp | Pro | Val | Asn | Cys | Glu | Lys | Lys | Cys | Asn | Gly | Phe |
| | | | | 1230 | | | | | 1235 | | | | | 1240 | |

| CGC | TGC | CCA | AAC | GGC | ACT | TGC | ATC | CCA | TCC | AGC | AAA | CAT | TGT | GAT | GGT | 3854
|---|---|---|---|---|---|---|---|---|---|---|---|---|---|---|---|
| Arg | Cys | Pro | Asn | Gly | Thr | Cys | Ile | Pro | Ser | Ser | Lys | His | Cys | Asp | Gly |
| | | | 1245 | | | | | 1250 | | | | | 1255 | | |

| CTG | CGT | GAT | TGC | TCT | GAT | GGC | TCC | GAT | GAA | CAG | CAC | TGC | GAG | CCC | CTC | 3902
|---|---|---|---|---|---|---|---|---|---|---|---|---|---|---|---|
| Leu | Arg | Asp | Cys | Ser | Asp | Gly | Ser | Asp | Glu | Gln | His | Cys | Glu | Pro | Leu |

```
                 1260                      1265                      1270

TGT ACG CAC TTC ATG GAC TTT GTG TGT AAG AAC CGC CAG CAG TGC CTG         3950
Cys Thr His Phe Met Asp Phe Val Cys Lys Asn Arg Gln Gln Cys Leu
1275                1280                    1285                1290

TTC CAC TCC ATG GTC TGT GAC GGA ATC ATC CAG TGC CGC GAC GGG TCC         3998
Phe His Ser Met Val Cys Asp Gly Ile Ile Gln Cys Arg Asp Gly Ser
            1295                    1300                    1305

GAT GAG GAT GCG GCG TTT GCA GGA TGC TCC CAA GAT CCT GAG TTC CAC         4046
Asp Glu Asp Ala Ala Phe Ala Gly Cys Ser Gln Asp Pro Glu Phe His
                1310                    1315                    1320

AAG GTA TGT GAT GAG TTC GGT TTC CAG TGT CAG AAT GGA GTG TGC ATC         4094
Lys Val Cys Asp Glu Phe Gly Phe Gln Cys Gln Asn Gly Val Cys Ile
1325                    1330                    1335

AGT TTG ATT TGG AAG TGC GAC GGG ATG GAT GAT TGC GGC GAT TAT TCT         4142
Ser Leu Ile Trp Lys Cys Asp Gly Met Asp Asp Cys Gly Asp Tyr Ser
    1340                    1345                    1350

GAT GAA GCC AAC TGC GAA AAC CCC ACA GAA GCC CCA AAC TGC TCC CGC         4190
Asp Glu Ala Asn Cys Glu Asn Pro Thr Glu Ala Pro Asn Cys Ser Arg
1355                1360                    1365                1370

TAC TTC CAG TTT CGG TGT GAG AAT GGC CAC TGC ATC CCC AAC AGA TGG         4238
Tyr Phe Gln Phe Arg Cys Glu Asn Gly His Cys Ile Pro Asn Arg Trp
                    1375                    1380                    1385

AAA TGT GAC AGG GAG AAC GAC TGT GGG GAC TGG TCT GAT GAG AAG GAT         4286
Lys Cys Asp Arg Glu Asn Asp Cys Gly Asp Trp Ser Asp Glu Lys Asp
                1390                    1395                    1400

TGT GGA GAT TCA CAT ATT CTT CCC TTC TCG ACT CCT GGG CCC TCC ACG         4334
Cys Gly Asp Ser His Ile Leu Pro Phe Ser Thr Pro Gly Pro Ser Thr
                1405                    1410                    1415

TGT CTG CCC AAT TAC TAC CGC TGC AGC AGT GGG ACC TGC GTG ATG GAC         4382
Cys Leu Pro Asn Tyr Tyr Arg Cys Ser Ser Gly Thr Cys Val Met Asp
            1420                    1425                    1430

ACC TGG GTG TGC GAC GGG TAC CGA GAT TGT GCA GAT GGC TCT GAC GAG         4430
Thr Trp Val Cys Asp Gly Tyr Arg Asp Cys Ala Asp Gly Ser Asp Glu
1435                    1440                    1445                1450

GAA GCC TGC CCC TTG CTT GCA AAC GTC ACT GCT GCC TCC ACT CCC ACC         4478
Glu Ala Cys Pro Leu Leu Ala Asn Val Thr Ala Ala Ser Thr Pro Thr
                    1455                    1460                    1465

CAA CTT GGG CGA TGT GAC CGA TTT GAG TTC GAA TGC CAC CAA CCG AAG         4526
Gln Leu Gly Arg Cys Asp Arg Phe Glu Phe Glu Cys His Gln Pro Lys
                1470                    1475                    1480

ACG TGT ATT CCC AAC TGG AAG CGC TGT GAC GGC CAC CAA GAT TGC CAG         4574
Thr Cys Ile Pro Asn Trp Lys Arg Cys Asp Gly His Gln Asp Cys Gln
            1485                    1490                    1495

GAT GGC CGG GAC GAG GCC AAT TGC CCC ACA CAC AGC ACC TTG ACT TGC         4622
Asp Gly Arg Asp Glu Ala Asn Cys Pro Thr His Ser Thr Leu Thr Cys
1500                    1505                    1510

ATG AGC AGG GAG TTC CAG TGC GAG GAC GGG GAG GCC TGC ATT GTG CTC         4670
Met Ser Arg Glu Phe Gln Cys Glu Asp Gly Glu Ala Cys Ile Val Leu
1515                    1520                    1525                1530

TCG GAG CGC TGC GAC GGC TTC CTG GAC TGC TCG GAC GAG AGC GAT GAA         4718
Ser Glu Arg Cys Asp Gly Phe Leu Asp Cys Ser Asp Glu Ser Asp Glu
                1535                    1540                    1545

AAG GCC TGC AGT GAT GAG TTG ACT GTG TAC AAA GTA CAG AAT CTT CAG         4766
Lys Ala Cys Ser Asp Glu Leu Thr Val Tyr Lys Val Gln Asn Leu Gln
                1550                    1555                    1560

TGG ACA GCT GAC TTC TCT GGG GAT GTG ACT TTG ACC TGG ATG AGG CCC         4814
Trp Thr Ala Asp Phe Ser Gly Asp Val Thr Leu Thr Trp Met Arg Pro
            1565                    1570                    1575

AAA AAA ATG CCC TCT GCA TCT TGT GTA TAT AAT GTC TAC TAC AGG GTG         4862
Lys Lys Met Pro Ser Ala Ser Cys Val Tyr Asn Val Tyr Tyr Arg Val
```

|  |  |  |  |  |  |  |  |  |  |  |  |  |  |  |  |
|---|---|---|---|---|---|---|---|---|---|---|---|---|---|---|---|
| GTT | GGA | GAG | AGC | ATA | TGG | AAG | ACT | CTG | GAG | ACC | CAC | AGC | AAT | AAG | ACA |
| Val | Gly | Glu | Ser | Ile | Trp | Lys | Thr | Leu | Glu | Thr | His | Ser | Asn | Lys | Thr |
| 1595 |  |  |  |  | 1600 |  |  |  |  | 1605 |  |  |  |  | 1610 |

Positions 1580, 1585, 1590 shown above; line ends at 4910.

```
                 1580                    1585                    1590
GTT GGA GAG AGC ATA TGG AAG ACT CTG GAG ACC CAC AGC AAT AAG ACA      4910
Val Gly Glu Ser Ile Trp Lys Thr Leu Glu Thr His Ser Asn Lys Thr
1595                1600                1605                1610

AAC ACT GTA TTA AAA GTC TTG AAA CCA GAT ACC ACG TAT CAG GTT AAA      4958
Asn Thr Val Leu Lys Val Leu Lys Pro Asp Thr Thr Tyr Gln Val Lys
                1615                1620                1625

GTA CAG GTT CAG TGT CTC AGC AAG GCA CAC AAC ACC AAT GAC TTT GTG      5006
Val Gln Val Gln Cys Leu Ser Lys Ala His Asn Thr Asn Asp Phe Val
                1630                1635                1640

ACC CTG AGG ACC CCA GAG GGA TTG CCA GAT GCC CCT CGA AAT CTC CAG      5054
Thr Leu Arg Thr Pro Glu Gly Leu Pro Asp Ala Pro Arg Asn Leu Gln
                1645                1650                1655

CTG TCA CTC CCC AGG GAA GCA GAA GGT GTG ATT GTA GGC CAC TGG GCT      5102
Leu Ser Leu Pro Arg Glu Ala Glu Gly Val Ile Val Gly His Trp Ala
1660]               1665                1670

CCT CCC ATC CAC ACC CAT GGC CTC ATC CGT GAG TAC ATT GTA GAA TAC      5150
Pro Pro Ile His Thr His Gly Leu Ile Arg Glu Tyr Ile Val Glu Tyr
1675                1680                1685                1690

AGC AGG AGT GGT TCC AAG ATG TGG GCC TCC CAG AGG GCT GCT AGT AAC      5198
Ser Arg Ser Gly Ser Lys Met Trp Ala Ser Gln Arg Ala Ala Ser Asn
                1695                1700                1705

TTT ACA GAA ATC AAG AAC TTA TTG GTC AAC ACT CTA TAC ACC GTC AGA      5246
Phe Thr Glu Ile Lys Asn Leu Leu Val Asn Thr Leu Tyr Thr Val Arg
                1710                1715                1720

GTG GCT GCG GTG ACT AGT CGT GGA ATA GGA AAC TGG AGC GAT TCT AAA      5294
Val Ala Ala Val Thr Ser Arg Gly Ile Gly Asn Trp Ser Asp Ser Lys
1725                1730                1735

TCC ATT ACC ACC ATA AAA GGA AAA GTG ATC CCA CCA CCA GAT ATC CAC      5342
Ser Ile Thr Thr Ile Lys Gly Lys Val Ile Pro Pro Pro Asp Ile His
1740                1745                1750

ATT GAC AGC TAT GGT GAA AAT TAT CTA AGC TTC ACC CTG ACC ATG GAG      5390
Ile Asp Ser Tyr Gly Glu Asn Tyr Leu Ser Phe Thr Leu Thr Met Glu
1755                1760                1765                1770

AGT GAT ATC AAG GTG AAT GGC TAT GTG GTG AAC CTT TTC TGG GCA TTT      5438
Ser Asp Ile Lys Val Asn Gly Tyr Val Val Asn Leu Phe Trp Ala Phe
                1775                1780                1785

GAC ACC CAC AAG CAA GAG AGG AGA ACT TTG AAC TTC CGA GGA AGC ATA      5486
Asp Thr His Lys Gln Glu Arg Arg Thr Leu Asn Phe Arg Gly Ser Ile
                1790                1795                1800

TTG TCA CAC AAA GTT GGC AAT CTG ACA GCT CAT ACA TCC TAT GAG ATT      5534
Leu Ser His Lys Val Gly Asn Leu Thr Ala His Thr Ser Tyr Glu Ile
                1805                1810                1815

TCT GCC TGG GCC AAG ACT GAC TTG GGG GAT AGC CCT CTG GCA TTT GAG      5582
Ser Ala Trp Ala Lys Thr Asp Leu Gly Asp Ser Pro Leu Ala Phe Glu
1820                1825                1830

CAT GTT ATG ACC AGA GGG GTT CGC CCA CCT GCA CCT AGC CTC AAG GCC      5630
His Val Met Thr Arg Gly Val Arg Pro Pro Ala Pro Ser Leu Lys Ala
1835                1840                1845                1850

AAA GCC ATC AAC CAG ACT GCA GTG GAA TGT ACC TGG ACC GGC CCC CGG      5678
Lys Ala Ile Asn Gln Thr Ala Val Glu Cys Thr Trp Thr Gly Pro Arg
                1855                1860                1865

AAT GTG GTT TAT GGT ATT TTC TAT GCC ACG TCC TTT CTT GAC CTC TAT      5726
Asn Val Val Tyr Gly Ile Phe Tyr Ala Thr Ser Phe Leu Asp Leu Tyr
                1870                1875                1880

CGC AAC CCG AAG AGC TTG ACT ACT TCA CTC CAC AAC AAG ACG GTC ATT      5774
Arg Asn Pro Lys Ser Leu Thr Thr Ser Leu His Asn Lys Thr Val Ile
                1885                1890                1895

GTC AGT AAG GAT GAG CAG TAT TTG TTT CTG GTC CGT GTA GTG GTA CCC      5822
Val Ser Lys Asp Glu Gln Tyr Leu Phe Leu Val Arg Val Val Val Pro
```

```
                    1900                      1905                      1910
TAC  CAG  GGG  CCA  TCC  TCT  GAC  TAC  GTT  GTA  GTG  AAG  ATG  ATC  CCG  GAC      5870
Tyr  Gln  Gly  Pro  Ser  Ser  Asp  Tyr  Val  Val  Val  Lys  Met  Ile  Pro  Asp
1915                universal 1920                     1925                1930

AGC  AGG  CTT  CCA  CCC  CGT  CAC  CTG  CAT  GTG  GTT  CAT  ACG  GGC  AAA  ACC      5918
Ser  Arg  Leu  Pro  Pro  Arg  His  Leu  His  Val  Val  His  Thr  Gly  Lys  Thr
                    1935                     1940                     1945

TCC  GTG  GTC  ATC  AAG  TGG  GAA  TCA  CCG  TAT  GAC  TCT  CCT  GAC  CAG  GAC      5966
Ser  Val  Val  Ile  Lys  Trp  Glu  Ser  Pro  Tyr  Asp  Ser  Pro  Asp  Gln  Asp
               1950                     1955                     1960

TTG  TTG  TAT  GCA  ATT  GCA  GTC  AAA  GAT  CTC  ATA  AGA  AAG  ACT  GAC  AGG      6014
Leu  Leu  Tyr  Ala  Ile  Ala  Val  Lys  Asp  Leu  Ile  Arg  Lys  Thr  Asp  Arg
          1965                     1970                     1975

AGC  TAC  AAA  GTA  AAA  TCC  CGT  AAC  AGC  ACT  GTG  GAA  TAC  ACC  CTT  AAC      6062
Ser  Tyr  Lys  Val  Lys  Ser  Arg  Asn  Ser  Thr  Val  Glu  Tyr  Thr  Leu  Asn
1980                     1985                     1990

AAG  TTG  GAG  CCT  GGC  GGG  AAA  TAC  CAC  ATC  ATT  GTC  CAA  CTG  GGG  AAC      6110
Lys  Leu  Glu  Pro  Gly  Gly  Lys  Tyr  His  Ile  Ile  Val  Gln  Leu  Gly  Asn
1995                     2000                     2005                     2010

ATG  AGC  AAA  GAT  TCC  AGC  ATA  AAA  ATT  ACC  ACA  GTT  TCA  TTA  TCA  GCA      6158
Met  Ser  Lys  Asp  Ser  Ser  Ile  Lys  Ile  Thr  Thr  Val  Ser  Leu  Ser  Ala
                    2015                     2020                     2025

CCT  GAT  GCC  TTA  AAA  ATC  ATA  ACA  GAA  AAT  GAT  CAT  GTT  CTT  CTG  TTT      6206
Pro  Asp  Ala  Leu  Lys  Ile  Ile  Thr  Glu  Asn  Asp  His  Val  Leu  Leu  Phe
               2030                     2035                     2040

TGG  AAA  AGC  CTG  GCT  TTA  AAG  GAA  AAG  CAT  TTT  AAT  GAA  AGC  AGG  GGC      6254
Trp  Lys  Ser  Leu  Ala  Leu  Lys  Glu  Lys  His  Phe  Asn  Glu  Ser  Arg  Gly
          2045                     2050                     2055

TAT  GAG  ATA  CAC  ATG  TTT  GAT  AGT  GCC  ATG  AAT  ATC  ACA  GCT  TAC  CTT      6302
Tyr  Glu  Ile  His  Met  Phe  Asp  Ser  Ala  Met  Asn  Ile  Thr  Ala  Tyr  Leu
2060                     2065                     2070

GGG  AAT  ACT  ACT  GAC  AAT  TTC  TTT  AAA  ATT  TCC  AAC  CTG  AAG  ATG  GGT      6350
Gly  Asn  Thr  Thr  Asp  Asn  Phe  Phe  Lys  Ile  Ser  Asn  Leu  Lys  Met  Gly
2075                     2080                     2085                     2090

CAT  AAT  TAC  ACG  TTC  ACC  GTC  CAA  GCA  AGA  TGC  CTT  TTT  GGC  AAC  CAG      6398
His  Asn  Tyr  Thr  Phe  Thr  Val  Gln  Ala  Arg  Cys  Leu  Phe  Gly  Asn  Gln
                    2095                     2100                     2105

ATC  TGT  GGG  GAG  CCT  GCC  ATC  CTG  CTG  TAC  GAT  GAG  CTG  GGG  TCT  GGT      6446
Ile  Cys  Gly  Glu  Pro  Ala  Ile  Leu  Leu  Tyr  Asp  Glu  Leu  Gly  Ser  Gly
               2110                     2115                     2120

GCA  GAT  GCA  TCT  GCA  ACG  CAG  GCT  GCC  AGA  TCT  ACG  GAT  GTT  GCT  GCT      6494
Ala  Asp  Ala  Ser  Ala  Thr  Gln  Ala  Ala  Arg  Ser  Thr  Asp  Val  Ala  Ala
          2125                     2130                     2135

GTG  GTG  GTG  CCC  ATC  TTA  TTC  CTG  ATA  CTG  CTG  AGC  CTG  GGG  GTG  GGG      6542
Val  Val  Val  Pro  Ile  Leu  Phe  Leu  Ile  Leu  Leu  Ser  Leu  Gly  Val  Gly
2140                     2145                     2150

TTT  GCC  ATC  CTG  TAC  ACG  AAG  CAC  CGG  AGG  CTG  CAG  AGC  AGC  TTC  ACC      6590
Phe  Ala  Ile  Leu  Tyr  Thr  Lys  His  Arg  Arg  Leu  Gln  Ser  Ser  Phe  Thr
2155                     2160                     2165                     2170

GCC  TTC  GCC  AAC  AGC  CAC  TAC  AGC  TCC  AGG  CTG  GGG  TCC  GCA  ATC  TTC      6638
Ala  Phe  Ala  Asn  Ser  His  Tyr  Ser  Ser  Arg  Leu  Gly  Ser  Ala  Ile  Phe
                    2175                     2180                     2185

TCC  TCT  GGG  GAT  GAC  CTG  GGG  GAA  GAT  GAT  GAA  GAT  GCC  CCT  ATG  ATA      6686
Ser  Ser  Gly  Asp  Asp  Leu  Gly  Glu  Asp  Asp  Glu  Asp  Ala  Pro  Met  Ile
               2190                     2195                     2200

ACT  GGA  TTT  TCA  GAT  GAC  GTC  CCC  ATG  GTG  ATA  GCC  TGA  AAGAGCTTTC          6735
Thr  Gly  Phe  Ser  Asp  Asp  Val  Pro  Met  Val  Ile  Ala  *
          2205                     2210

CTCACTAGAA  ACCAAATGGT  GTAAATATTT  TATTTGATAA  AGATAGTTGA  TGGTTTATTT              6795
```

TAAAAGATGC ACTTTGAGTT GCAATATGTT ATTTTTATAT GGGCCAAA 6843

(2) INFORMATION FOR SEQ ID NO:7:

(i) SEQUENCE CHARACTERISTICS:
        (A) LENGTH: 2214 amino acids
        (B) TYPE: amino acid
        (D) TOPOLOGY: linear (ii) MOLECULE TYPE: protein (xi) SEQUENCE DESCRIPTION: SEQ ID NO:7:

```
Met Ala Thr Arg Ser Ser Arg Arg Glu Ser Arg Leu Pro Phe Leu Phe
  1               5                  10                  15

Thr Leu Val Ala Leu Leu Pro Pro Gly Ala Leu Cys Glu Val Trp Thr
             20                  25                  30

Gln Arg Leu His Gly Gly Ser Ala Pro Leu Pro Gln Asp Arg Gly Phe
         35                  40                  45

Leu Val Val Gln Gly Asp Pro Arg Glu Leu Arg Leu Trp Ala Arg Gly
     50                  55                  60

Asp Ala Arg Gly Ala Ser Arg Ala Asp Glu Lys Pro Leu Arg Arg Lys
 65                  70                  75                  80

Arg Ser Ala Ala Leu Gln Pro Glu Pro Ile Lys Val Tyr Gly Gln Val
                 85                  90                  95

Ser Leu Asn Asp Ser His Asn Gln Met Val Val His Trp Ala Gly Glu
            100                 105                 110

Lys Ser Asn Val Ile Val Ala Leu Ala Arg Asp Ser Leu Ala Leu Ala
            115                 120                 125

Arg Pro Lys Ser Ser Asp Val Tyr Val Ser Tyr Asp Tyr Gly Lys Ser
        130                 135                 140

Phe Lys Lys Ile Ser Asp Lys Leu Asn Phe Gly Leu Gly Asn Arg Ser
145                 150                 155                 160

Glu Ala Val Ile Ala Gln Phe Tyr His Ser Pro Ala Asp Asn Lys Arg
                165                 170                 175

Tyr Ile Phe Ala Asp Ala Tyr Ala Gln Tyr Leu Trp Ile Thr Phe Asp
            180                 185                 190

Phe Cys Asn Thr Leu Gln Gly Phe Ser Ile Pro Phe Arg Ala Ala Asp
        195                 200                 205

Leu Leu Leu His Ser Lys Ala Ser Asn Leu Leu Leu Gly Phe Asp Arg
    210                 215                 220

Ser His Pro Asn Lys Gln Leu Trp Lys Ser Asp Phe Gly Gln Thr
225                 230                 235                 240

Trp Ile Met Ile Gln Glu His Val Lys Ser Phe Ser Trp Gly Ile Asp
                245                 250                 255

Pro Tyr Asp Lys Pro Asn Thr Ile Tyr Ile Glu Arg His Glu Pro Ser
            260                 265                 270

Gly Tyr Ser Thr Val Phe Arg Ser Thr Asp Phe Phe Gln Ser Arg Glu
        275                 280                 285

Asn Gln Glu Val Ile Leu Glu Glu Val Arg Asp Phe Gln Leu Arg Asp
    290                 295                 300

Lys Tyr Met Phe Ala Thr Lys Val Val His Leu Leu Gly Ser Glu Gln
305                 310                 315                 320

Gln Ser Ser Val Gln Leu Trp Val Ser Phe Gly Arg Lys Pro Met Arg
                325                 330                 335

Ala Ala Gln Phe Val Thr Arg His Pro Ile Asn Glu Tyr Tyr Ile Ala
            340                 345                 350
```

```
Asp Ala Ser Glu Asp Gln Val Phe Val Cys Val Ser His Ser Asn Asn
        355             360                 365
Arg Thr Asn Leu Tyr Ile Ser Glu Ala Glu Gly Leu Lys Phe Ser Leu
        370             375             380
Ser Leu Glu Asn Val Leu Tyr Tyr Ser Pro Gly Gly Ala Gly Ser Asp
385                 390             395                     400
Thr Leu Val Arg Tyr Phe Ala Asn Glu Pro Phe Ala Asp Phe His Arg
                405             410              415
Val Glu Gly Leu Gln Gly Val Tyr Ile Ala Thr Leu Ile Asn Gly Ser
            420             425             430
Met Asn Glu Glu Asn Met Arg Ser Val Ile Thr Phe Asp Lys Gly Gly
        435             440             445
Thr Trp Glu Phe Leu Gln Ala Pro Ala Phe Thr Gly Tyr Gly Glu Lys
    450             455             460
Ile Asn Cys Glu Leu Ser Gln Gly Cys Ser Leu His Leu Ala Gln Arg
465             470             475                     480
Leu Ser Gln Leu Leu Asn Leu Gln Leu Arg Arg Met Pro Ile Leu Ser
            485             490                     495
Lys Glu Ser Ala Pro Gly Leu Ile Ile Ala Thr Gly Ser Val Gly Lys
            500             505             510
Asn Leu Ala Ser Lys Thr Asn Val Tyr Ile Ser Ser Ala Gly Ala
        515             520             525
Arg Trp Arg Glu Ala Leu Pro Gly Pro His Tyr Tyr Thr Trp Gly Asp
530             535             540
His Gly Gly Ile Ile Thr Ala Ile Ala Gln Gly Met Glu Thr Asn Glu
545             550             555                     560
Leu Lys Tyr Ser Thr Asn Glu Gly Glu Thr Trp Lys Thr Phe Ile Phe
            565             570             575
Ser Glu Lys Pro Val Phe Val Tyr Gly Leu Leu Thr Glu Pro Gly Glu
            580             585             590
Lys Ser Thr Val Phe Thr Ile Phe Gly Ser Asn Lys Glu Asn Val His
        595             600             605
Ser Trp Leu Ile Leu Gln Val Asn Ala Thr Asp Ala Leu Gly Val Pro
    610             615             620
Cys Thr Glu Asn Asp Tyr Lys Leu Trp Ser Pro Ser Asp Glu Arg Gly
625             630             635                     640
Asn Glu Cys Leu Leu Gly His Lys Thr Val Phe Lys Arg Arg Thr Pro
            645             650             655
His Ala Thr Cys Phe Asn Gly Glu Asp Phe Asp Arg Pro Val Val Val
        660             665             670
Ser Asn Cys Ser Cys Thr Arg Glu Asp Tyr Glu Cys Asp Phe Gly Phe
        675             680             685
Lys Met Ser Glu Asp Leu Ser Leu Glu Val Cys Val Pro Asp Pro Glu
    690             695             700
Phe Ser Gly Lys Ser Tyr Ser Pro Val Pro Cys Pro Val Gly Ser
705             710             715             720
Thr Tyr Arg Arg Thr Arg Gly Tyr Arg Lys Ile Ser Gly Asp Thr Cys
                725             730             735
Ser Gly Gly Asp Val Glu Ala Arg Leu Glu Gly Glu Leu Val Pro Cys
            740             745             750
Pro Leu Ala Glu Glu Asn Glu Phe Ile Leu Tyr Ala Val Arg Lys Ser
        755             760             765
Ile Tyr Arg Tyr Asp Leu Ala Ser Gly Ala Thr Glu Gln Leu Pro Leu
    770             775             780
```

```
Thr  Gly  Leu  Arg  Ala  Ala  Val  Ala  Leu  Asp  Phe  Asp  Tyr  Glu  His  Asn
785            790                      795                           800

Cys  Leu  Tyr  Trp  Ser  Asp  Leu  Ala  Leu  Asp  Val  Ile  Gln  Arg  Leu  Cys
                    805                 810                           815

Leu  Asn  Gly  Ser  Thr  Gly  Gln  Glu  Val  Ile  Ile  Asn  Ser  Gly  Leu  Glu
                    820                 825                      830

Thr  Val  Glu  Ala  Leu  Ala  Phe  Glu  Pro  Leu  Ser  Gln  Leu  Leu  Tyr  Trp
               835                 840                      845

Val  Asp  Ala  Gly  Phe  Lys  Lys  Ile  Glu  Val  Ala  Asn  Pro  Asp  Gly  Asp
          850                 855                      860

Phe  Arg  Leu  Thr  Ile  Val  Asn  Ser  Ser  Val  Leu  Asp  Arg  Pro  Arg  Ala
865            870                      875                           880

Leu  Val  Leu  Val  Pro  Gln  Glu  Gly  Val  Met  Phe  Trp  Thr  Asp  Trp  Gly
                    885                 890                      895

Asp  Leu  Lys  Pro  Gly  Ile  Tyr  Arg  Ser  Asn  Met  Asp  Gly  Ser  Ala  Ala
               900                 905                      910

Tyr  His  Leu  Val  Ser  Glu  Asp  Val  Lys  Trp  Pro  Asn  Gly  Ile  Ser  Val
          915                 920                      925

Asp  Asp  Gln  Trp  Ile  Tyr  Trp  Thr  Asp  Ala  Tyr  Leu  Glu  Cys  Ile  Glu
930            935                      940

Arg  Ile  Thr  Phe  Ser  Gly  Gln  Gln  Arg  Ser  Val  Ile  Leu  Asp  Asn  Leu
945            950                      955                           960

Pro  His  Pro  Tyr  Ala  Ile  Ala  Val  Phe  Lys  Asn  Glu  Ile  Tyr  Trp  Asp
                    965                 970                      975

Asp  Trp  Ser  Gln  Leu  Ser  Ile  Phe  Arg  Ala  Ser  Lys  Tyr  Ser  Gly  Ser
               980                 985                      990

Gln  Met  Glu  Ile  Leu  Ala  Asn  Gln  Leu  Thr  Gly  Leu  Met  Asp  Met  Lys
          995                 1000                     1005

Ile  Phe  Tyr  Lys  Gly  Lys  Asn  Thr  Gly  Ser  Asn  Ala  Cys  Val  Pro  Arg
          1010                1015                     1020

Pro  Cys  Ser  Leu  Leu  Cys  Leu  Pro  Lys  Ala  Asn  Asn  Ser  Arg  Ser  Cys
1025                1030                1035                          1040

Arg  Cys  Pro  Glu  Asp  Val  Ser  Ser  Val  Leu  Pro  Ser  Gly  Asp  Leu
               1045                1050                     1055

Met  Cys  Asp  Cys  Pro  Gln  Gly  Tyr  Gln  Leu  Lys  Asn  Asn  Thr  Cys  Val
               1060                1065                     1070

Lys  Glu  Glu  Asn  Thr  Cys  Leu  Arg  Asn  Gln  Tyr  Arg  Cys  Ser  Asn  Gly
               1075                1080                     1085

Asn  Cys  Ile  Asn  Ser  Ile  Trp  Trp  Cys  Asp  Phe  Asp  Asn  Asp  Cys  Gly
               1090                1095                     1100

Asp  Met  Ser  Asp  Glu  Arg  Asn  Cys  Pro  Thr  Thr  Ile  Cys  Asp  Leu  Asp
1105                1110                1115                          1120

Thr  Gln  Phe  Arg  Cys  Gln  Glu  Ser  Gly  Thr  Cys  Ile  Pro  Leu  Ser  Tyr
               1125                1130                     1135

Lys  Cys  Asp  Leu  Glu  Asp  Asp  Cys  Gly  Asp  Asn  Ser  Asp  Glu  Ser  His
               1140                1145                     1150

Cys  Glu  Met  His  Gln  Cys  Arg  Ser  Asp  Glu  Tyr  Asn  Cys  Ser  Ser  Gly
               1155                1160                     1165

Met  Cys  Ile  Arg  Ser  Ser  Trp  Val  Cys  Asp  Gly  Asp  Asn  Asp  Cys  Arg
               1170                1175                     1180

Asp  Trp  Ser  Asp  Glu  Ala  Asn  Cys  Thr  Ala  Ile  Tyr  His  Thr  Cys  Glu
1185                1190                1195                          1200

Ala  Ser  Asn  Phe  Gln  Cys  Arg  Asn  Gly  His  Cys  Ile  Pro  Gln  Arg  Trp
```

```
                    1205                    1210                    1215
Ala  Cys  Asp  Gly  Asp  Thr  Asp  Cys  Gln  Asp  Gly  Ser  Asp  Glu  Asp  Pro
               1220                    1225                    1230
Val  Asn  Cys  Glu  Lys  Lys  Cys  Asn  Gly  Phe  Arg  Cys  Pro  Asn  Gly  Thr
          1235                    1240                    1245
Cys  Ile  Pro  Ser  Ser  Lys  His  Cys  Asp  Gly  Leu  Arg  Asp  Cys  Ser  Asp
     1250                    1255                    1260
Gly  Ser  Asp  Glu  Gln  His  Cys  Glu  Pro  Leu  Cys  Thr  His  Phe  Met  Asp
1265                    1270                    1275                    1280
Phe  Val  Cys  Lys  Asn  Arg  Gln  Gln  Cys  Leu  Phe  His  Ser  Met  Val  Cys
               1285                    1290                    1295
Asp  Gly  Ile  Ile  Gln  Cys  Arg  Asp  Gly  Ser  Asp  Glu  Asp  Ala  Ala  Phe
               1300                    1305                    1310
Ala  Gly  Cys  Ser  Gln  Asp  Pro  Glu  Phe  His  Lys  Val  Cys  Asp  Glu  Phe
               1315                    1320                    1325
Gly  Phe  Gln  Cys  Gln  Asn  Gly  Val  Cys  Ile  Ser  Leu  Ile  Trp  Lys  Cys
          1330                    1335                    1340
Asp  Gly  Met  Asp  Asp  Cys  Gly  Asp  Tyr  Ser  Asp  Glu  Ala  Asn  Cys  Glu
1345                    1350                    1355                    1360
Asn  Pro  Thr  Glu  Ala  Pro  Asn  Cys  Ser  Arg  Tyr  Phe  Gln  Phe  Arg  Cys
                    1365                    1370                    1375
Glu  Asn  Gly  His  Cys  Ile  Pro  Asn  Arg  Trp  Lys  Cys  Asp  Arg  Glu  Asn
               1380                    1385                    1390
Asp  Cys  Gly  Asp  Trp  Ser  Asp  Glu  Lys  Asp  Cys  Gly  Asp  Ser  His  Ile
          1395                    1400                    1405
Leu  Pro  Phe  Ser  Thr  Pro  Gly  Pro  Ser  Thr  Cys  Leu  Pro  Asn  Tyr  Tyr
          1410                    1415                    1420
Arg  Cys  Ser  Ser  Gly  Thr  Cys  Val  Met  Asp  Thr  Trp  Val  Cys  Asp  Gly
1425                    1430                    1435                    1440
Tyr  Arg  Asp  Cys  Ala  Asp  Gly  Ser  Asp  Glu  Glu  Ala  Cys  Pro  Leu  Leu
               1445                    1450                    1455
Ala  Asn  Val  Thr  Ala  Ala  Ser  Thr  Pro  Thr  Gln  Leu  Gly  Arg  Cys  Asp
               1460                    1465                    1470
Arg  Phe  Glu  Phe  Glu  Cys  His  Gln  Pro  Lys  Thr  Cys  Ile  Pro  Asn  Trp
     1475                    1480                    1485
Lys  Arg  Cys  Asp  Gly  His  Gln  Asp  Cys  Gln  Asp  Gly  Arg  Asp  Glu  Ala
          1490                    1495                    1500
Asn  Cys  Pro  Thr  His  Ser  Thr  Leu  Thr  Cys  Met  Ser  Arg  Glu  Phe  Gln
1505                    1510                    1515                    1520
Cys  Glu  Asp  Gly  Glu  Ala  Cys  Ile  Val  Leu  Ser  Glu  Arg  Cys  Asp  Gly
                    1525                    1530                    1535
Phe  Leu  Asp  Cys  Ser  Asp  Glu  Ser  Asp  Glu  Lys  Ala  Cys  Ser  Asp  Glu
               1540                    1545                    1550
Leu  Thr  Val  Tyr  Lys  Val  Gln  Asn  Leu  Gln  Trp  Thr  Ala  Asp  Phe  Ser
          1555                    1560                    1565
Gly  Asp  Val  Thr  Leu  Thr  Trp  Met  Arg  Pro  Lys  Lys  Met  Pro  Ser  Ala
          1570                    1575                    1580
Ser  Cys  Val  Tyr  Asn  Val  Tyr  Tyr  Arg  Val  Val  Gly  Glu  Ser  Ile  Trp
1585                    1590                    1595                    1600
Lys  Thr  Leu  Glu  Thr  His  Ser  Asn  Lys  Thr  Asn  Thr  Val  Leu  Lys  Val
          1605                    1610                    1615
Leu  Lys  Pro  Asp  Thr  Thr  Tyr  Gln  Val  Lys  Val  Gln  Val  Gln  Cys  Leu
          1620                    1625                    1630
```

```
Ser Lys Ala His Asn Thr Asn Asp Phe Val Thr Leu Arg Thr Pro Glu
        1635                1640                1645

Gly Leu Pro Asp Ala Pro Arg Asn Leu Gln Leu Ser Leu Pro Arg Glu
        1650                1655                1660

Ala Glu Gly Val Ile Val Gly His Trp Ala Pro Pro Ile His Thr His
1665                1670                1675                1680

Gly Leu Ile Arg Glu Tyr Ile Val Glu Tyr Ser Arg Ser Gly Ser Lys
                    1685                1690                1695

Met Trp Ala Ser Gln Arg Ala Ala Ser Asn Phe Thr Glu Ile Lys Asn
        1700                1705                1710

Leu Leu Val Asn Thr Leu Tyr Thr Val Arg Val Ala Ala Val Thr Ser
        1715                1720                1725

Arg Gly Ile Gly Asn Trp Ser Asp Ser Lys Ser Ile Thr Thr Ile Lys
        1730                1735                1740

Gly Lys Val Ile Pro Pro Asp Ile His Ile Asp Ser Tyr Gly Glu
1745                1750                1755                1760

Asn Tyr Leu Ser Phe Thr Leu Thr Met Glu Ser Asp Ile Lys Val Asn
                    1765                1770                1775

Gly Tyr Val Val Asn Leu Phe Trp Ala Phe Asp Thr His Lys Gln Glu
        1780                1785                1790

Arg Arg Thr Leu Asn Phe Arg Gly Ser Ile Leu Ser His Lys Val Gly
        1795                1800                1805

Asn Leu Thr Ala His Thr Ser Tyr Glu Ile Ser Ala Trp Ala Lys Thr
    1810                1815                1820

Asp Leu Gly Asp Ser Pro Leu Ala Phe Glu His Val Met Thr Arg Gly
1825                1830                1835                1840

Val Arg Pro Pro Ala Pro Ser Leu Lys Ala Lys Ala Ile Asn Gln Thr
                1845                1850                1855

Ala Val Glu Cys Thr Trp Thr Gly Pro Arg Asn Val Val Tyr Gly Ile
            1860                1865                1870

Phe Tyr Ala Thr Ser Phe Leu Asp Leu Tyr Arg Asn Pro Lys Ser Leu
        1875                1880                1885

Thr Thr Ser Leu His Asn Lys Thr Val Ile Val Ser Lys Asp Glu Gln
    1890                1895                1900

Tyr Leu Phe Leu Val Arg Val Val Val Pro Tyr Gln Gly Pro Ser Ser
1905                1910                1915                1920

Asp Tyr Val Val Val Lys Met Ile Pro Asp Ser Arg Leu Pro Pro Arg
            1925                1930                1935

His Leu His Val Val His Thr Gly Lys Thr Ser Val Val Ile Lys Trp
        1940                1945                1950

Glu Ser Pro Tyr Asp Ser Pro Asp Gln Asp Leu Leu Tyr Ala Ile Ala
        1955                1960                1965

Val Lys Asp Leu Ile Arg Lys Thr Asp Arg Ser Tyr Lys Val Lys Ser
        1970                1975                1980

Arg Asn Ser Thr Val Glu Tyr Thr Leu Asn Lys Leu Glu Pro Gly Gly
1985                1990                1995                2000

Lys Tyr His Ile Ile Val Gln Leu Gly Asn Met Ser Lys Asp Ser Ser
                2005                2010                2015

Ile Lys Ile Thr Thr Val Ser Leu Ser Ala Pro Asp Ala Leu Lys Ile
            2020                2025                2030

Ile Thr Glu Asn Asp His Val Leu Leu Phe Trp Lys Ser Leu Ala Leu
        2035                2040                2045

Lys Glu Lys His Phe Asn Glu Ser Arg Gly Tyr Glu Ile His Met Phe
2050                2055                2060
```

| | | | | | | | | | | | | | | |
|---|---|---|---|---|---|---|---|---|---|---|---|---|---|---|
| Asp | Ser | Ala | Met | Asn | Ile | Thr | Ala | Tyr | Leu | Gly | Asn | Thr | Thr | Asp | Asn |
| 2065 | | | | | 2070 | | | | | 2075 | | | | | 2080 |
| Phe | Phe | Lys | Ile | Ser | Asn | Leu | Lys | Met | Gly | His | Asn | Tyr | Thr | Phe | Thr |
| | | | | 2085 | | | | | 2090 | | | | | 2095 | |
| Val | Gln | Ala | Arg | Cys | Leu | Phe | Gly | Asn | Gln | Ile | Cys | Gly | Glu | Pro | Ala |
| | | | 2100 | | | | | 2105 | | | | | 2110 | | |
| Ile | Leu | Leu | Tyr | Asp | Glu | Leu | Gly | Ser | Gly | Ala | Asp | Ala | Ser | Ala | Thr |
| | | 2115 | | | | | 2120 | | | | | 2125 | | | |
| Gln | Ala | Ala | Arg | Ser | Thr | Asp | Val | Ala | Ala | Val | Val | Val | Pro | Ile | Leu |
| | 2130 | | | | | 2135 | | | | | 2140 | | | | |
| Phe | Leu | Ile | Leu | Leu | Ser | Leu | Gly | Val | Gly | Phe | Ala | Ile | Leu | Tyr | Thr |
| 2145 | | | | | 2150 | | | | | 2155 | | | | | 2160 |
| Lys | His | Arg | Arg | Leu | Gln | Ser | Ser | Phe | Thr | Ala | Phe | Ala | Asn | Ser | His |
| | | | | 2165 | | | | | 2170 | | | | | 2175 | |
| Tyr | Ser | Ser | Arg | Leu | Gly | Ser | Ala | Ile | Phe | Ser | Ser | Gly | Asp | Asp | Leu |
| | | | 2180 | | | | | 2185 | | | | | 2190 | | |
| Gly | Glu | Asp | Asp | Glu | Asp | Ala | Pro | Met | Ile | Thr | Gly | Phe | Ser | Asp | Asp |
| | | 2195 | | | | | 2200 | | | | | 2205 | | | |
| Val | Pro | Met | Val | Ile | Ala | | | | | | | | | | |
| 2210 | | | | | 2215 | | | | | | | | | | |

( 2 ) INFORMATION FOR SEQ ID NO:8:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="SYNTHETIC DNA LINKER"

( x i ) SEQUENCE DESCRIPTION: SEQ ID NO:8:

CCGAATTCGG    10

LDL RECEPTOR ANALOG PROTEIN AND DNA CODING THEREFOR

BACKGROUND OF THE INVENTION

1) Field of the Invention

The present invention relates to a novel LDL receptor analog protein having a structure similar to that of LDL receptors that are responsible for the homeostasis mechanism of intracellular cholesterol and extensively participates in serum lipid metabolism, which is a critical factor that triggers the onset of arteriosclerosis. The invention also relates to the gene coding for the protein.

2) Description of the Related Art

Abnormality in serum lipid metabolism is one of the most critical risk factors in the onset and progress of arteriosclerosis. Serum lipids, together with apolipoproteins, are transformed into lipoproteins primarily in the liver, secreted therefrom, transported by blood, and taken up by a variety of tissue cells.

Uptake of lipoproteins into cells occurs primarily by the mediation of receptors of respective lipoproteins. It is known that low density lipoproteins (LDL), which are taken into cells by specific membrane receptors, called LDL receptors, are metabolized within the cells and utilized as cell membrane components or similar substances. Detailed analysis of familial hyperchlolesterolemia, which is a genetic disease accompanied by notable hyperchlolesterolemia due to abnormality of LDL receptors, has clarified details of the mechanism of homeostasis achieved by LDL receptors with respect to intracellular cholesterol.

It has been suggested that living bodies have not only LDL receptors but also cell membrane receptors that recognize other lipoproteins. From analyses of WHHL rabbits, which are model animals lacking LDL receptors, it was found that receptors which takes principally apo-E-containing lipoproteins as ligands (remnant receptors) are present in the liver. It is also predicted that there may be HDL receptors whose ligands are high density lipoprotein (HDL). However, to date, details of the structures and functions of these receptors have not yet been elucidated. It has also been known that foaming of macrophages plays an active role in the formation of atherosclerosis, is deeply participated. Macrophages foam by taking up modified LDL, not normal LDL, which have undergone oxidation, acetylation, or glycation. There have recently been discovered receptors to modified LDL which are called scavenger receptors. The scavenger receptors have been identified to be membrane receptors that have a structure completely different from that of LDL receptors.

Recent research using molecular biological techniques has identified the genes of LRP (LDL receptor-associated protein), gp 330, and VLDL receptors. The receptors have been found to have structures very similar to those of LDL receptors. From analyses of these receptors, it is believed that a plurality of lipoprotein receptors are present in living bodies, and that they are closely related to lipid metabolism. LDL receptors studied in detail by Brown and Goldstein [Brown, M. S. and Goldstein, J. L. (1986) Science 232, 34–47] are known to play an important role in the homeostasis of lipoprotein metabolism in vivo, recognizing apo-B-100 and apo-E and taking primarily LDL as their ligands. Also, LRP, which is a macroprotein, has been found to primarily recognize apo-E and to take β-VLDL or chylomicron remnant as a ligand. Moreover, it has been recently reported that LRP takes an $\alpha_2$-macroglobulin/protease complex or a plasminogen activator/plasminogen activator inhibitor-1 complex as a ligand, and that LRP is a protein identical to the $\alpha_2$-macroglobulin receptor. When these findings are taken together, LRP is considered to have a wide variety of functions in living bodies [Herz, J., Hamann, U., Rogne, S., Myklebost, O., Gausepohl, H. and Stanley, K. K. (1989) EMBO J. 7(13), 4119–4127; Brown, M. S., Herz, J., Kowal, R. C. and Goldstein, J. L. (1991) Current Opinion in Lipidology 2, 65–72; Herz, J. (1993) Current Opinion in Lipidology 4, 107–113]. The gp 330, which was first identified as an antigen inducing rat Heymann nephritis, has been reported to have a ligand-binding capacity similar to that possessed by CRP $\alpha_2$-macroglobulin receptor [Raychowdhury, R., Niles, J. L., McCluskey, R. T. and Smith, J. A. (1989) Science 244, 1163–1165; Pietromonaco, S., Kerjaschki, D., Binder, S., Ullrich, R. and Farquhar, G. (1990) Proc. Natl. Acad. Sci. U.S.A. 87, 1811–1815]. In addition, recently discovered VLDL receptors, which are found to take VLDL as a ligand, are considered to have new functions including fatty acid metabolism, because they are predominantly found in tissues of the heart and muscles though they are rarely found in the liver [Takahashi, S., Kawarabayashi, Y., Nakai, T., Sakai, J. and Yamamoto, T. (1992) Proc. Natl. Acad. Sci. U.S.A. 89, 9252–9256].

Functions of these newly found receptors as lipoprotein receptors have been gradually elucidated through detailed in vitro analyses. However, significance of respective receptors in living bodies has mostly been left unknown. In addition, relations to remnant receptors, HDL receptors, etc., which have conventionally been identified or suggested by biochemical techniques, remain unknown. Presently, it is considered that these newly found receptors are products of genes different from those of the latter receptors. Thus, more lipoprotein receptors than originally guessed have become considered to participate in lipoprotein uptake into cells while interacting with each other to thereby function to maintain homeostasis of lipid metabolism in living bodies. However, from structural analyses of the genes of the aforementioned newly-identified receptors, it is predicted that the genes of these receptors that take lipoproteins as ligands are developed from the same gene from which LDL receptors was developed, and thus they are within the same genetic family. This suggests that lipoprotein receptors that have conventionally been proposed may have structures similar to those of LDL receptors.

Accordingly, an object of the present invention is to provide the gene of a novel receptor in the LDL receptor family, as well as a protein coded by the gene.

The present inventors conducted careful studies so as to attain the above object, and found that by using part of rabbit LDL receptor cDNA as a probe there can be obtained a DNA fragment coding for a peptide having a structure similar to that of LDL receptors. Moreover, when using part of the obtained cDNA as a probe, a cDNA fragment having a sequence similar to that of the cDNA can be obtained from the human tissue cDNA library. The present invention was accomplished based on these findings.

SUMMARY OF THE INVENTION

The present invention provides DNA having a nucleotide sequence shown by Sequence ID No. 1 or No. 5; an LDL receptor analog protein having an amino acid sequence coded by the DNA; a recombinant vector comprising the DNA and a replicable vector; transformant cells which harbor the recombinant vector; and a method for the production of the LDL receptor analog protein.

DESCRIPTION OF PREFERRED EMBODIMENT

The cDNA of the present invention may be prepared, for example, by the following process.

Briefly, the process includes the following steps. (1) Through the use of rabbit LDL receptor cDNA as a probe, positive clones are screened out of a rabbit liver cDNA library. (2) Recombinant DNA is prepared using the separated positive clones, and a cDNA fragment is cut out of the resultant recombinant DNA through a treatment using a restriction enzyme. The cDNA fragment is integrated into a plasmid vector. (3) Host cells are transformed using the obtained cDNA recombinant vector to thereby obtain transformant cells of the present invention. The obtained transformant cells are incubated so as to obtain a recombinant vector containing a DNA fragment of the present invention. The nucleotide sequence of the DNA fragment of the present invention contained in the resultant recombinant vector is determined. (4) In tissue of a living body, there is detected expression of mRNA indicated by the nucleotide sequence of the cDNA of the present invention by using RNA blot hybridization method. (5) Through use of a rabbit cDNA fragment as a probe, positive clones are screened out of a human tissue cDNA library, and the nucleotide sequence of the clones is determined. (6) A recombinant vector for expression is prepared using the cDNA of the present invention. Through use of the thus-obtained vector, host cells are transformed to thereby obtain the transformants of the present invention. (7) Ligands that are bound to protein expressed by the obtained transformants are detected by ligand blotting.

Each of the above-described steps will next be described.

(1) Screening for positive clones from a rabbit liver cDNA library:

A cDNA library may be prepared by the use of mRNA obtained from rabbit liver, reverse transcriptase, and a suitable vector, e.g., commercially available λgt10 vector.

A cDNA library thus prepared using λgt10 as a vector is subjected to a screening for positive clones by the application of a DNA hybridization method employing a cDNA probe, to thereby separate positive clones [Sambrook, J., Fritsch, E. F. and Maniatis, T. (1989) In: Molecular Cloning: A Laboratory Manual, pp 9.47–9.58, Cold Spring Harbor Laboratory Press].

An exemplary cDNA which may be used as a probe is rabbit LDL receptor cDNA. Positive clones may be detected by autoradiography employing a DNA probe labelled with a radioisotope ($^{32}P$).

(2) Preparation of a cDNA recombinant vector:

Recombinant vector λgt10 phage DNA is extracted from the isolated positive clones and purified. The resultant purified recombinant vector λgt10 phage DNA is digested with a restriction enzyme EcoRI, to thereby separate a cDNA fragment from the vector DNA. The obtained cDNA fragment is integrated with a plasmid vector for cloning that has been similarly digested with EcoRI, thereby obtaining a recombinant plasmid vector. An exemplary plasmid vector which may be used is pBluescript II.

(3) Recombinant vector, transformation of host cells using the recombinant vector, and preparation of DNA:

The obtained cDNA recombinant vector is introduced into a variety of host cells that are capable of utilizing the genetic marker possessed by the recombinant vector, to thereby transform the host cells. Host cells are not particularly limited, with E. coli being preferred. For example, a variety of variants of the E. coli K12 strain, e.g., HB-101, may be used. In order to introduce the recombinant vector into host cells, a competent cell method may be used in combination with a treatment with calcium.

The thus-obtained transformant cells are cultured in a selective medium in accordance with the genetic marker of the vector. The recombinant vector of the present invention is collected from the cultured cells. The DNA nucleotide sequence of the cDNA contained in the obtained recombinant vector can be determined through use of a dideoxy sequence method [Sanger, F., Nicklen, S. and Coulson, A. R. (1977) Proc. Natl. Acd. Sci. U.S.A. 74, 5463–5467].

(4) RNA blot hybridization:

The expression in tissue of mRNA, indicated by the nucleotide sequence of the cDNA of the present invention, is detected using RNA blot hybridization.

First, mRNA is prepared using rabbit tissue. Commercially available oligo(dT)cellulose column may be used for the preparation. In order to prepare mRNA from human tissue, there may be used a commercially available nylon membrane on which tissue poly(A)$^+$RNA from a variety of sources is present.

An exemplary probe is the rabbit cDNA obtained in the above-described step (3). mRNA may be detected by autoradiography employing a DNA probe labelled with a radioisotope ($^{32}P$).

(5) Screening of human tissue cDNA library for positive clones, and determination of nucleotide sequence:

An exemplary human tissue cDNA library which may be used is a commercially available human brain cDNA library.

Screening and nucleotide sequencing of the human brain cDNA library may be performed using a fragment of rabbit cDNA of the present invention as a probe in a manner similar to that used for the aforementioned rabbit liver cDNA library.

(6) Preparation of a recombinant vector for expression and transformation of host cells using the recombinant vector for expression:

In order to prepare an LDL receptor analog protein through use of cDNA of the present invention, the obtained cDNA and a vector for expression are first bonded to each other to thereby create a recombinant vector for expression. Vectors for expression which may be used for bonding are not particularly limited. For example, pBK-CMV may be used.

Host cells are transformed using the thus-obtained recombinant vector for expression, to thereby obtain a transformant cell of the present invention. The obtained transformant cell is cultured so as to obtain cells that are capable of expressing the protein of the invention. Host cells are not particularly limited. For example, CHO cells may be used. In order to introduce the recombinant vector for expression into host cells, a calcium phosphate method may be used.

The thus-prepared transformant cells are incubated in a selective medium in accordance with the genetic marker of the vector, so as to express the LDL receptor analog protein of the present invention.

(7) Ligand analysis of the protein by ligand blotting:

After the resultant transformant cells are incubated, the expressed LDL receptor analog protein is solubilized using a solubilizer, e.g., Triton X-100, to thereby obtain a membrane protein fraction. The fraction is separated using SDS-PAGE, and transferred onto, for example, a nitrocellulose membrane. Using a radio-labelled ($^{125}I$) lipoprotein as a probe, the analog protein can be detected by autoradiography. Exemplary lipoproteins which may be used include β-VLDL and LDL.

EXAMPLES

The present invention will next be described in detail by way of example, which should not be construed as limiting the invention.

Example 1

Preparation of a rabbit liver cDNA library:

From tissue of the liver of a male Japanese white rabbit, intact RNA was extracted through a guanidium thiocyanate/ cesium chloride method. The obtained intact RNA was subjected to an oligo (dT) cellulose column method to thereby obtain purified poly(A)$^+$RNA.

cDNA was synthesized in accordance with a method of Gubler and Hoffman [Gubler, U. and Hoffman, B. J. (1983) Gene 25, 263]. Briefly, cDNA was synthesized employing rabbit liver poly(A)$^+$RNA (as a template), a random primer, and moloney murine leukemia virus reverse transcriptase. The synthesized cDNA was transformed into double-stranded DNA using DNA polymerase I, and then subjected to an EcoRI methylase treatment. By the use of T4 DNA polymerase, the DNA was blunt-ended. The blunt-ended DNA was ligated to phosphorylated EcoRI linker pd (CCGAATTCGG) (SEQ ID NO:8) using a T4 DNA ligase, and the resultant ligated product was subjected to an additional digestion with EcoRI. cDNA fragments having a size not less than 1 kb were selected by agarose gel electrophoresis, and integrated into the EcoRI-digested site of λgt10 phage DNA using a T4 DNA ligase. The phage DNA was packaged in vitro, to thereby establish a rabbit liver cDNA library.

Example 2

Cloning of cDNA of receptors in the rabbit LDL receptor family:

The cDNA library (1,000,000 plaques) prepared in Example 1 was subjected to screening using a plaque hybridization method and employing as a probe a segment of the cDNA obtained from a ligand binding region, the functional region, of the rabbit LDL receptor. Hybridization was performed at 42° C. using 5×SSC, 30% formamide, 1% SDS, 5×Denhardt's, and 100 µg/ml salmon sperm DNA (ssDNA), followed by washing with 0.3×SSC/0.1% SDS at 48° C. As a result, several positive clones were obtained. These cDNA clones were separated by performing this plaque hybridization method in a plurality of times. Subsequently, a cDNA fragment of each phage was subcloned into a plasmid vector pBluescript II, and the nucleotide sequence was analyzed using a dideoxy sequence method [Sanger, F., Nicklen, S. and Coulson, A. R. (1977) Proc. Natl. Acd. Sci. U.S.A. 74, 5463–5467]. Based on a putative amino acid sequence, LDL receptors themselves were excluded, and cDNA clones having a sequence very similar to that of LDL receptors were identified. Using these clones as cDNA probes, the cDNA library was screened to thereby obtain overlapping two clones. These were employed as new probes and similar procedure was performed, so as to obtain 5 cDNA clones. The DNA nucleotide sequence determined by these cDNA clones are shown as Sequence ID No. 2. The total length of the sequence was 6961 bp. In the open reading frame of 6639 bp (Sequence ID No. 1) which contained a sequence exhibiting high homology with LDL receptors, there existed on the 5' side an ATG codon which was presumably a translation initiating site and a successive highly hydrophobic sequence consisting of about 30 amino acids. Accordingly, the obtained cDNA was considered to contain the entirety of its length. A putative amino acid sequence is shown as Sequence ID No. 3. The protein consisted of 2213 amino acids. Comparison of the amino acid sequence of the protein with other amino acid sequence data registered at the Genebank, there was a very high similarity to LDL receptors. That is, amino acids 700–1,100 in the sequence were very similar to the EGF precursor homology region of LDL receptors, and amino acids 1,100–1,640 were also very similar to the ligand binding region of LDL receptors. When the amino acid sequence of the subject protein was compared with other lipoprotein receptor LRP, gp330, and VLDL receptors, similarity was not as high as that observed for LDL receptors. On the C-terminal side of the amino acid sequence of the protein, there was found a highly hydrophobic region which was very similar to the transmembrane region of LDL receptors.

Example 3

From liver tissue and brain tissue of a male Japanese white rabbit, intact RNA was extracted through a guanidium thiocyanate/cesium chloride method. The obtained intact RNA was subjected to an oligo (dT) cellulose column method to thereby obtain purified poly(A)$^+$RNA. The poly (A)$^+$RNA specimens (10 µg each) was modified via a glyoxal method, electrophoresed on 1% agarose gel, and transferred onto a nylon membrane.

For human tissue mRNA, commercially available nylon membranes blotted with human tissue poly(A)$^+$RNA from various sources were used.

Using as a probe part of a $^{32}$P-labelled rabbit cDNA of the present invention, hybridization was performed at 42° C. using 50% (rabbit) or 40% (human) formamide, 0.1% SDS, 50 mM phosphate buffer, 5×Denhardt's, 5×SSC, and 200 µg/ml of ssDNA, followed by washing with 0.1×SSC and 0.1% SDS at 50° C. Autoradiography was performed at −70° C. for 2 days in the presence of intensifying screen. As a result, in both rabbit liver tissue and brain tissue, mRNA of about 7 kb was detected as well as mRNA of about 15 kb which was considered to result from alternative splicing or polyadenylation. The size of the mRNA of about 7 kb coincided with that of the rabbit cDNA of the present invention. Also, in human liver tissue and brain tissue, it was confirmed that mRNA having the same size was expressed.

Example 4

Screening of human brain cDNA library for positive clones and determination of the nucleotide sequence of cDNA fragments The human brain cDNA library used in this Example was a commercially obtained cDNA library which was constructed using λgt10 as a vector. Using partial cDNA of the present invention as a probe, screening of the cDNA library (300,000 plaques) was performed using a plaque hybridization method. Procedures of screening, cloning, and sequencing were as described in Example 2 of the present invention.

As a result of screening of the human brain cDNA library, positive clones containing a DNA fragment of about 3 kb were obtained. Analysis of the nucleotide sequence of part of the cDNA fragment revealed that the fragment was highly homologous to the cDNA of the present invention (Sequence ID No. 4).

Example 5

Cloning of cDNA of receptors in the human LDL receptor family:

A human brain cDNA library was subjected to screening using fragments of the cDNA of the present invention and fragments of the cDNA obtained in Example 4 as probes. Procedures of screening, cloning, and sequencing were as described in Example 2 of the present invention.

Through screening of the human brain cDNA library, two positive clones containing cDNA fragments of about 6 kb and about 3 kb were obtained. When their nucleotide sequence was analyzed, they were identified to be a cDNA clone containing the cDNA nucleotide sequence obtained in Example 4 and a cDNA clone that overlapped therewith. Using part of these cDNAs as probes, procedures similar to those as described above were performed, to thereby obtain another cDNA clone. The DNA nucleotide sequence indicated by these cDNA clones are shown as Sequence ID No. 6. The total length of the sequence was 6,843 bp. There was an open reading frame having a size of 6,642 bp (Sequence ID No. 5). A putative amino acid sequence is shown as Sequence ID No. 7. The protein consisted of 2,214 amino acids. Comparison of the amino acid sequence with that of rabbit protein shown by Sequence ID No. 3 revealed high homology of not less than 94%.

Example 6

Creation of cells that express receptors in the rabbit LDL receptor family:

The cDNA as shown by Sequence ID No. 2 was ligated to phosphorylated EcoRI linker pd (CCGAATTCGG) (SEQ ID NO:8) by the use of a T4 DNA ligase, and the resultant ligated product was digested with EcoRI. Separately, a vector for expression, pBK-CMV was digested with EcoRI. The aforementioned DNA was ligated to the EcoRI-digested site of the vector using a T4 DNA ligase.

Using the resultant recombinant expression vector in a calcium phosphate method [Chen, C. and H. Okayama (1987) Mol. Cell. Biol. 7, 2945–2752], host cells (CHO-1d1A7) were transformed. The resultant transformants were incubated in a Ham's F-12 selective medium supplemented with 500 µg/ml of G418, and viable cells were separated as LDL receptor analog protein-expressing cells. The cells were incubated further in the aforementioned medium.

Example 7

Ligand analysis of the LDL receptor analog protein by ligand blotting:

The obtained LDL receptor analog protein-expressing cells and control cells were suspended in a buffer solution containing 200 mM Tris-maleic acid (pH 6.5), 2 mM calcium chloride, 0.5 mM PMSF, 2.5 µM leupeptin, and 1% Triton X-100, to thereby solubilize the membrane protein. Solubilized membrane protein fractions were obtained through centrifugation, and electrophoresed by a 4.5–18% gradient SDS-PAGE. Thereafter, the protein was transferred onto a nitrocellulose membrane.

Incubation was performed in a buffer of 50 mM Tris-HCl (pH 8.0) containing $^{125}$I-labelled β-VLDL (10 µg/ml), 2 mM calcium chloride, and 5% bovine serum albumin. Autoradiography was performed at room temperature.

A single band of about 250 kDa was detected in membrane protein fractions prepared using the present protein-expressing cells. This size coincided well with the molecular weight of 248 kDa calculated regarding the amino acid sequence (Sequence ID No. 3) deduced from the cDNA of the present invention. Although a similar band was detected for control cells, the expression level was much lower as compared with the case of the present protein-expressing cells.

Since the protein coded by the cDNA of the present invention is considered to be a novel LDL receptor family receptor, it is expected that through analyses of this protein, details of lipoprotein metabolism mediated by the membrane receptor will be elucidated, and pathology of abnormal lipid metabolism which triggers onset and progress of arteriosclerosis will be clarified.

---

---

What is claimed is:

1. DNA having a nucleotide sequence as shown in SEQ ID NO: 1.

2. An isolated and purified LDL receptor analog protein having an amino acid sequence as shown in SEQ ID NO: 3.

3. DNA having a nucleotide sequence as shown in SEQ ID NO: 5.

4. An isolated and purified LDL receptor analog protein having an amino acid sequence as shown in SEQ ID NO: 7.

5. A recombinant expression vector comprising DNA as shown by Sequence ID No. 1 or 5.

6. Transformant cells which harbor the recombinant expression vector of claim 5.

7. A method for the production of an LDL receptor analog protein comprising the steps of culturing the transformant cells of claim 6 and collecting said LDL receptor analog protein produced in the culture.

* * * * *